US011001880B2

(12) United States Patent
Farris et al.

(10) Patent No.: US 11,001,880 B2
(45) Date of Patent: May 11, 2021

(54) DEVELOPMENT OF SNP ISLANDS AND APPLICATION OF SNP ISLANDS IN GENOMIC ANALYSIS

(71) Applicant: The MITRE Corporation, McLean, VA (US)

(72) Inventors: Michael Heath Farris, Vienna, VA (US); Andrew Roger Scott, McLean, VA (US); Pamela Ann Texter, Naples, FL (US)

(73) Assignee: The MITRE Corporation, McLean, VA (US)

( * ) Notice: Subject to any disclaimer, the term of this patent is extended or adjusted under 35 U.S.C. 154(b) by 215 days.

(21) Appl. No.: 15/282,968

(22) Filed: Sep. 30, 2016

(65) Prior Publication Data

US 2018/0094303 A1 Apr. 5, 2018

(51) Int. Cl.
*C12Q 1/6848* (2018.01)
*C12Q 1/6811* (2018.01)
(Continued)

(52) U.S. Cl.
CPC .......... *C12Q 1/6848* (2013.01); *C12Q 1/6811* (2013.01); *G16B 20/20* (2019.02);
(Continued)

(58) Field of Classification Search
None
See application file for complete search history.

(56) References Cited

U.S. PATENT DOCUMENTS 7,115,726 B2 10/2006 Cox et al.
7,211,388 B2  5/2007 Cash et al.
(Continued)

FOREIGN PATENT DOCUMENTS

JP          4994676      8/2012
WO    WO 2015/194655   12/2015
WO    WO 2015/195816   12/2015

OTHER PUBLICATIONS

Vieux et al. Primer Design for PCR and Sequencing in High-Throughput Analysis of SNPs. Biotechniques, vol. 32, pp. S28-S32 (Year: 2002).*

(Continued)

*Primary Examiner* — Olivia M. Wise
(74) *Attorney, Agent, or Firm* — Morrison & Foerster LLP

(57) ABSTRACT

Techniques are provided for locating and validating single-nucleotide polymorphism (SNP) islands by scanning a reference genome. A system scans a reference genome to locate a high-variance region containing at least a minimum number of known impactful SNP locations in less than a maximum length, wherein the high-variance region is flanked by low-variance regions of at least minimum length and each having fewer than a maximum number of known relevant SNP locations. The system allows for tuning maximum and minimum region lengths, maximum and minimum SNP-location quantities, and rate-of-occurrence thresholds that define relevant and/or impactful SNP locations. Primers are designed for portions of the low-variance regions that are unique within the reference genome, wherein the primers amplify for the high-variance region. The primers are used to amplify genetic material samples in order to perform analyses to distinguish sample identity and/or to determine whether a sample corresponds to single or multiple contributors.

15 Claims, 25 Drawing Sheets

(4 of 25 Drawing Sheet(s) Filed in Color)

Specification includes a Sequence Listing.

(51) Int. Cl.
  *G16B 30/00* (2019.01)
  *G16B 20/20* (2019.01)
  *G16B 25/20* (2019.01)
(52) U.S. Cl.
  CPC .............. *G16B 25/20* (2019.02); *G16B 30/00* (2019.02); *C12Q 2500/00* (2013.01)

(56) References Cited

U.S. PATENT DOCUMENTS

| | | |
|---|---|---|
| 7,482,117 B2 | 1/2009 | Cargill et al. |
| 7,981,609 B2 | 7/2011 | Rubin et al. |
| 8,271,201 B2 | 9/2012 | Chakraborty et al. |
| 8,285,486 B2 | 10/2012 | Martin et al. |
| 8,380,442 B2 | 2/2013 | Ecker et al. |
| 8,802,372 B2 | 8/2014 | Ecker et al. |
| 9,116,882 B1 | 8/2015 | Macpherson et al. |
| 9,183,349 B2 | 11/2015 | Kupershmidt et al. |
| 2004/0023275 A1 | 1/2004 | Berno et al. |
| 2005/0272057 A1 | 12/2005 | Abrahamsen et al. |
| 2006/0094010 A1 | 5/2006 | Giles et al. |
| 2010/0114956 A1 | 5/2010 | McElfresh et al. |
| 2011/0312534 A1 | 12/2011 | Kayser et al. |
| 2012/0153018 A1 | 6/2012 | Nietfeld |
| 2013/0166599 A1 | 6/2013 | Kupershmidt et al. |
| 2015/0017632 A1 | 1/2015 | Matsuzaki et al. |
| 2015/0310165 A1 | 10/2015 | Mann |
| 2016/0085910 A1 | 3/2016 | Bruand et al. |

OTHER PUBLICATIONS

Zhang et al. Haplotype Block Partitioning and Tag SNP Selection Using Genotype Data and Their Applications to Association Studies. Genome Research, vol. 14, pp. 908-916 (Year: 2004).*
Shendure et al. Next-Generation DNA Sequencing. Nature Biotechnology 2008, vol. 26, No. 10, pp. 1135-1145 (Year: 2008).*
You et al. BatchPrimer3: A high throughput web application for PCR and sequencign primer design. BMC Bioinformatics, vol. 9, No. 253, pp. 1-13 (Year: 2008).*
You et al. ConservedPrimers 2.0: A high-throughput pipeline of comaprative genome referenced intron-flanking PCR primer design and its application in wheat SNP discovery. BMC Bioinformatics, vo. 10, No. 331, pp. 1-11 (Year: 2009).*
Rozen et al. Primer3 on the WWW for General Users and for Biologist Programmers. Methods in Molecular Biology, vol. 132: Bioinformatics and Protocols, Edited by: S. Misenher and S.A. Krawetz, Humana Press Inc, Totowa, NJ, pp. 365-386 (Year: 2000).*
Yao et al. PrimerSNP: a web tool for whole-genome selection of allele-specific and common primers of phylogenetically-related bacterial genomic sequences. BMC Microbiology, vol. 8, No. 185, pp. 1-9 (Year: 2008).*
Rodriguez et al. Design of Primers and Probes for Quantitative Real-Time PCR Methods. PCR Primer Design, Methods in Molecular Biology vol. 1275, edited by Chhandak Basu, pp. 31-56 (Year: 2015).*
Pessoa et al. PrimerIdent: A web based tool for conserved primer design. Bioinformation vol. 5, No. 2, pp. 52-54 (Year: 2010).*
Feature (2003) "The International HapMap Project," Nature, vol. 426; 9 pages.
Rajeevan, H. et al. (2003) "ALFRED: the ALelle FREquency Database, Update," Nucleic Acids Research, vol. 31, No. 1, pp. 270-271.
Applied Biosystems (2003) "Creating Standard Curves with Genomic DNA or Plasmid DNA Templates for Use in Quantitative PCR," (http://www.appliedbiosyslems.com/support/tutorials/pdl/quant.pcr.pdl; 9 pages.
Kidd, K.K. et al. (2006) "Developing a SNP panel for forensic identification of individuals," Forensic Science International 164, pp. 20-32.

Sanchez, J.J. et al. (2006) "A multiplex assay with 52 single nucleotide polymorphisms for human identification," Electrophoresis 27, pp. 1713-1724.
Phillips, C. et al. (2007) "Inferring ancestral origin using a single multiplex assay of ancestry-informative marker SNPs," Forensic Science International: Genetics I, pp. 273-280.
Pakstis, A.J. et al. (2007) "Candidate SNPs for a universal individual identification panel," Hum Genet 121, pp. 305-317.
Barreiro, L.B. et al. (2008) "Natural selection has driven population differentiation in modern humans," Nature Genetics, vol. 40, No. 3, pp. 340-345.
Li, J.Z. et al. (2008) "Worldwide Human Relationships Inferred from Genome-Wide Patterns of Variation," Science, vol. 319, pp. 1100-1104.
Ge, J. (2008) "Computational Algorithms and Evidence Interpretation in DNA Forensics based on Genomic Data," ProQuest Dissertations, Univ. of Cincinnati; 163 pages.
Li, H. et al. (2009) "The Sequence Alignment/Map format and SAMtools," Bioinformatics Applications Note, vol. 25, No. 16, pp. 2078-2079.
Altshuler, D.M. et al. (2010) "Integrating common and rare genetic variation in diverse human populations," Nature 467(7311); 18 pgs.
Pakstis, A. J. et al. (2010) "SNPs for a universal individual identification panel," Hum Genet 127, pp. 315-324.
Kircher, M. et al. (2010) "High-throughput DNA sequencing—concepts and limitations," Bioessays 32, pp. 524-536.
Sangket, U. et al. (2010) "ParallABEL: an R library for generalized parallelization of genome-wide association studies," BMC Bioinformatics 11:217; 11 pages.
Tomas, C. et al. (2011) "Autosomal SNP typing of forensic samples with the GenPlex$^{TM}$ HID System: Results of a collaborative study," Forensic Science International: Genetics 5, pp. 369-375.
Kidd, J.R. et al. (2011) "Analyses of a set of 128 ancestry informative single-nucleotide polymorphisms in a global set of 119 population samples," Investigative Genetics 2:1; 13 pages.
Alkan, C. et al. (2011) "Limitations of next-generation genome sequence assembly," Nature Methods 8(1); 9 pages.
Article (2012) "An integrated encyclopedia of DNA elements in the human genome," Nature, vol. 489, pp. 57-74.
Li, H. (2012) "Exploring single-sample SNP and INDEL calling with shole-genome *de novo* assembly," Bioinformatics Original Paper, vol. 28, No. 14, pp. 1838-1844.
Koboldt, D.C. et al. (2012) "Massively Parallel Sequencing Approaches for Characterization of Structural Variation," Methods Mol Biol, 838; 14 pages.
Lawson, D.J. (2012) "Similarity matrices and clustering algorithms for population identification using genetic data," Genomics and Human Genetics 13; 34 pages.
Seo, S.B. et al. (2013) "Single nucleotide polymorphism typing with massively parallel sequencing for human identification," Int. J. Legal Med. 127, pp. 1079-1086.
Van Der Auwera, G.A. et al. (2013) "From FastQ data to high confidence variant calls: the Genome Analysis Toolkit best practices pipeline," Curr Protoc Bioinformatics 11(1110); 43 pages.
Wang, Y. et al. (2013) "Using Aggregate Human Genome Data for Individual Identification," the Institute of Electrical and Electronics Engines, Inc. (IEEE) Conference Proceedings; 6 pages.
Bolger, A.M. et al. (2014) "Trimmomatic: a flexible trimmer for Illumina sequence data," Bioinformatics Original Paper, vol. 30, No. 15, pp. 2114-2120.
Auton, A. et al. (2015) "A global reference for human genetic variation," Nature, vol. 526; 20 pages.
Cai, R. et al. (2015) "Deterministic Identification of Specific Individuals from GWAS Results," Bioinformatics, pp. 1-7.
Churchill, J.D. et al. (2016) "Evaluation of the Illumina® Beta Version ForenSeq™ DNA Signature Prep Kit for use in genetic profiling," Forensic Science International: Genetics 20, pp. 20-29.
Zheng, X. et al. (2016) "Eigenanalysis of SNP data with an identity by descent interpretation," Theoretical Population Biology 107, pp. 65-76.

(56) References Cited

OTHER PUBLICATIONS

Sherry, S.T. et al. (2001) "dbSNP: the NCBI database of genetic variation," Nucleic Acids Research, vol. 29, No. 1, pp. 308-311.

* cited by examiner

| Chromosome | Target Identification Filter | | | Sequence Repetition Rejection Filter | | | Primer Design Feasibility Filter | | |
|---|---|---|---|---|---|---|---|---|---|
| | 5-SNP | 4-SNP | 3-SNP | 5-SNP | 4-SNP | 3-SNP | 5-SNP | 4-SNP | 3-SNP |
| 1 | 311 | 1231 | 4557 | 126 | 478 | 1689 | 3 | 0 | 2 |
| 2 | 350 | 1185 | 4666 | 131 | 444 | 1759 | 2 | 0 | 1 |
| 3 | 288 | 1085 | 3973 | 116 | 417 | 1530 | 0 | 0 | 6 |
| 4 | 368 | 1218 | 4306 | 137 | 463 | 1699 | 0 | 0 | 4 |
| 5 | 256 | 939 | 3546 | 80 | 328 | 1314 | 0 | 1 | 0 |
| 6 | 289 | 987 | 3717 | 104 | 374 | 1414 | 1 | 1 | 3 |
| 7 | 255 | 933 | 3393 | 79 | 326 | 1244 | 0 | 2 | 0 |
| 8 | 203 | 748 | 3015 | 83 | 297 | 1229 | 1 | 1 | 2 |
| 9 | 167 | 581 | 2333 | 55 | 192 | 902 | 1 | 0 | 0 |
| 10 | 230 | 819 | 2891 | 76 | 300 | 1143 | 1 | 0 | 0 |
| 11 | 228 | 754 | 2878 | 96 | 299 | 1197 | 0 | 0 | 2 |
| 12 | 201 | 732 | 2593 | 62 | 261 | 967 | 1 | 0 | 2 |
| 13 | 181 | 608 | 2179 | 62 | 221 | 797 | 0 | 0 | 2 |
| 14 | 120 | 469 | 1748 | 32 | 168 | 641 | 1 | 0 | 1 |
| 15 | 129 | 446 | 1653 | 44 | 152 | 617 | 0 | 0 | 0 |
| 16 | 140 | 416 | 1630 | 41 | 144 | 589 | 0 | 1 | 1 |
| 17 | 123 | 446 | 1654 | 37 | 151 | 566 | 0 | 1 | 2 |
| 18 | 123 | 444 | 1597 | 54 | 164 | 587 | 0 | 0 | 1 |
| 19 | 126 | 411 | 1399 | 36 | 99 | 362 | 0 | 0 | 0 |
| 20 | 108 | 377 | 1372 | 38 | 139 | 521 | 0 | 0 | 3 |
| 21 | 93 | 302 | 993 | 28 | 111 | 370 | 0 | 0 | 2 |
| 22 | 60 | 199 | 751 | 23 | 68 | 275 | 1 | 0 | 0 |
| X | 119 | 485 | 2027 | 41 | 154 | 722 | 0 | 1 | 0 |
| Y | 0 | 0 | 0 | 0 | 0 | 0 | 0 | 0 | 0 |
| TOTAL | 4,468 | 15,815 | 58,871 | 1,581 | 5,750 | 22,134 | 12 | 8 | 34 |

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| LUZP1i | 1:23419097-23419574 | 477 | 1:23419261 | rs477717 | 30.95% (G) | G | A | TACTTGACTTCCGTT GCCAAGCACGTGTC CCCTCTTGC | TCCTCAGCATAAGC GGGAACGACTCCGG AACAGGGAGTTT |
| | | | 1:23419283 | rs35917050 | 2.24% (A) | G | A | | |
| | | | 1:23419374 | rs3765407 | 32.31% (G) | G | T | | |
| | | | 1:23419383 | rs477830 | 30.97% (C) | C | T | | |
| LUZP1iii | 1:23419203-23419574 | 371 | 1:23419261 | rs477717 | 30.95% (G) | G | A | ATCCATGGGTGGTG TCACTAAACGTTCGT GTTGTCTTCTC | TCCTCAGCATAAGC GGGAACGACTCCGG AACAGGGAGTTT |
| | | | 1:23419283 | rs35917050 | 2.24% (A) | G | A | | |
| | | | 1:23419374 | rs3765407 | 32.31% (G) | G | T | | |
| | | | 1:23419383 | rs477830 | 30.97% (C) | C | T | | |
| ERBB4 | 2:212264500-212264885 | 385 | 2:212264533 | NSV | | G | T | TGCTTTGGAAGACCT AGAGAACCAGGGTT TAGCTGTATC | TTTAAGGCAGCGGG GCTGTTGGATGACC GTCCTTTCTCTTA |
| | | | 2:212264534 | NSV | | T | G | | |
| | | | 2:212264560 | rs3791691 | 28.90% (T) | C | T | | |
| | | | 2:212264598 | rs3791692 | 36.96% (G) | G | A | | |
| | | | 2:212264642 | rs4673613 | 36.24% (C) | T | C | | |
| | | | 2:212264646 | rs77175994 | 3.43% (T) | C | T | | |
| | | | 2:212264802 | rs4673614 | 35.92% (T) | A | T | | |
| | | | 2:212264814 | NSV | | G | T | | |
| | | | 2:212264818 | rs7585000 | 37.70% (C) | A | C | | |
| | | | 2:212264855 | NSV | | G | A | | |
| Chr3:94373 | 3:1094373-1094721 | 348 | 3:1094443 | rs2727993 | 48.34% (A) | A | G | ACTTACAACAACTG GAGTTTGGCTTGTC AAGAGTGGTGCAGA | ACTGTCTGTGCTCA ATTACCTGCTCCTAC ACCATCCTACAC |
| | | | 3:1094516 | rs2727994 | 48.30% (A) | A | G | | |
| | | | 3:1094524 | NSV | | G | T | | |
| | | | 3:1094526 | rs113173277 | 1.34% (T) | C | T | | |
| | | | 3:1094604 | rs12632405 | 17.91% (G) | T | G | | |

Fig. 7B

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| RFTN1 | 3:16397692-16398098 | 406 | 3:16397740 | NSV | | C | A | ACCTGCCCACACTC GCTTGGCATCTTGG ACTGAGCTTTACT | GGGGGGTGAGTTG GATGTCCCCGGGA CACTATTACTCAG |
| | | | 3:16397749 | NSV | | T | C | | |
| | | | 3:16397755 | NSV | | T | C | | |
| | | | 3:16397814 | rs140429135 | 4.09% (A) | G | A | | |
| | | | 3:16397878 | rs7634895 | 32.11% (C) | T | C | | |
| | | | 3:16397921 | rs75696774 | 2.30% (T) | C | T | | |
| | | | 3:16397944 | rs117459672 | 4.09% (T) | C/G | T | | |
| | | | 3:16398086 | NSV | | C | T | | |
| ARHGEF3 | 3:57010820-57011276 | 456 | 3:57010995 | rs181361690 | 0.08% (A) | G | A | GGGAGTGGAACTGC GTCAGGCTTGTTAG AGCTCATGTGGTAG | GTCATTTTCTCGCC CCAGTTGTGGCTC TTGTGGATTAG |
| | | | 3:57011075 | rs9882789 | 46% (G) | A | G | | |
| | | | 3:57011075 | rs368071441 | 0.14% (-) | A | - | | |
| | | | 3:57011100 | rs183691789 | 0.02% (G) | A | G | | |
| | | | 3:57011234 | rs13080107 | 45.89% (C) | T | C | | |
| | | | 3:57011234 | rs386661228 | ? | TG | CA | | |
| | | | 3:57011235 | rs795444289 | 5.01% (A) | G | A | | |
| | | | 3:57011235 | rs386661228 | ? | TG | CA | | |
| ROBO2 | 3:77720194-77720564 | 370 | 3:77720284 | rs4525838 | 37.2% (A) | C | A | GAACACCCTGTTGT TATAGGGATGATAG GATTACAGAGTAAC | TTGCAGTAGCATTG CAGGGAACTTCCGC AAATGCCCCTGT |
| | | | 3:77720336 | rs2324816 | 37.24% (C) | T | C | | |
| | | | 3:77720464 | NSV | | C | A | | |
| Chr3:45339 | 3:145145339-145145679 | 340 | 3:145145414 | NSV | | G | C | ACTGTGGCTCCACG CTCAGCCCCATTGTT GGACCTGGCA | AATGCTGTACCACG CTCTTGCTTGCTAAA CTGTGAGAGTC |
| | | | 3:145145476 | rs7430464 | 44.27% | G | A | | |
| | | | 3:145145477 | rs7430466 | 44.27% | G | C | | |
| | | | 3:145145485 | rs62270108 | 44.27% | G | A | | |
| | | | 3:145145521 | rs1564488 | 58.95% | A | C | | |
| | | | 3:145145605 | rs3916049 | 44.03% | C | T | | |
| | | | 3:145145626 | rs3916050 | 44.05% | A | C | | |

Fig. 7C

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| Chr3:45379 | 3:145145379-145145679 | 300 | 3:145145414 | NSV |  | G | C | CTGTGAGCGGCTTC AGCATCGGGCGCTG ACGTCCAGATGA | AATGCTGTACCAC GCTCTTGCTTGCTAA ACTGTGAGAGTC |
|  |  |  | 3:145145476 | rs7430464 | 44.27% | G | C |  |  |
|  |  |  | 3:145145477 | rs7430466 | 44.27% | G | A |  |  |
|  |  |  | 3:145145485 | rs62270108 | 44.27% | G | C |  |  |
|  |  |  | 3:145145521 | rs1564488 | 58.95% | A | C |  |  |
|  |  |  | 3:145145605 | rs3916049 | 44.03% | C | T |  |  |
|  |  |  | 3:145145626 | rs3916050 | 44.05% | A | C |  |  |
| SLC2A9 | 4:9965249-9965750 | 501 | 4:9965432 | NSV |  | C | T | GAGAGGGCCTCTCA AGAGGCCCCTGCTC GCTGGGTTTGCA | TTGTAAGAATTCTCG AATGTCTCCCCCTC GATATTCAG |
|  |  |  | 4:9965443 | rs6856127 | 41.69% (C) | T | C |  |  |
|  |  |  | 4:9965612 | NSV |  | G | T |  |  |
|  |  |  | 4:9965633 | rs6840802 | 40.93% (G) | C/A | G |  |  |
|  |  |  | 4:9965673 | NSV |  | G | T |  |  |
| ST3GAL1P1 | 4:68586070-68586580 | 510 | 4:68586197 | rs139445314 | 0.10% (G) | C | G | ATAAGTCTGCAGA GTACATAGTCCAGT CGTTGTGTGAT | TGATGAGAAGCCGG TGGTGAGCAGTTGT ACAAGATCCACAG |
|  |  |  | 4:68586267 | rs17635222 | 16.03% (C) | G | C |  |  |
|  |  |  | 4:68586315 | rs13124793 | 14.00% (A) | G | A |  |  |
|  |  |  | 4:68586335 | rs72643632 | 17.79% (C) | T | C |  |  |
|  |  |  | 4:68586335 | rs35801483 | ? | TA | CG |  |  |
|  |  |  | 4:68586336 | rs17635292 | 14.22% (G) | A/C | G |  |  |
|  |  |  | 4:68586336 | rs35801483 |  | TA | CG |  |  |
|  |  |  | 4:68586450 | rs7697056 | 34.88% (A) | C | A |  |  |
|  |  |  | 4:68586509 | rs6552111 | 34.88% (T) | C | T |  |  |
| GRID2 | 4:93309655-93310185 | 530 | 4:93309731 | NSV |  | T | C | TACAGTCTACATAAT CATGCCCCACAACG GCTATCTTTAGCA | TTTGGGTTAACCAGT ATTAAGGGCCGGTT TCCATTACTG |
|  |  |  | 4:93309909 | rs13122638 | 40.64% (C) | T | C |  |  |
|  |  |  | 4:93309955 | rs13122662 | 40.62% (C) | T | C |  |  |

Fig. 7D

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| Chr4:53970 | 4:184453970-184454377 | 407 | 4:184454079 | rs4440262 | 32.83% (G) | T | G | CTGGCAGATGATCC CCTCAGCCAGGTCT AGGGCTTACCCT | TGCTGCCCTTCAGT ACCGACTTTGGAAG CAGTACCGAAGT |
| | | | 4:184454084 | rs4518295 | 38.16% (G) | T | G | | |
| | | | 4:184454112 | NSV | | G | T | | |
| | | | 4:184454164 | NSV | | T | A | | |
| | | | 4:184454194 | rs7670109 | 46.03% (A) | G | A | | |
| MAP3K7 | 6:91318430-91318859 | 429 | 6:91318461 | rs564545140 | 0.02% (T) | C | T | TTGGTGGAAGCTGC GAGTGAGGGGCCTC TCTCGGTGTTTCC | TCAACAATTGTTACC TTAACAAAACCGTTC TAGCCACTTT |
| | | | 6:91318479 | rs9294463 | 38.72% (G) | A | G | | |
| | | | 6:91318706 | rs190232649 | 0.26% (T) | C | T | | |
| | | | 6:91318722 | rs401147 | 40.46% (T) | T | C | | |
| | | | 6:91318768 | rs398026 | 40.46% (A) | A | G | | |
| TNKS | 8:9571206-9571735 | 529 | 8:9571364 | rs7462070 | 44.09% (C) | C | T | TGCTATCAGTAGATA TCAAATGCCGTAGC AACTCCTATTTAC | GCATGCCTGTCTAG GTTATATATGGCGTA CATTTAGTTTA |
| | | | 8:9571399 | rs113085501 | 0.30% (C) | T | C | | |
| | | | 8:9571445 | rs7459728 | 30.89% (T) | T | C | | |
| | | | 8:9571506 | rs284115429 | 1.98% (G) | C | G | | |
| | | | 8:9571621 | rs7461939 | 44.07% (G) | G | A | | |
| EYA1 | 8:72111431-72111846 | 415 | 8:72111599 | rs10103397 | 47.66% (G) | A | G | GGCAGAGGTCAAGA CTGACAGCAACTGC GCATCACCAGGCGG | CAACTCAGTCCAGT ATTCTTAGGGGAGG ATTGAGTTTGAAT |
| | | | 8:72111658 | rs1171149407 | 0.78% (A) | G | A | | |
| | | | 8:72111678 | rs100090382 | 47.50% (C) | T | C | | |
| | | | 8:72111710 | rs101103644 | 17.49% (T) | C | T | | |
| | | | 8:72111739 | rs101103852 | 47.28% (C) | G | C | | |
| ANO1 | 11:69981445-69981895 | 450 | 11:69981591 | rs7947793 | 44.01% (A) | C | A | TATTCCCATGAGTTA AGGAGACGCTGGC GGGCTTGGCCGAG | ACAGCCCAAGACGG CTTCTTTCTTCATCC GGGCTCCTTCAG |
| | | | 11:69981736 | rs7947936 | 46.91% (G) | C | G | | |

Fig. 7E

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| OR10G6 | 11:123874598-123875090 | 492 | 11:123874762 | rs11603189 | 21.01% (T) | A | T | CTTCTCAACATTACG ACGATTGACGGATC ATAAGTAGTGGGA | GGTCAGAGTAATTC GACATTCTACTAAG GTGGACTTGGTTCC |
| | | | 11:123874768 | rs10750254 | 46.65% (C) | T | C | | |
| | | | 11:123874858 | NSV | | A | G | | |
| | | | 11:123874903 | NSV | | A | G | | |
| | | | 11:123874966 | rs10750255 | 44.99% (A) | G | A | | |
| | | | 11:123874984 | NSV | | T | T | | |
| | | | 11:123875012 | NSV | | A | G | | |
| | | | 11:123875032 | rs538121404 | ? | G | T | | |
| Chr12:53244 | 12:43253244-43253623 | 379 | 12:43253415 | rs1520832 | 4.49% (T) | T | G | TATGAAAGCTGGAC GAGCAGAATTCCCA AACTTTGGTCTGA | TTGCCCACTCACTA GACAGCCGCTCCAT CGCAAGGCTCTCTG |
| | | | 12:43253469 | rs7308945 | 31.83% (T) | A | T | | |
| | | | 12:43253536 | rs572369996 | 0.02% (A) | G/C | A | | |
| HOXC13 | 12:54319518-54320066 | 548 | 12:54319727 | rs8894734 | 41.01% (A) | A | G | TATCACATTAAACCG AGTCAGAGTCTTG AAGCTACATTGC | AGTTCTAATTAATGG AATGCATGTGCCGT TTCCTGGCCAA |
| SGCG | 13:237562441-23756710 | 469 | 13:23756283 | NSV | | T | G | ATATCAGCTAAGCTT GCAGTTAAAATGCG GAAAATGAAATT | CCTGCAATCCTCAT GAGAACGTCGTAGA ACTATCTGGCCCT |
| | | | 13:23756363 | rs571976 | 24.22% (G) | G | A | | |
| | | | 13:23756594 | rs3794371 | 47.70% (A) | G | A | | |
| | | | 13:23756627 | rs3794370 | 49.14% (G) | T | G | | |
| Chr13:46674 | 13:112546674-112547008 | 334 | 13:112546833 | rs3903774 | 25.38% (G) | A | G | CACCCAAAGTATGT GGCTCAGCACCGTG CTTATAGGACAC | CATTTGAATAGGGC GTATGTCTTTGGTTG GGCAATGAA |
| | | | 13:112546866 | rs1923740 | 35.32% (C) | C | A | | |
| RAD51B | 14:691147989-69148447 | 458 | 14:69148127 | rs1884808 | 40.22% (A) | A | G | TGGAGTGTCTACTC GAGGTGTTCCAAAT CAGCGGAGAGTC | GGGAGGTTATTATA CAGTGGCCCAGGAC ACGATATTACACA |
| | | | 14:69148298 | rs1884807 | 42.33% (A) | G | A | | |
| RBFOX1 | 16:5994157-5994565 | 408 | 16:5994224 | rs4786793 | 31.35% (G) | A/C | G | TGGCCATTGATCTAA TGACCTCAACGATG TGTGAACAATG | TCACACAGCTCCGA AGGGACCAACTCGG GATTTGCAGCCA |
| | | | 16:5994311 | rs7202039 | 31.33% (T) | T | C | | |
| | | | 16:5994318 | rs7202046 | 31.33% (T) | T | C | | |
| | | | 16:5994402 | rs7195248 | 31.35% (G) | G | C | | |
| | | | 16:5994525 | rs7196781 | 14.02% (G) | C | G | | |

Fig. 7F

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| NUP88 | 17:5295079-5295578 | 499 | 17:5295307 | rs148519577 | 0.30% (T) | C | T | | |
| | | | 17:5295357 | rs1806236 | 3.13% (C) | T | C | | |
| | | | 17:5295371 | rs3026129 | 44.77% (T) | T | C | | |
| | | | 17:5295399 | rs1806237 | 44.79% (C) | C | T | TGAAGTTGCTTGGGACATCCTATCAGTACCATAACCTCAA | GTGTGAGAGGAGGCGGCATCCACATTCGGGGGCAGATGTG |
| | | | 17:5295502 | rs1806238 | 44.79% (C) | C | T | | |
| | | | 17:5295528 | rs1806239 | 44.79% (T) | T | C | | |
| | | | 17:5295529 | NSV | | G | T | | |
| | | | 17:5295534 | NSV | | C | G | | |
| | | | 17:5295547 | NSV | | C | G | | |
| NSF | 17:44799862-44800319 | 457 | 17:44800046 | rs7224296 | 47.18% (G) | G | A | CTACCTAAAGTTGTGGTGCAGCTTCCCGGCTTAGTATGTAA | TTTTGCAGTCGGTCTCTGTGCTAATTACTATCAGAGGAG |
| | | | 17:44800110 | rs199454 | 39.12% (G) | G | A | | |
| | | | 17:44800121 | rs115851737 | 2.92% (A) | A | G | | |
| ZADH2 | 18:72919745-72920249 | 504 | 18:72919995 | NSV | | C | A | GTCCTTCAGTCCGTGCAAGGGACTTTACGGTACTTTCTAGTA | GTCTGCGTGCTGTCAGTGCAGTGTGACTGTTGTCTGTCC |
| | | | 18:72920041 | NSV | | G | T | | |
| | | | 18:72920065 | rs12969004 | 30.45% (A) | G | A | | |
| | | | 18:72920070 | NSV | | T | A | | |
| | | | 18:72920103 | rs1866730 | 46.33% (A) | G | A | | |
| | | | 18:72920141 | NSV | | C | A | | |
| Chr20:36542 | 20:22136542-22137048 | 506 | 20:22136709 | rs804539 | 3.12% (G) | G | C | AACAATATGAGGCTCTTGACAGTCATAGTTTAGCCCCCTGG | GCCAAGTCTATATGCTGCCAAGGCTATATGCTGGGCATAA |
| | | | 20:22136786 | rs6047929 | 41.71% (G) | G | A | | |
| | | | 20:22136839 | rs6113548 | 42.35% (C) | T | C | | |
| Chr20:21389 | 20:39521389-39521826 | 437 | 20:39521581 | rs6129700 | 44.19% (G) | A | G | GGTGAGGACGGAAACTGTAAACTCCCGGGAACATTCTGGC | TGATCAGTTCTAGGCGTTGGGTCACCCTTTAGCACCAGGTC |
| | | | 20:39521617 | rs6124288 | 36.00% (C) | T | C | | |
| Chr20:66266 | 20:56566266-56566520 | 254 | 20:56566432 | rs6092579 | 43.20% (C) | T | C | GGCAGAGGGCGGGCCAGTGCTTGGAGTTAGCATGCCCTCCT | CACCAGCCCTAGGCGGTTAATGACTCGCTCAGTCCTTAA |
| | | | 20:56566479 | | | T | C | | |

Fig. 7G

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| RIPK4 | 21:43163937-43164483 | 546 | 21:43164232 | rs6092580 | 43.15% (T) | A/G | T | GGGTCAAGAAACTG TCCCCTTGATTCCGT TTAGCTTCTCAC | TGCTGTGCCGATGC GGGGTCTGAGCTCG GTGACCAATAGG |
|  |  |  | 21:43164345 |  |  | A | C |  |  |
| SLC19A1 | 21:46958834-46959343 | 509 | 21:46959087 | rs2277790 | 31.73% (A) | A | C | GCAGCAGCACGAAG CACACTCGAGGGCG TGTCTCTTTCA | GCCGGCCCTGTGGC GAGGCACAATTGTC CAACTGTCAGCC |
|  |  |  | 21:46959179 |  |  | G | A |  |  |
| SYNE3 | 14:95932757-95932898 | 141 | 14:95932819 | rs9976727 | 48.04% (A) | G | A | CTCAGTCCTACTGG ATAAGACCCTCTGC CAGTAAATAAGCT | TGCTGGAGGTAAAC GGCTCCCAAGATG CAT |
|  |  |  | 14:95932844 | rs758271841 | ? | C | T | CCCTGCGTGAGGGT AGGAGC |  |
| PRUNE2 | 9:79312327-79312837 | 510 | 9:79312409 | rs488165 | 43.89% (A) | G | A | GCCTCCAACCACTC GAGTTGGTCCCACA | TTCCATAGTAAGTGC TTGCAGACTGACAA |
|  |  |  | 9:79312491 | rs489069 | 44.29% (A) | C | A |  |  |
|  |  |  | 9:79312556 | rs10869797 | 33.51% (A) | G | A |  |  |
|  |  |  | 9:79312579 | rs684639 | 44.35% (T) | A | T |  |  |
|  |  |  | 9:79312627 | rs685011 | 44.35% (G) | C | G |  |  |
|  |  |  | 9:79312642 | rs12346312 | 5.45% (A) | G | A |  |  |
| Chr17:55225 | 17:14755225-14755669 | 444 | 17:14755298 | NSV |  | C | A | CTGCTTGGTATGCC GTCATACCTTTGCT | CCCAAACTCTGTCC GGTAATAATTTCCA |
|  |  |  | 17:14755310 | rs11652535 | 38.34% (G) | A | G |  |  |
|  |  |  | 17:14755323 | rs73266033 | 17.07% (T) | C | T |  |  |
|  |  |  | 17:14755471 | rs72211522 | 33.77% (T) | C | T |  |  |
|  |  |  | 17:14755492 | rs11652696 | 33.77% (A) | G | A |  |  |
|  |  |  | 17:14755582 | NSV |  | C | A |  |  |

Fig. 7H

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| RPA3-AS1 | 7:7856490-7856938 | 448 | 7:7856573 | NSV | | G | A | TAGCCCTTAATGCC CAGTCCTACTTTCAT TC | AATGATGAGTCAAC CCGAATCCCCACTT CA |
| | | | 7:7856659 | NSV | | C | A | | |
| | | | 7:7856669 | rs6956438 | 21.79% (G) | G | A | | |
| | | | 7:7856715 | NSV | | T | C | | |
| | | | 7:7856810 | rs6943254 | 41.83% (T) | T | G | | |
| | | | 7:7856830 | NSV | | T | C | | |
| | | | 7:7856853 | rs6957893 | 31.93% (G) | C | G | | |
| | | | 7:7856893 | rs6957911 | 11.98% (C) | C | G | | |
| | | | 7:7856893 | rs386709970 | ? | CT | GC | | |
| | | | 7:7856894 | rs6943429 | 45.69% (T) | T | C | | |
| TMEM64 | 8:91777679-91778023 | 344 | 8:91777733 | NSV | | A | G | AGTTACCATGACTTG GCCGAAGACTATGA TTG | CCAGGCATCATACT TGGTACACCATGCA TAG |
| | | | 8:91777808 | rs16905310 | 8.35% (G) | A | G | | |
| | | | 8:91777822 | NSV | | G | A | | |
| | | | 8:91777848 | rs12542205 | 43.39% (A) | A | G | | |
| | | | 8:91777905 | rs12544556 | 43.73% (G) | G | A | | |
| | | | 8:91777932 | rs12542223 | 43.39% (A) | A | G | | |
| | | | 8:91777937 | rs116966974 | 1.76% (T) | C | T | | |
| | | | 8:91777948 | rs132655863 | 43.35% (A) | A | G | | |
| | | | 8:91777978 | rs12542788 | 43.43% (T) | T | G | | |
| LUC7L2 | 7:139079073-139079540 | 467 | 7:139079207 | rs7795520 | 41.45% (G) | A | G | AGTGAGTTAATCTTA CCCCTCTCATGCAT C | TACCATGCTAGTTCC GGTTATTTCAGTAC |
| | | | 7:139079385 | rs6467846 | 41.43% (T) | G | T | | |
| | | | 7:139079436 | rs6467847 | 39.00% (C) | T | C | | |
| LRFN2 | 6:40527450-40527803 | 353 | 6:40527521 | rs1771302 | 7.51% (G) | A | G | CTGGGCATGTCCTA CCCTAGCTGCCTAC T | CACCCAGGGCTAAC CGAGACAATGCAGA |
| | | | 6:40527525 | rs1737679 | 40.62% (G) | G | A | | |
| | | | 6:40527634 | rs846505 | 44.37% (A) | A | C | | |
| | | | 6:40527687 | NSV | | C | A | | |
| | | | 6:40527703 | rs117757640 | 46.41% (T) | C | T | | |

Fig. 7I

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| CCL28 | 5:43367913-43368327 | 414 | 5:43368066 | rs10512827 | 43.33% (G) | A | G | TGGCTATCTTGCCC GCAACTACCAATGT ATGT | GTTGCAACTACCAG CCTACCATACCAGA |
| | | | 5:43368162 | rs12517362 | 43.25% (T) | C | T | | |
| | | | 5:43368290 | rs10512828 | 42.75% (C) | T | C | | |
| Chr16:03046 | 16:5903046-5903508 | 462 | 16:5903190 | rs7204977 | 36.98% (G) | T | G | ATATGTTTACAGATC AGACTAGCCCTAGG | CTGGATGGTCCAGC GATTAGATTACCTG |
| | | | 16:5903294 | rs34376349 | 38.96% (A) | G | A | | |
| | | | 16:5903304 | rs11643091 | 12.98% (G) | A | G | | |
| | | | 16:5903317 | rs7200256 | 28.55% (G) | A | G | | |
| | | | 16:5903353 | rs4238867 | 46.61% (T) | G | T | | |
| RP11 | X:80722641-80722979 | 338 | X:80722669 | NSV | | C | T | TACTTGGTAGATGG GTGAGTTTGATAGA CAT | CTTGCCCTTAGGGG CTCTATATAAGCCTG C |
| | | | X:80722677 | NSV | | C | T | | |
| | | | X:80722679 | NSV | | C | T | | |
| | | | X:80722680 | NSV | | C | T | | |
| | | | X:80722700 | NSV | | C | T | | |
| | | | X:80722701 | NSV | | C | T | | |
| | | | X:80722706 | NSV | | C | T | | |
| | | | X:80722707 | NSV | | C | T | | |
| | | | X:80722714 | NSV | | C | T | | |
| | | | X:80722715 | NSV | | C | T | | |
| | | | X:80722722 | NSV | | C | T | | |
| | | | X:80722725 | NSV | | C | T | | |
| | | | X:80722728 | NSV | | C | T | | |
| | | | X:80722730 | rs28066667 | 44.74% (A) | G | A | | |
| | | | X:80722736 | NSV | | C | T | | |
| | | | X:80722738 | NSV | | C | T | | |
| | | | X:80722743 | NSV | | C | T | | |
| | | | X:80722753 | NSV | | C | T | | |
| | | | X:80722782 | NSV | | C | T | | |

Fig. 7J

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| | | | X:80722785 | NSV | | C | T | | |
| | | | X:80722786 | NSV | | C | T | | |
| | | | X:80722788 | rs2602614 | 43.71% (G) | T | G | | |
| | | | X:80722829 | NSV | | C | T | | |
| | | | X:80722839 | NSV | | C | T | | |
| | | | X:80722848 | NSV | | C | T | | |
| | | | X:80722864 | NSV | | C | T | | |
| | | | X:80722875 | NSV | | C | T | | |
| | | | X:80722876 | NSV | | C | T | | |
| | | | X:80722878 | rs1377509 | 44.74% (G) | T | G | | |
| | | | X:80722879 | NSV | | C | T | | |
| | | | X:80722937 | rs1377510 | 44.74% (A) | T | A | | |
| | | | X:80722974 | NSV | | G | A | | |
| RP11-84D1 | 1:253343997-253344354 | 357 | 1:253344070 | rs109903124 | 46.63% (C) | T | C | | |
| | | | 1:253344122 | rs109903125 | 46.67% (G) | A | G | GCCAGCCTGACGG GTCAGAGTGTCATC CCGCATTGGTT | TAGGAAACTTACGA GGCCCCTTGGCTAG GATGCGGCCCCA |
| | | | 1:253344155 | rs109903126 | 46.71% (G) | A | G | | |
| | | | 1:253344196 | rs109903127 | 45.71% (A) | G | A | | |
| | | | 1:253344265 | rs11249241 | 45.71% (T) | C | T | | |

Fig. 7K

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| PLEKHA6 | 1:204285524-204286080 | 556 | 1:204285669 | rs137934729 | 0.54% (A) | G | A | AGCTGCAGGCCGCT CAGAATAGGGACAC GGGAGAAATGCTTT | GTTTAAGGAGTGGA TACGAGGAGGCCGC TTTATCTGTCTG |
| | | | 1:204285706 | rs4586035 | 44.49% (A) | G | A | | |
| | | | 1:204285759 | rs4558047 | 44.47% (A) | G | A | | |
| | | | 1:204285934 | rs4433462 | 44.47% (T) | C | T | | |
| | | | 1:204286030 | rs4314945 | 44.55% (G) | A | G | | |
| | | | 1:204286046 | rs4313451 | 33.45% (A) | A | G | | |
| | | | 1:204286046 | rs386638661 | ? | AGA | GGG | | |
| | | | 1:204286048 | rs4313452 | 44.59% (G) | A | G | | |
| | | | 1:204286048 | rs386638661 | ? | AGA | GGG | | |
| | | | 1:204286061 | rs6692858 | 33.47% (C) | C | T | | |
| AGT | 1:230843366-230843888 | 522 | 1:230843438 | rs3789666 | 32.59% (C) | G | C | GGTTCCCCTTGCAC GTTCCCTGCAGGGA CCTCGGTGCT | CCTAACTTTGCTGG CCTCAGTTTCCGTC AAAGGAGGCA |
| | | | 1:230843446 | rs3789667 | 32.05% (A) | G | A | | |
| | | | 1:230843505 | rs2493131 | 4.77% (T) | C | T | | |
| | | | 1:230843557 | rs2493132 | 48.84% (T) | T | C | | |
| | | | 1:230843633 | rs3789669 | 34.35% (G) | A | G | | |
| | | | 1:230843714 | rs3789670 | 18.03% (T) | C | T | | |
| | | | 1:230843800 | rs3789671 | 34.31% (T) | G | T | | |

Fig. 7L

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| ADI1 | 2:3507764-3508263 | 499 | 2:3507914 | rs11127434 | 47.34% (A) | A | G | CAGGAATCATCACGACTTACGAAAAACGTTGAGTGAAAGTT | GTGGATGTAAATGGTGTGACTCTGACGTGGAAGTTGAGA |
| | | | 2:3507914 | rs71396997 | ? | AT | GC | | |
| | | | 2:3507915 | rs11891087 | 47.34% (T) | T | C | | |
| | | | 2:3507915 | rs71396997 | ? | AT | GC | | |
| | | | 2:3507931 | rs11127435 | 47.36% (T) | T | C | | |
| | | | 2:3507931 | rs386642521 | ? | TTGACCTGACATCAGATCAGCAGT | CAGC | | |
| | | | 2:3507944 | rs11127436 | 44.21% (T) | T | C | | |
| | | | 2:3507944 | rs386642521 | ? | TTGACCTGACATCAGATCAGCAGT | CAGC | | |
| | | | 2:3508131 | rs11680305 | 44.37% (A) | A | G | | |
| RN7SL63P | 2:65785838-65786166 | 328 | 2:65785911 | rs75598635 | 49.64% (G) | G | A | CTTGAATCAGCAACGTCAGCATCACCGGTGGAGTTGTT | ACCAACAGGTTCAATTGCCAGATGACAGACGCTGTCTGTT |
| | | | 2:65785962 | rs16411469 | 48.78% (A) | G | A | | |
| | | | 2:65786067 | rs75598574 | 49.76% (C) | C | T | | |
| | | | 2:65786077 | rs7601221 | 49.76% (C) | C | T | | |
| | | | 2:65786092 | rs7601228 | 49.70% (C) | C | G | | |
| | | | 2:65786113 | NSV | ? | G | A | | |
| | | | 2:65786144 | rs1420350 | 48.86% (T) | A | T | | |
| | | | 2:65786161 | rs7601422 | 49.72% (G) | G | C | | |
| RP3-468B3 | 6:33917373-33917905 | 532 | 6:33917462 | rs2499746 | 39.06% (T) | C | T | GTCACATTGATGAGTAAACCCTCCTGTCGGAATCTGAAAGCC | AGGTATGGCCTCGGGTTCGAGGGGCTGCGGCGGGAAGCTC |
| | | | 6:33917641 | rs2495959 | ? | A | G | | |
| | | | 6:33917666 | rs9394181 | 43.17% (T) | G | T | | |
| | | | 6:33917711 | rs109474691 | 47.74% (A) | G | A | | |
| | | | 6:33917860 | rs9296104 | 48.46% (A) | A | G | | |

Fig. 7M

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| RP11-89M16 | 8:129449870-129450320 | 450 | 8:129449877 | rs10099804 | 31.75% (T) | T | C | | |
| | | | 8:129449877 | rs386729892 | ? | TCTTACAC | CCTTACAT | | |
| | | | 8:129449884 | rs10112885 | 32.11% (C) | C | T | | |
| | | | 8:129449884 | rs386729892 | ? | TCTTACAC | CCTTACAT | TGGAAGCTCTTACACGGTCATTTGAGATAGCAGTCATC | ATTGCCTCTTATGGGTGAGATAATGTGTTACGTGTTTCAC |
| | | | 8:129449908 | NSV | | A | T | | |
| | | | 8:129449914 | NSV | | C | T | | |
| | | | 8:129450151 | NSV | | A | G | | |
| | | | 8:129450156 | rs4733608 | 39.58% (T) | C | T | | |
| | | | 8:129450163 | rs4733609 | 31.53% (G) | G | A | | |
| | | | 8:129450225 | rs4733610 | 49.54% (G) | G | T | | |
| RN7SKP143 | 10:91965949-91966304 | 355 | 10:91965987 | rs2480266 | 31.95% (G) | A | G | | |
| | | | 10:91966084 | rs2478077 | 32.15% (T) | T | C | ATGAAATGGCATCCGATCCACAAGGTAATGTATGGGGTAG | ACAAACGCAACATAAAGGCAAAATCGTATACATTGTTT |
| | | | 10:91966105 | rs2478078 | 32.61% (T) | T | C | | |
| | | | 10:91966211 | rs2249784 | 30.93% (G) | G | A | | |
| | | | 10:91966298 | rs2249781 | 30.91% (C) | C | A | | |
| ANO2 | 12:5790081-5790404 | 323 | 12:5790112 | rs10849323 | 49.58% (T) | T | C | | |
| | | | 12:5790119 | rs10774361 | 48.48% (A) | G | A | | |
| | | | 12:5790164 | rs73111472 | 14.82% (G) | A | G | TATAAGAACCAGCCTCTGCATGACAGACCTGTTGTACAGGG | ATCAGATGGCGGGCAAGCTGTTTCGGCCCAGACTTTC |
| | | | 12:5790185 | rs10735052 | 48.52% (C) | T | C | | |
| | | | 12:5790195 | rs10744688 | 48.52% (C) | T | C | | |
| | | | 12:5790263 | rs10744689 | 48.44% (A) | C | A | | |

Fig. 7N

| Target Name | SNP Island Genomic Range | SNP Island Size (bp) | Identity-Linked SNP Genomic Location | SNP Locus | Global Allele Frequency | Ref | Var | Forward Primer | Reverse Primer |
|---|---|---|---|---|---|---|---|---|---|
| OSBP2 | 22:31256275-31256837 | 562 | 22:31256367 | rs81424410 | 31.49% (A) | G | A | | |
| | | | 22:31256450 | rs178820330 | 15.14% (G) | C | G | | |
| | | | 22:31256498 | rs5753351 | 39.98% (G) | A | G | | |
| | | | 22:31256584 | rs4577391 | 16.51% (A) | A | G | GGGTTGGGGTTTAG AGTGAGCCCTAGAC AAGAGGAGGCTCTT | TGCTCCAATTCTGG CAACCGCCATGATG CTAAAGATGGCCT |
| | | | 22:31256605 | rs130566704 | 8.81% (T) | C | T | | |
| | | | 22:31256668 | rs5749180 | 39.50% (A) | G | A | | |
| | | | 22:31256713 | rs5753352 | 16.73% (C) | C | T | | |
| | | | 22:31256733 | rs5997791 | 31.63% (C) | C | A | | |
| | | | 22:31256766 | rs5997792 | 31.49% (T) | G | T | | |
| | | | 22:31256767 | rs5749181 | 48.62% (C) | T | C | | |
| Chr8:8340 | 8:123608340-123608909 | 569 | 8:129449884 | rs10112885 | 32.11% (C) | C | T | CATGGGAATGAACC CAATCAGTATCAAC | ACCAGTGACCAAAC GATGCATATGACCC |
| | | | 8:129449884 | rs386729892 | ? | TCTTACCTTA CAC CAT | | | |
| | | | 8:129449877 | rs100999804 | 31.75% (T) | T | C | | |
| | | | 8:129449877 | rs386729892 | ? | TCTTACCTTA CAC CAT | | | |
| SPOCK1 | 5:136605463-136605587 | 124 | 5:136605483 | rs2060427 | 47.40% (C) | A | C | TTCATCCCTGAGAC CCACTTAACGATTG GGG | ACCTGAGTCTTAGG CCCTGGTGAAATGC C |
| | | | 5:136605516 | rs2060428 | 38.56% (T) | T | C | | |
| ADAMTS2 | 5:178690676-178690854 | 178 | 5:178690725 | rs338882 | 45.61% (G) | G | A | CTGAGAGACATCCC AGCCGAAGAATCCA GC | CTGAAGGAGCTCTG AGCGGGAAAGGTC |
| | | | 5:178690776 | rs42875 | 12.68% (G) | A | G | | |
| CUBN | 10:170064951-170065145 | 194 | 10:170064992 | rs7897550 | 25.86% (A) | G | A | CTCGATGTGTCTTAC GGAATACTAGGTCG CAGC | GGGGTCTCCTTCAA TGCGTAATCCCATC CAG |
| | | | 10:170065041 | rs1160048141 | 0.32% (T) | C | T | | |
| | | | 10:170065067 | rs39202042 | 32.65% (T) | T | C | | |
| VAT1L | 16:78016923-78017135 | 212 | 16:78017034 | rs4409820 | 35.18% (A) | C | A | GGAAGACAGGCACT ATGGGAAGTCAGCA CC | AGTCAAGGCATTTG ACCATCTGGCTCCT GG |
| | | | 16:78017045 | rs430044 | 35.18% (T) | C | T | | |
| | | | 16:78017051 | rs430046 | 35.10% (T) | C | T | | |
| | | | 16:78017077 | rs381840 | 1.32% (A) | A | G | | |
| | | | 16:78017096 | NSV | | C | A | | |

|      | ID1  | ID2  | ID3  | ID4  | ID5  | ID6  | ID7  | ID8  | ID9  | ID10 | ID11 | ID12 | ID13 | ID14 | ID15 |
| ---- | ---- | ---- | ---- | ---- | ---- | ---- | ---- | ---- | ---- | ---- | ---- | ---- | ---- | ---- | ---- |
| ID1  | —    | 72   | 62   | 69   | 47   | 78   | 61   | 59   | 70   | 59   | 62   | 72   | 52   | 46   | 63   |
| ID2  | 0.62 | —    | 66   | 60   | 51   | 71   | 59   | 46   | 56   | 57   | 60   | 54   | 55   | 51   | 69   |
| ID3  | 0.53 | 0.57 | —    | 48   | 54   | 70   | 60   | 56   | 61   | 95   | 62   | 58   | 50   | 51   | 58   |
| ID4  | 0.59 | 0.52 | 0.41 | —    | 70   | 68   | 51   | 59   | 60   | 53   | 55   | 70   | 55   | 49   | 50   |
| ID5  | 0.41 | 0.44 | 0.47 | 0.60 | —    | 64   | 58   | 61   | 63   | 59   | 52   | 56   | 61   | 41   | 58   |
| ID6  | 0.67 | 0.61 | 0.60 | 0.59 | 0.55 | —    | 66   | 64   | 62   | 58   | 57   | 66   | 52   | 45   | 60   |
| ID7  | 0.53 | 0.51 | 0.52 | 0.44 | 0.50 | 0.57 | —    | 61   | 50   | 62   | 66   | 50   | 64   | 48   | 49   |
| ID8  | 0.51 | 0.40 | 0.48 | 0.51 | 0.53 | 0.55 | 0.53 | —    | 54   | 52   | 54   | 47   | 43   | 43   | 44   |
| ID9  | 0.60 | 0.48 | 0.53 | 0.52 | 0.54 | 0.53 | 0.43 | 0.47 | —    | 61   | 67   | 52   | 47   | 48   | 62   |
| ID10 | 0.51 | 0.49 | 0.82 | 0.46 | 0.51 | 0.48 | 0.53 | 0.45 | 0.53 | —    | 63   | 67   | 53   | 47   | 59   |
| ID11 | 0.53 | 0.52 | 0.53 | 0.47 | 0.45 | 0.49 | 0.57 | 0.47 | 0.58 | 0.54 | —    | 63   | 51   | 62   | 61   |
| ID12 | 0.62 | 0.47 | 0.50 | 0.60 | 0.48 | 0.57 | 0.43 | 0.41 | 0.45 | 0.58 | 0.54 | —    | 53   | 42   | 66   |
| ID13 | 0.45 | 0.47 | 0.43 | 0.47 | 0.53 | 0.45 | 0.55 | 0.37 | 0.41 | 0.46 | 0.44 | 0.46 | —    | 48   | 48   |
| ID14 | 0.40 | 0.44 | 0.44 | 0.42 | 0.35 | 0.39 | 0.41 | 0.37 | 0.41 | 0.41 | 0.53 | 0.36 | 0.41 | —    | 50   |
| ID15 | 0.54 | 0.59 | 0.50 | 0.43 | 0.50 | 0.52 | 0.42 | 0.38 | 0.53 | 0.51 | 0.53 | 0.57 | 0.41 | 0.43 | —    |

Fig. 11

DEVELOPMENT OF SNP ISLANDS AND APPLICATION OF SNP ISLANDS IN GENOMIC ANALYSIS

STATEMENT REGARDING FEDERALLY SPONSORED RESEARCH OR DEVELOPMENT

This invention was made with Government support under U.S. Government contracts HSHQDC-14-J-00054, HSHQDC-15-J-00068, and HSHQDC-16-J-00137 awarded by the U.S. Department of Homeland Security. The Government has certain rights in this invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 699592003900SEQLIST.txt, date recorded: Dec. 19, 2016, size: 22 KB).

FIELD

This relates generally to genomics, and more specifically to techniques for analyzing single nucleotide polymorphisms (SNPs) in nucleic acid sequences.

BACKGROUND

Over evolutionary time, the human population has displayed adaptability to changing conditions and environments. Driven by natural selection, the genetic diversity of the modern human population spans the globe and results in unique, inheritable markers of distinction within the population. These genetic variations result in over 84 million single nucleotide polymorphisms (SNPs), defining the worldwide human populations. These unique patterns of SNP inheritance, governed by factors of genetic heredity, physical isolation, and environmental influences, account for the diverse and unique SNP patterns displayed within the human population and among individuals.

As the utility and strength of SNPs for identity differentiation continues to gain momentum, SNP panels have shown utility for forensic applications. For example, the GenPlex HID System utilizes 48 of the 52-plex SNPforID SNP panel, which has a mean probability match of at least $5.0 \times 10^{-19}$. Kidd et al. reported a panel of 19 unlinked SNPs, a panel of 40 unlinked SNPs, and later an expanded panel of 92 unlinked SNPs for application in forensic individual identification. In the application of massively parallel sequencing (MPS) technologies in forensic sciences, reports have described the Illumina ForenSeq system and the Ion Torrent AmpliSeq HID system for use in human identification and genetic profiling. Each of these use MPS technologies for rapid, targeted resequencing analysis of informative SNPs.

Leveraging advances in MPS and post-sequencing bioinformatics processing technologies, SNPs are characterized within the genome with increasing speed and accuracy. Projects such as the 1000 Genomes Project, International HapMap Project, and the Encyclopedia of DNA Elements (ENCODE) offer necessary and valuable databases with SNP representations from the greater global human population. The 1000 Genomes Project has made available a database containing records of verified SNP locations found in the current version of the human reference genome across about 2,500 complete human genomes, representing approximately 25 populations around the world.

SUMMARY

SNPs have utility for determining identity, ancestry, phenotype, and disease states. As the forensics community pivots to leverage the information contained within these genomic markers, databases with allele frequency data, representing a larger portion of the human population, are required to determine the frequency of the genetic variation across the global human population. Databases like the 1000 Genomes Project SNP Database, the Database of Single Nucleotide Polymorphisms (dbSNP), the International HapMap Project, and the Allele Frequency Database (ALFRED) continue to develop and expand, describing the SNP variations of global populations with greater fidelity. These databases are useful for predicting the application of newly developed SNP panels across a broader subset of the global human population range. The allele frequencies of known and characterized SNPs provide a basis for determining genomic regions with utility for identifying and describing characteristics of individuals, using markers within their genomes. Tailored SNP panels for answering targeted questions can be developed from this data.

There is a need for improved techniques for rapidly and effectively locating SNP islands that are designed for and amenable to analysis by massively parallel sequencing and that provide representation within the human population with a frequency that allows general variability but not niche specificity that would select for a highly specific population. As used herein, the term "SNP islands" may refer to contiguous regions in a nucleic acid sequence having a high number of SNPs, surrounded on both sides by regions having a low number of SNPs. Effectively and accurately locating SNP islands in nucleic acid sequences may enable the rapid development of SNP panels that may be effective for determining markers of disease states, phenotypic traits, ancestry, and individual identity.

Disclosed herein are systems and methods for scanning a reference nucleic acid sequence in order to determine SNP island target regions comprising a high-variance region having clustered and impactful SNPs flanked by low-variance regions having few or no relevant SNPs. Further disclosed herein are systems and methods for filtering SNP island target regions in order to determine whether uniquely-selecting primers may be effectively designed to select for the high-variance regions. Further disclosed herein are systems and methods for distinguishing the identities of various DNA samples (and associated individuals) based on comparing each sample at identity-relevant impactful SNPs located in high-variance regions of SNP islands. Further disclosed herein are methods for determining whether a sample contains DNA from a single contributor or from multiple contributors based on analyzing proportions indicative of sample zygosity at the locations of impactful SNPs located in high-variance regions of SNP islands.

In some embodiments, a first method, for determining a location in a nucleic acid sequence for which to design one or more primers, is provided, the method comprising: at a system comprising a processor and memory storing instructions executable by the processor: receiving information representing a reference nucleic acid sequence, wherein the information indicates the respective locations of a plurality of known single-nucleotide polymorphisms (SNPs) in the sequence; scanning the reference nucleic acid sequence to locate a first region, a second region, and a third region, wherein the second region includes a plurality of impactful SNP locations, and wherein the first and third regions flank the second region; and determining a location within one of the first and third regions for which to design a primer for amplification of a region of the nucleic acid sequence that includes the two of more impactful SNP locations.

In some embodiments of the first method: the method further comprises designing a primer for the determined location.

In some embodiments of the first method: scanning the reference nucleic acid sequence to locate the first region, the second region, and the third region comprises: determining whether a first segment of the reference nucleic acid sequence contains fewer than or equal to a first number of relevant SNP locations; in accordance with a determination that the first segment contains fewer than or equal to the first number of relevant SNP locations, determining whether a second segment of the reference nucleic acid sequence, adjacent to and immediately following the first segment, contains at least a second number of impactful SNP locations; in accordance with a determination that the second segment contains at least the second number of impactful SNP locations, determining whether a third segment of the reference nucleic acid sequence, adjacent to and immediately following the second segment, contains fewer than or equal to a third number of relevant SNP locations; and in accordance with a determination that the third segment contains fewer than or equal to the third number of relevant SNP locations, determining that the first segment is the first region, that the second segment is the second region, that the third segment is the third region.

In some embodiments of the first method: the first segment is at least a first minimum length; the second segment is at most a maximum length; and the third segment is at least a second minimum length.

In some embodiments of the first method: the first segment is at least a first minimum length; the second segment is at most a maximum length; and the third segment is at least the first minimum length.

In some embodiments of the first method: a relevant SNP location is a base in the nucleic acid sequence known to have a SNP occurring in more than a first minimum percentage of a population and less than a first maximum percentage of the population.

In some embodiments of the first method: an impactful SNP location is a base in the nucleic acid sequence known to have a SNP occurring in more than a second minimum percentage of a population and less than a second maximum percentage of the population.

In some embodiments of the first method: an impactful SNP location is a base in the nucleic acid sequence known to have a SNP associated with a phenotype.

In some embodiments of the first method: an impactful SNP location is a base in the nucleic acid sequence known to have a SNP associated with a medical condition.

In some embodiments of the first method: determining a location within one of the first and third regions for which to design a primer comprises: comparing the first and third regions to the remainder of the reference nucleic acid sequence to locate a unique sub-segment in one of the first and third regions, wherein the unique sub-segment has at least a third minimum length and is not replicated elsewhere in the reference nucleic acid sequence; and determining that the unique sub-segment is the location at which to design a primer.

In some embodiments of the first method: determining a location within one of the first and third regions for which to design a primer comprises: determining that the unique sub-segment does not have a similarity above a similarity threshold to any other portion of the remainder of the reference nucleic acid sequence.

In some embodiments of the first method: determining a location within one of the first and third regions for which to design a primer comprises: determining that the first and third regions do not contain more than a fourth number of consecutive identical nucleotides.

In some embodiments of the first method: determining a location within one of the first and third regions for which to design a primer comprises: determining that the first and third regions do not contain one or more predefined patterns.

In some embodiments of the first method: scanning the reference nucleic acid sequence to locate the first region, the second region, and the third region comprises: determining whether a first segment of the reference nucleic acid sequence contains fewer than or equal to a first number of relevant SNP locations; in accordance with a determination that the first segment contains fewer than or equal to the number of relevant SNPs, determining whether a second segment of the reference nucleic acid sequence, adjacent to and immediately following the first segment, contains at least a second number of impactful SNP locations; in accordance with a determination that the second segment contains at least the second number of impactful SNP locations, determining whether a third segment of the reference nucleic acid sequence, adjacent to and immediately following the second segment, contains fewer than or equal to a third number of relevant SNP locations; and in accordance with a determination that the third segment does not contain fewer than or equal to greater than the third number of relevant SNP locations: determining whether a fourth segment of the reference nucleic acid sequence, following but not immediately adjacent to the second segment, contains fewer than or equal to a third number of relevant SNP locations; and in accordance with a determination that the fourth segment contains fewer than or equal to the third number of relevant SNP locations, determining that the first segment is the first region, that the third segment is the third region, and that a fifth segment spanning from the beginning of the second segment to immediately before the beginning of the fourth segment is the second region.

In some embodiments, a first system, for determining a location in a nucleic acid sequence for which to design one or more primers, is provided, the system comprising: a processor; and memory. In some embodiments of the first system, the memory stores instructions that, when executed by the processor, cause the system to: receive information representing a reference nucleic acid sequence, wherein the information indicates the respective locations of a plurality of known single-nucleotide polymorphisms (SNPs) in the sequence; scan the reference nucleic acid sequence to locate a first region, a second region, and a third region, wherein the second region includes a plurality of impactful SNP locations, and wherein the first and third regions flank the second region; and determine a location within one of the first and third regions for which to design a primer for amplification of a region of the nucleic acid sequence that includes the two of more impactful SNP locations.

In some embodiments of the first system: the instructions further cause the system to design a primer for the determined location.

In some embodiments of the first system: scanning the reference nucleic acid sequence to locate the first region, the second region, and the third region comprises: determining whether a first segment of the reference nucleic acid sequence contains fewer than or equal to a first number of relevant SNP locations; in accordance with a determination that the first segment contains fewer than or equal to the first number of relevant SNP locations, determining whether a second segment of the reference nucleic acid sequence, adjacent to and immediately following the first segment, contains at least a second number of impactful SNP locations; in accordance with a determination that the second segment contains at least the second number of impactful SNP locations, determining whether a third segment of the reference nucleic acid sequence, adjacent to and immediately following the second segment, contains fewer than or equal to a third number of relevant SNP locations; and in accordance with a determination that the third segment contains fewer than or equal to the third number of relevant SNP locations, determining that the first segment is the first region, that the second segment is the second region, that the third segment is the third region.

In some embodiments of the first system: the first segment is at least a first minimum length; the second segment is at most a maximum length; and the third segment is at least a second minimum length.

In some embodiments of the first system: the first segment is at least a first minimum length; the second segment is at most a maximum length; and the third segment is at least the first minimum length.

In some embodiments of the first system: a relevant SNP location is a base in the nucleic acid sequence known to have a SNP occurring in more than a first minimum and less than a first maximum percentage of the population In some embodiments of the first system: an impactful SNP location is a base in the nucleic acid sequence known to have a SNP occurring in more than a second minimum percentage of a population and less than a second maximum percentage of the population.

In some embodiments of the first system: an impactful SNP location is a base in the nucleic acid sequence known to have a SNP associated with a phenotype.

In some embodiments of the first system: an impactful SNP location is a base in the nucleic acid sequence known to have a SNP associated with a medical condition.

In some embodiments of the first system: determining a location within one of the first and third regions for which to design a primer comprises: comparing the first and third regions to the remainder of the reference nucleic acid sequence to locate a unique sub-segment in one of the first and third regions, wherein the unique sub-segment has at least a third minimum length and is not replicated elsewhere in the reference nucleic acid sequence; and determining that the unique sub-segment is the location at which to design a primer.

In some embodiments of the first system: determining a location within one of the first and third regions for which to design a primer comprises: determining that the unique sub-segment does not have a similarity above a similarity threshold to any other portion of the remainder of the reference nucleic acid sequence.

In some embodiments of the first system: determining a location within one of the first and third regions for which to design a primer comprises: determining that the first and third regions do not contain more than a fourth number of consecutive identical nucleotides.

In some embodiments of the first system: determining a location within one of the first and third regions for which to design a primer comprises: determining that the first and third regions do not contain one or more predefined patterns.

In some embodiments of the first system: scanning the reference nucleic acid sequence to locate the first region, the second region, and the third region comprises: determining whether a first segment of the reference nucleic acid sequence contains fewer than or equal to a first number of relevant SNP locations; in accordance with a determination that the first segment contains fewer than or equal to the number of relevant SNPs, determining whether a second segment of the reference nucleic acid sequence, adjacent to and immediately following the first segment, contains at least a second number of impactful SNP locations; in accordance with a determination that the second segment contains at least the second number of impactful SNP locations, determining whether a third segment of the reference nucleic acid sequence, adjacent to and immediately following the second segment, contains fewer than or equal to a third number of relevant SNP locations; and in accordance with a determination that the third segment does not contain fewer than or equal to greater than the third number of relevant SNP locations: determining whether a fourth segment of the reference nucleic acid sequence, following but not immediately adjacent to the second segment, contains fewer than or equal to a third number of relevant SNP locations; and in accordance with a determination that the fourth segment contains fewer than or equal to the third number of relevant SNP locations, determining that the first segment is the first region, that the third segment is the third region, and that a fifth segment spanning from the beginning of the second segment to immediately before the beginning of the fourth segment is the second region.

In some embodiments, a first non-transitory computer readable storage medium is provided. In some embodiments, the first non-transitory computer readable storage medium stores instructions that, when executed by a system comprising a processor, cause the system to: receive information representing a reference nucleic acid sequence, wherein the information indicates the respective locations of a plurality of known single-nucleotide polymorphisms (SNPs) in the sequence; scan the reference nucleic acid sequence to locate a first region, a second region, and a third region, wherein the second region includes a plurality of impactful SNP locations, and wherein the first and third regions flank the second region; and determine a location within one of the first and third regions for which to design a primer for amplification of a region of the nucleic acid sequence that includes the two of more impactful SNP locations.

In some embodiments of the first non-transitory computer readable storage medium: the instructions further cause the system to design a primer for the determined location.

In some embodiments of the first non-transitory computer readable storage medium: scanning the reference nucleic acid sequence to locate the first region, the second region, and the third region comprises: determining whether a first segment of the reference nucleic acid sequence contains fewer than or equal to a first number of relevant SNP locations; in accordance with a determination that the first segment contains fewer than or equal to the first number of relevant SNP locations, determining whether a second segment of the reference nucleic acid sequence, adjacent to and immediately following the first segment, contains at least a second number of impactful SNP locations; in accordance with a determination that the second segment contains at least the second number of impactful SNP locations, determining whether a third segment of the reference nucleic acid sequence, adjacent to and immediately following the second segment, contains fewer than or equal to a third number of relevant SNP locations; and in accordance with a determination that the third segment contains fewer than or equal to the third number of relevant SNP locations, determining that the first segment is the first region, that the second segment is the second region, that the third segment is the third region.

In some embodiments of the first non-transitory computer readable storage medium: the first segment is at least a first minimum length; the second segment is at most a maximum length; and the third segment is at least a second minimum length.

In some embodiments of the first non-transitory computer readable storage medium: the first segment is at least a first minimum length; the second segment is at most a maximum length; and the third segment is at least the first minimum length.

In some embodiments of the first non-transitory computer readable storage medium: a relevant SNP location is a base in the nucleic acid sequence known to have a SNP occurring in more than a first minimum and less than a first maximum percentage of the population In some embodiments of the first non-transitory computer readable storage medium: an impactful SNP location is a base in the nucleic acid sequence known to have a SNP occurring in more than a second minimum percentage of a population and less than a second maximum percentage of the population.

In some embodiments of the first non-transitory computer readable storage medium: an impactful SNP location is a base in the nucleic acid sequence known to have a SNP associated with a phenotype.

In some embodiments of the first non-transitory computer readable storage medium: an impactful SNP location is a base in the nucleic acid sequence known to have a SNP associated with a medical condition.

In some embodiments of the first non-transitory computer readable storage medium: determining a location within one of the first and third regions for which to design a primer comprises: comparing the first and third regions to the remainder of the reference nucleic acid sequence to locate a unique sub-segment in one of the first and third regions, wherein the unique sub-segment has at least a third minimum length and is not replicated elsewhere in the reference nucleic acid sequence; and determining that the unique sub-segment is the location at which to design a primer.

In some embodiments of the first non-transitory computer readable storage medium: determining a location within one of the first and third regions for which to design a primer comprises: determining that the unique sub-segment does not have a similarity above a similarity threshold to any other portion of the remainder of the reference nucleic acid sequence.

In some embodiments of the first non-transitory computer readable storage medium: determining a location within one of the first and third regions for which to design a primer comprises: determining that the first and third regions do not contain more than a fourth number of consecutive identical nucleotides.

In some embodiments of the first non-transitory computer readable storage medium: determining a location within one of the first and third regions for which to design a primer comprises: determining that the first and third regions do not contain one or more predefined patterns.

In some embodiments of the first non-transitory computer readable storage medium: scanning the reference nucleic acid sequence to locate the first region, the second region, and the third region comprises: determining whether a first segment of the reference nucleic acid sequence contains fewer than or equal to a first number of relevant SNP locations; in accordance with a determination that the first segment contains fewer than or equal to the number of relevant SNPs, determining whether a second segment of the reference nucleic acid sequence, adjacent to and immediately following the first segment, contains at least a second number of impactful SNP locations; in accordance with a determination that the second segment contains at least the second number of impactful SNP locations, determining whether a third segment of the reference nucleic acid sequence, adjacent to and immediately following the second segment, contains fewer than or equal to a third number of relevant SNP locations; and in accordance with a determination that the third segment does not contain fewer than or equal to greater than the third number of relevant SNP locations: determining whether a fourth segment of the reference nucleic acid sequence, following but not immediately adjacent to the second segment, contains fewer than or equal to a third number of relevant SNP locations; and in accordance with a determination that the fourth segment contains fewer than or equal to the third number of relevant SNP locations, determining that the first segment is the first region, that the third segment is the third region, and that a fifth segment spanning from the beginning of the second segment to immediately before the beginning of the fourth segment is the second region.

In some embodiments, a second method, of distinguishing the identity of genetic material samples, is provided, the method comprising: receiving genetic material samples corresponding to a reference genome; scanning the reference genome to select a location for a primer, the location being located in one of two flanking regions that flank a central region containing a plurality of impactful SNP locations; selecting a primer for the location in the reference genome, wherein the primer is configured to amplify for the plurality of impactful SNP locations located in the central region; amplifying the genetic material samples using the primer; sequencing and align the amplified samples to generate respective data representations of each sample, wherein each data representation includes a respective profile of the plurality of impactful SNP locations in the central region; comparing the profiles of the plurality of impactful SNP locations to isolate a difference between the genetic material samples at one or more of the impactful SNP locations; and storing data representing the isolated difference between the genetic material samples.

In some embodiments of the second method, the second method further comprises calculating and storing a similarity score indicating a similarity of the respective profiles of a first one of the genetic material samples to a second one of the genetic material samples.

In some embodiments, a second system, for determining a location in a nucleic acid sequence for which to design one or more primers, is provided, the system comprising: a processor; and memory. In some embodiments of the second system, the memory stores instructions that, when executed by the processor, cause the system to: receive genetic material samples corresponding to a reference genome; scan the reference genome to select a location for a primer, the location being located in one of two flanking regions that flank a central region containing a plurality of impactful SNP locations; select a primer for the location in the reference genome, wherein the primer is configured to amplify for the plurality of impactful SNP locations located in the central region; amplify the genetic material samples using the primer; sequence and align the amplified samples to generate respective data representations of each sample, wherein each data representation includes a respective profile of the plurality of impactful SNP locations in the central region; compare the profiles of the plurality of impactful SNP locations to isolate a difference between the genetic material samples at one or more of the impactful SNP locations; and store data representing the isolated difference between the genetic material samples.

In some embodiments of the second system, the instructions further cause the system to calculate and store a similarity score indicating a similarity of the respective profiles of a first one of the genetic material samples to a second one of the genetic material samples.

In some embodiments, a second non-transitory computer readable storage medium is provided. In some embodiments, the second non-transitory computer readable storage medium stores instructions that, when executed by a system comprising a processor, cause the system to: receive genetic material samples corresponding to a reference genome; scan the reference genome to select a location for a primer, the location being located in one of two flanking regions that flank a central region containing a plurality of impactful SNP locations; select a primer for the location in the reference genome, wherein the primer is configured to amplify for the plurality of impactful SNP locations located in the central region; amplify the genetic material samples using the primer; sequence and align the amplified samples to generate respective data representations of each sample, wherein each data representation includes a respective profile of the plurality of impactful SNP locations in the central region; compare the profiles of the plurality of impactful SNP locations to isolate a difference between the genetic material samples at one or more of the impactful SNP locations; and store data representing the isolated difference between the genetic material samples.

In some embodiments of the second non-transitory computer readable storage medium, the instructions further cause the system to calculate and store a similarity score indicating a similarity of the respective profiles of a first one of the genetic material samples to a second one of the genetic material samples.

In some embodiments, a third method, of determining whether a genetic material sample corresponds to a single contributor or to multiple contributors, is provided, the third method comprising: receiving a genetic material sample corresponding to a reference genome; scanning the reference genome to select a location for a primer, the location being located in one of two flanking regions that flank a central region containing a plurality of impactful SNP locations; selecting a primer for the location in the reference genome, wherein the primer is configured to amplify for the plurality of impactful SNP locations located in the central region; amplifying the genetic material sample using the primer; sequencing and align the amplified sample to generate a data representation of the sample, wherein the data representation includes a profile of the plurality of SNP locations in the central region; for each of the plurality of impactful SNP locations in the central region, calculating a depth of coverage and a proportion indicative of sample zygosity; if more than a predefined percentage of sample zygosity proportions falls outside one or more predefined proportion ranges, determining that the genetic material sample corresponds to multiple contributors; and if less than a predefined percentage of the sample zygosity proportions falls outside the one or more predefined proportion ranges, determining that the genetic material sample corresponds to a single contributor.

In some embodiments of the third method: the one or more predefined proportion ranges comprise: a first proportion range corresponding to homozygous reference zygosity; a second proportion range corresponding to heterozygous zygosity; and a third proportion range corresponding to homozygous variant zygosity.

In some embodiments, a third system, for determining whether a genetic material sample corresponds to a single contributor or to multiple contributors, is provided, the second system comprising: a processor; and memory. In some embodiments of the second system, the memory stores instructions that, when executed by the processor, cause the system to: receive a genetic material sample corresponding to a reference genome; scan the reference genome to select a location for a primer, the location being located in one of two flanking regions that flank a central region containing a plurality of impactful SNP locations; select a primer for the location in the reference genome, wherein the primer is configured to amplify for the plurality of impactful SNP locations located in the central region; amplify the genetic material sample using the primer; sequence and align the amplified sample to generate a data representation of the sample, wherein the data representation includes a profile of the plurality of SNP locations in the central region; for each of the plurality of impactful SNP locations in the central region, calculate a depth of coverage and a proportion indicative of sample zygosity; if more than a predefined percentage of sample zygosity proportions falls outside one or more predefined proportion ranges, determine that the genetic material sample corresponds to multiple contributors; and if less than a predefined percentage of the sample zygosity proportions falls outside the one or more predefined proportion ranges, determine that the genetic material sample corresponds to a single contributor.

In some embodiments of the third system: the one or more predefined proportion ranges comprise: a first proportion range corresponding to homozygous reference zygosity; a second proportion range corresponding to heterozygous zygosity; and a third proportion range corresponding to homozygous variant zygosity.

In some embodiments, a third non-transitory computer readable storage medium is provided. In some embodiments, the third non-transitory computer readable storage medium stores instructions that, when executed by a system comprising a processor, cause the system to: receive a genetic material sample corresponding to a reference genome; scan the reference genome to select a location for a primer, the location being located in one of two flanking regions that flank a central region containing a plurality of impactful SNP locations; select a primer for the location in the reference genome, wherein the primer is configured to amplify for the plurality of impactful SNP locations located in the central region; amplify the genetic material sample using the primer; sequence and align the amplified sample to generate a data representation of the sample, wherein the data representation includes a profile of the plurality of SNP locations in the central region; for each of the plurality of impactful SNP locations in the central region, calculate a depth of coverage and a proportion indicative of sample zygosity; if more than a predefined percentage of sample zygosity proportions falls outside one or more predefined proportion ranges, determine that the genetic material sample corresponds to multiple contributors; and if less than a predefined percentage of the sample zygosity proportions falls outside the one or more predefined proportion ranges, determine that the genetic material sample corresponds to a single contributor.

In some embodiments of the third non-transitory computer readable storage medium: the one or more predefined proportion ranges comprise: a first proportion range corresponding to homozygous reference zygosity; a second proportion range corresponding to heterozygous zygosity; and a third proportion range corresponding to homozygous variant zygosity.

In some embodiments, any of the first, second, and/or third non-transitory computer readable storage mediums may be alternately implemented as one or more transitory computer readable storage mediums.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 is a table showing identity-linked SNP islands identified within the human genome, in accordance with some embodiments;

FIGS. 7A-7N show a table showing identity-linked SNPs and SNP island genomic locations in the human genome, in accordance with some embodiments;

FIG. 7A Sequences:
LUZP1i: Forward Primer (SEQ ID NO: 1), Reverse Primer (SEQ ID NO: 2)
LUZP1ii: Forward Primer (SEQ ID NO: 3), Reverse Primer (SEQ ID NO: 4)
ERBB4: Forward Primer (SEQ ID NO: 5), Reverse Primer (SEQ ID NO: 6)
Chr3:94373: Forward Primer (SEQ ID NO: 7), Reverse Primer (SEQ ID NO: 8)
FIG. 7B Sequences:
RFTN1: Forward Primer (SEQ ID NO: 9), Reverse Primer (SEQ ID NO: 10)
ARHGEF3: Forward Primer (SEQ ID NO: 11), Reverse Primer (SEQ ID NO: 12)
ROBO2: Forward Primer (SEQ ID NO: 13), Reverse Primer (SEQ ID NO: 14)
Chr3:45339: Forward Primer (SEQ ID NO: 15), Reverse Primer (SEQ ID NO: 16)
FIG. 7C Sequences:
Chr3:45379: Forward Primer (SEQ ID NO: 17), Reverse Primer (SEQ ID NO: 18)
SLC2A9: Forward Primer (SEQ ID NO: 19), Reverse Primer (SEQ ID NO: 20)
ST3GAL1P1: Forward Primer (SEQ ID NO: 21), Reverse Primer (SEQ ID NO: 22)
GRID2: Forward Primer (SEQ ID NO: 23), Reverse Primer (SEQ ID NO: 24)
FIG. 7D Sequences:
Chr4:53970: Forward Primer (SEQ ID NO: 25), Reverse Primer (SEQ ID NO: 26)
MAP3K7: Forward Primer (SEQ ID NO: 27), Reverse Primer (SEQ ID NO: 28)
TNKS: Forward Primer (SEQ ID NO: 29), Reverse Primer (SEQ ID NO: 30)
EYA1: Forward Primer (SEQ ID NO: 31), Reverse Primer (SEQ ID NO: 32)
ANO1: Forward Primer (SEQ ID NO: 33), Reverse Primer (SEQ ID NO: 34)
FIG. 7E Sequences:
OR10G6: Forward Primer (SEQ ID NO: 35), Reverse Primer (SEQ ID NO: 36)
Chr12:53244: Forward Primer (SEQ ID NO: 37), Reverse Primer (SEQ ID NO: 38)
HOXC13: Forward Primer (SEQ ID NO: 39), Reverse Primer (SEQ ID NO: 40)
SGCG: Forward Primer (SEQ ID NO: 41), Reverse Primer (SEQ ID NO: 42).
Chr13:46674: Forward Primer (SEQ ID NO: 43), Reverse Primer (SEQ ID NO: 44)
RAD51B: Forward Primer (SEQ ID NO: 45), Reverse Primer (SEQ ID NO: 46)
RBFOX1: Forward Primer (SEQ ID NO: 47), Reverse Primer (SEQ ID NO: 48)
FIG. 7F Sequences:
NUP88: Forward Primer (SEQ ID NO: 49), Reverse Primer (SEQ ID NO: 50)
NSF: Forward Primer (SEQ ID NO: 51), Reverse Primer (SEQ ID NO: 52)
ZADH2: Forward Primer (SEQ ID NO: 53), Reverse Primer (SEQ ID NO: 54)
Chr20:36542: Forward Primer (SEQ ID NO: 55), Reverse Primer (SEQ ID NO: 56)
Chr20:21389: Forward Primer (SEQ ID NO: 57), Reverse Primer (SEQ ID NO: 58)
Chr20:66266: Forward Primer (SEQ ID NO: 59), Reverse Primer (SEQ ID NO: 60)
FIG. 7G Sequences:
RIPK4: Forward Primer (SEQ ID NO: 61), Reverse Primer (SEQ ID NO: 62)
SLC19A1: Forward Primer (SEQ ID NO: 63), Reverse Primer (SEQ ID NO: 64)
SYNE3: Forward Primer (SEQ ID NO: 65), Reverse Primer (SEQ ID NO: 66)
PRUNE2: Forward Primer (SEQ ID NO: 67), Reverse Primer (SEQ ID NO: 68)
Chr17:55225: Forward Primer (SEQ ID NO: 69), Reverse Primer (SEQ ID NO: 70)
FIG. 7H Sequences:
RPA3-AS1: Forward Primer (SEQ ID NO: 71), Reverse Primer (SEQ ID NO: 72)
TMEM64: Forward Primer (SEQ ID NO: 73), Reverse Primer (SEQ ID NO: 74)
LUC7L2: Forward Primer (SEQ ID NO: 75), Reverse Primer (SEQ ID NO: 76)
LRFN2: Forward Primer (SEQ ID NO: 77), Reverse Primer (SEQ ID NO: 78)
FIG. 7I Sequences:
CCL28: Forward Primer (SEQ ID NO: 79), Reverse Primer (SEQ ID NO: 80)
Chr16:03046: Forward Primer (SEQ ID NO: 81), Reverse Primer (SEQ ID NO: 82)
RP11: Forward Primer (SEQ ID NO: 83), Reverse Primer (SEQ ID NO: 84)

FIG. 7J Sequences:
RP11-84D1: Forward Primer (SEQ ID NO: 85), Reverse Primer (SEQ ID NO: 86)
FIG. 7K Sequences:
PLEKHA6: Forward Primer (SEQ ID NO: 87), Reverse Primer (SEQ ID NO: 88)
AGT: Forward Primer (SEQ ID NO: 89), Reverse Primer (SEQ ID NO: 90)
FIG. 7L Sequences:
rs386642521: Ref (SEQ ID NO: 91), Var (SEQ ID NO: 92)
ADI1: Forward Primer (SEQ ID NO: 93), Reverse Primer (SEQ ID NO: 94)
RN7SL63P: Forward Primer (SEQ ID NO: 95), Reverse Primer (SEQ ID NO: 96)
RP3-468B3: Forward Primer (SEQ ID NO: 97), Reverse Primer (SEQ ID NO: 98)
FIG. 7M Sequences:
rs386729892: Ref (SEQ ID NO: 99), Var (SEQ ID NO: 100)
RP11-89M16: Forward Primer (SEQ ID NO: 101), Reverse Primer (SEQ ID NO: 102)
RN7SKP143: Forward Primer (SEQ ID NO: 103), Reverse Primer (SEQ ID NO: 104)
ANO2: Forward Primer (SEQ ID NO: 105), Reverse Primer (SEQ ID NO: 106)
FIG. 7N Sequences:
OSBP2: Forward Primer (SEQ ID NO: 107), Reverse Primer (SEQ ID NO: 108) rs386729892: Ref (SEQ ID NO: 109), Var (SEQ ID NO: 110)
Chr8:8340: Forward Primer (SEQ ID NO: 111), Reverse Primer (SEQ ID NO: 112)
SPOCK1: Forward Primer (SEQ ID NO: 113), Reverse Primer (SEQ ID NO: 114)
ADAMTS2: Forward Primer (SEQ ID NO: 115), Reverse Primer (SEQ ID NO: 116)
CUBN: Forward Primer (SEQ ID NO: 117), Reverse Primer (SEQ ID NO: 118)
VAT1L: Forward Primer (SEQ ID NO: 119), Reverse Primer (SEQ ID NO: 120)

FIG. 11 is a table showing a similarity matrix of SNP data for fifteen evaluated individuals, in accordance with some embodiments;

DETAILED DESCRIPTION

Figure 1:
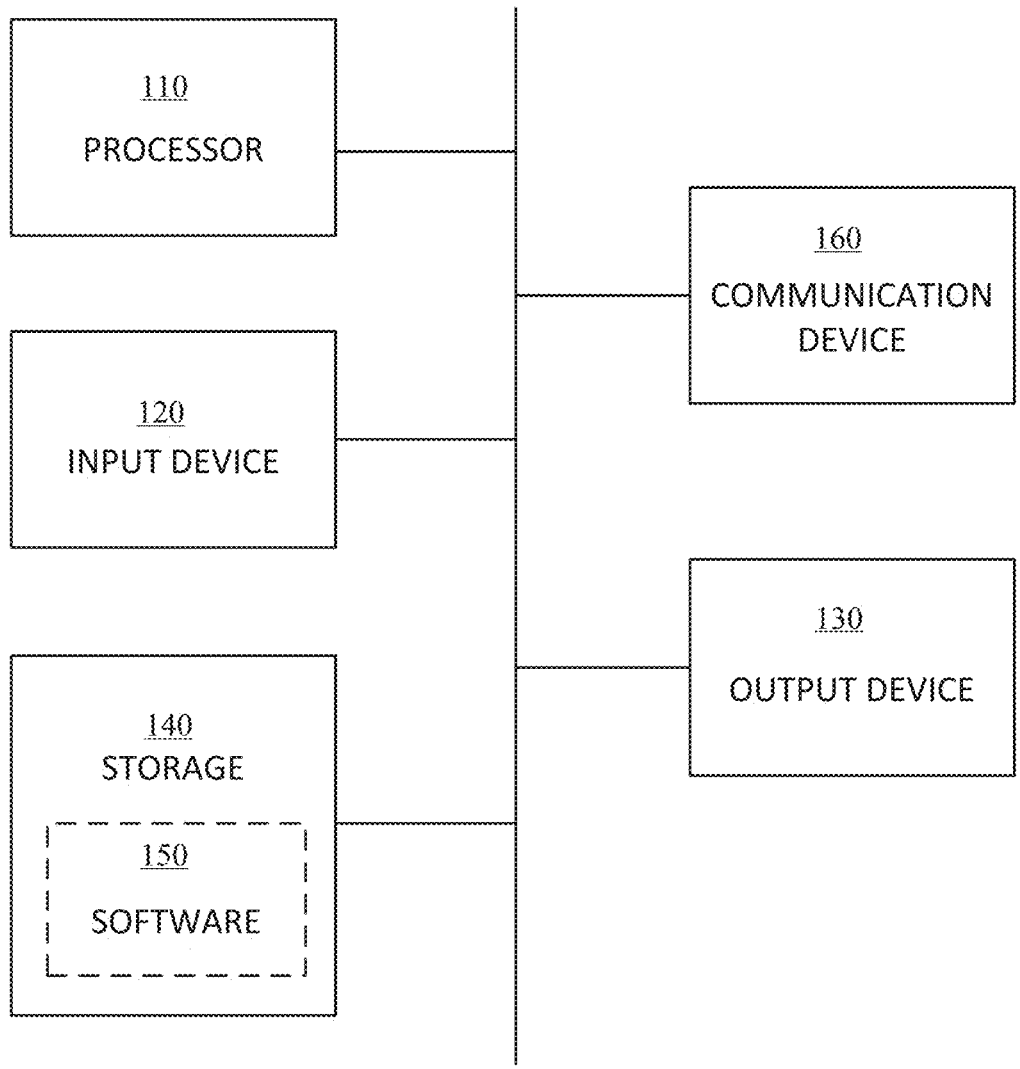
FIG. 1 is a diagram of a computer system that may perform the techniques disclosed herein, in accordance with some embodiments.

Disclosed herein are systems and methods for scanning a reference nucleic acid sequence in order to determine SNP island target regions comprising a high-variance region having clustered impactful SNPs flanked by low-variance regions having few or no relevant SNPs. A high-variance region may alternately be referred to as a central region, while low-variance regions may alternately be referred to as flanking regions. A reference genome may be scanned on a base-by-base, SNP-by-SNP, or sliding-window basis in order to locate a first low-variance region, then locate a high-variance region immediately following the first low-variance region, then locate a second low-variance region immediately following the high-variance region. Systems and methods may enable users to adjust variables for the application of the scanning method, such that the minimum required length of a low-variance region, maximum permissible number of relevant SNPs permitted in a low-variance region, definition of a relevant SNP, maximum permissible length of a high-variance region, minimum required number of impactful SNPs required in a high-variance region, and definition of an impactful SNP may all be adjusted. A scan of a reference genome may yield one or more SNP island target regions as output, which may potentially be used as SNP islands for targeted genomic analysis.

Further disclosed herein are systems and methods for filtering SNP island target regions in order to determine whether uniquely-selecting primers may be effectively designed to select for the high-variance regions. SNP island target regions may be disqualified from designation as viable SNP islands if one or both low-variance regions lack unique stretches of minimum required length as compared to the remainder of the reference genome, if they lack stretches of minimum required length that have no or sufficiently low similarity to the remainder of the reference genome, if they contain stretches of repeat nucleotides for more than a maximum permissible number of bases, or if they contain repeating predefined patterns. Systems and methods may enable users to adjust variables for the application of the filtering method, including adjusting the definitions of and tests for repeating patterns and similarity and including adjusting the base-length thresholds used in determining uniqueness, similarity, repeat-stretches, and repeating patterns. Application of SNP island target region filtering methods may cause certain SNP island target regions to be disqualified as viable SNP islands, while it may allow other SNP island target regions to be validated as viable SNP islands for potential use in targeted genomic analysis.

Further disclosed herein are systems and methods for distinguishing the identities of various DNA samples (and associated individuals) based on comparing each sample at identity-relevant impactful SNPs located in high-variance regions of SNP islands. DNA samples from different contributors may be amplified using primers designed based on SNP islands identified in accordance with the techniques herein. The resulting amplicons (e.g., the amplified samples) may be sequenced and aligned to the reference genome to which the SNP islands correspond, and SNP profiles for each sample may be compared at the impactful SNP locations contained in the SNP islands. Thus, a minimized number of efficient and effective primers may be used to facilitate comparison at a maximized number of identity-relevant and/or otherwise impactful SNP locations. Samples may accordingly be distinguished from one another and/or correlated to other samples corresponding to the same or related DNA.

Further disclosed herein are methods for determining whether a sample contains DNA from a single contributor or from multiple contributors based on analyzing proportions indicative of sample zygosity at the locations of impactful SNPs located in high-variance regions of SNP islands. A DNA sample may be amplified using primers designed based on SNP islands identified in accordance with the techniques herein. The resulting amplicon (e.g., amplified sample) may be sequenced and aligned to the reference genome to which the SNP islands correspond, and depth of coverage and proportion indicative of sample zygosity may be calculated at each impactful SNP location in the SNP islands. The proportion indicative of sample zygosity for all impactful SNP locations in the SNP islands may be analyzed for the sample, and a determination may be made as to whether all or substantially all such proportions indicate one of homozygous reference zygosity, heterozygous zygosity, or homozygous variant zygosity. If it is determined that a substantial portion of proportions for the impactful SNP locations in the SNP islands do not indicate one of homozygous reference zygosity, heterozygous zygosity, or homozygous variant zygosity, then it may be determined that the sample contains DNA from more than one individual. Thus, a minimized number of efficient and effective primers may be used to facilitate creation of sequenced and aligned reads with high depth of coverage for comparison of zygosity types.

In the following description of the disclosure and embodiments, reference is made to the accompanying drawings in which are shown, by way of illustration, specific embodiments that can be practiced. It is to be understood that other embodiments and examples can be practiced and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

Some portions of the detailed description that follows are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic, or optical signals capable of being stored, transferred, combined, compared, and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing," "computing," "calculating," "determining," "displaying," or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by a variety of operating systems.

The present invention also relates to a device for performing the operations herein. This device may be specially constructed for the required purposes, or it may comprise a general-purpose computer selectively activated or reconfigured by a computer program stored in the computer. Such a computer program may be stored in a non-transitory computer readable storage medium, such as, but not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

SNP Island Identification

A method for locating target regions in a nucleic acid sequence may be applied by leveraging known locations of SNPs in the nucleic acid sequence. In some embodiments, the method may be applied to a reference genome, such as a known reference model of genomic sequence. The method may require that locations of SNPs in the sequence be known before the application of the algorithm. For example, the method may be applied using allele frequency variant call files from the 1000 Genomes Project Database to input data about known SNPs in the human genome.

In some embodiments, the method involves progressing along a nucleic acid sequence on a base-by-base or SNP-by-SNP basis, and noting the locations of known SNPs relative to one another. The method may seek to identify, based on the locations of known SNPs, SNP island target regions on the nucleic acid sequence, where the SNP island target regions comprise a high-variance region flanked by low-variance regions. A high-variance region may be defined as a contiguous region in a nucleic acid sequence having at least a predetermined number of known SNPs within a maximum number of contiguous bases. A low-variance region may be defined as a region in a nucleic acid sequence having less than a predetermined number of known SNPs within a predefined number of contiguous bases.

FIG. 1 illustrates an example of a computer in accordance with one embodiment. Computer 100 can be a host computer connected to a network. Computer 100 can be a client computer or a server. As shown in FIG. 1, computer 100 can be any suitable type of microprocessor-based device, such as a personal computer, workstation, server or handheld computing device such as a phone or tablet. The computer can include, for example, one or more of processor 110, input device 120, output device 130, storage 140, and communication device 160. Input device 120 and output device 130 can generally correspond to those described above, and can either be connectable or integrated with the computer.

Input device 120 can be any suitable device that provides input, such as a touch screen or monitor, keyboard, mouse, or voice-recognition device. Output device 130 can be any suitable device that provides output, such as a touch screen, monitor, printer, disk drive, or speaker.

Storage 140 can be any suitable device that provides storage, such as an electrical, magnetic or optical memory including a RAM, cache, hard drive, CD-ROM drive, tape drive or removable storage disk. Communication device 160 can include any suitable device capable of transmitting and receiving signals over a network, such as a network interface chip or card. The components of the computer can be connected in any suitable manner, such as via a physical bus or wirelessly.

Software 150, which can be stored in storage 140 and executed by processor 1310, can include, for example, the programming that embodies the functionality of the present disclosure (e.g., as embodied in the computers, servers and devices as described above). In some embodiments, software 150 can include a combination of servers such as application servers and database servers.

Software 150 can also be stored and/or transported within any computer readable storage medium for use by or in connection with an instruction execution system, apparatus, or device, such as those described above, that can fetch instructions associated with the software from the instruction execution system, apparatus, or device and execute the instructions. In the context of this disclosure, a computer readable storage medium can be any medium, such as storage 140, that can contain or store programming for use by or in connection with an instruction execution system, apparatus, or device.

Software 150 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Computer 100 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 100 can implement any operating system suitable for operating on the network. Software 150 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Locating SNP Island Target Regions

Figure 2:
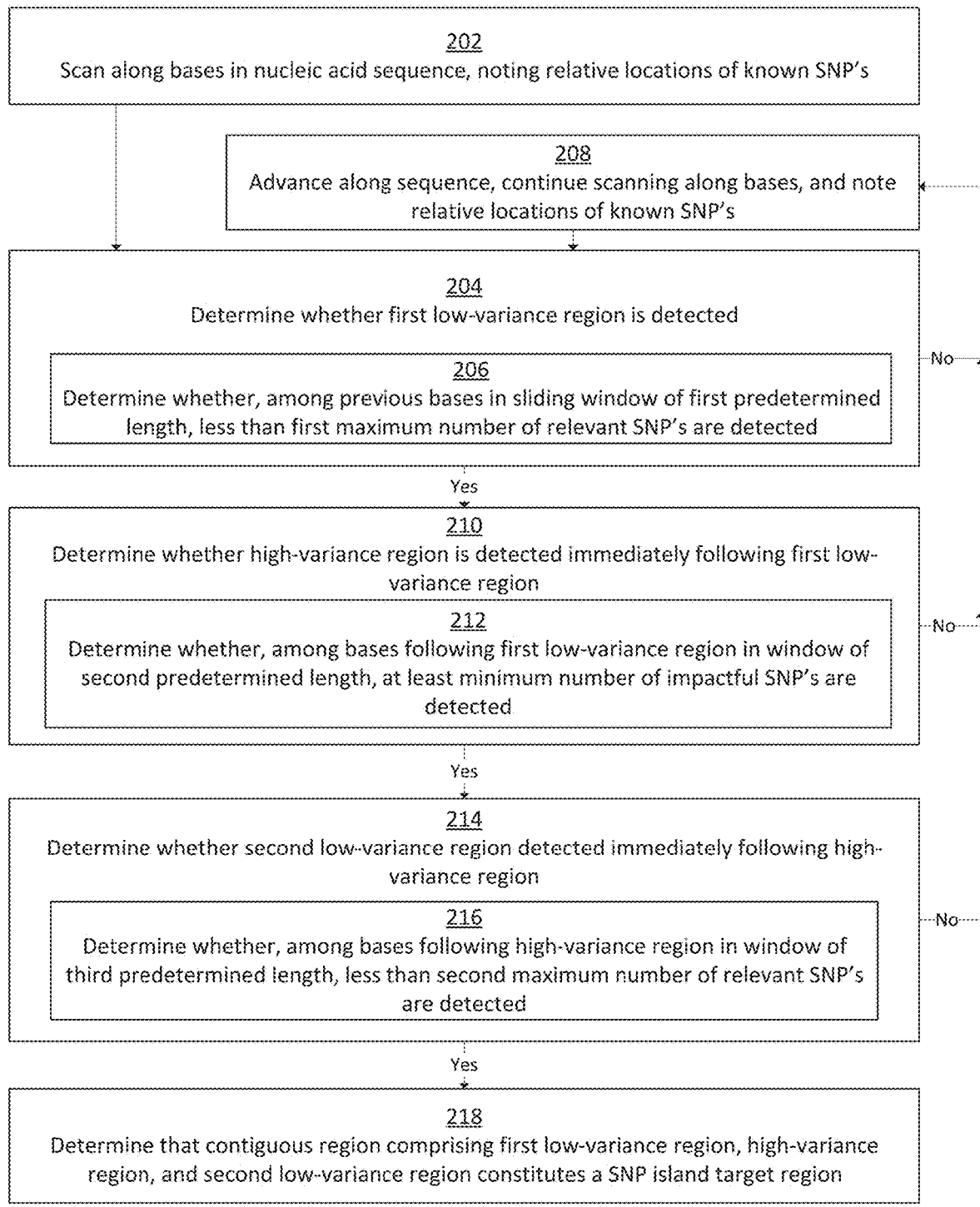
FIG. 2 is a flowchart depicting a method for identifying SNP island target regions in a nucleic acid sequence, in accordance with some embodiments.

FIG. 2 depicts a method for locating SNP island target regions in a nucleic acid sequence such as a known genome, in accordance with some embodiments. The method 200 may be performed by a system such as system 100 described above with reference to FIG. 1. In some embodiments, the method may be executed in whole or in part by a computer processor executing instructions stored in a transitory or non-transitory computer readable medium. In some embodiments, the method may be executed in whole or in part by one or more physical or virtual computer servers located remotely from an end-user, such that a user may access and/or implement the method through the use of a local client device and may cause one or more remote servers to execute the method. In some embodiments, the method may be executed in whole or in part by one or more consumer-grade electronic devices, such as a desktop or laptop computer executing instructions (such as a Python script) stored in a transitory or non-transitory computer readable medium. In some embodiments, the method may be carried out by accessing locally stored information (e.g., databases of genomic information, reference genomes, SNP information, and/or sample information) and/or information stored in remote databases and accessible via a network connection.

As will be described below, the methods described herein, including exemplary method 200, may achieve efficient location of target regions for SNP islands. The identified target regions may be useful in various applications, including determining markers of disease states, phenotypic traits, ancestry, and individual identity. As will be explained further below, the method may facilitate controlling several tunable variables that can affect which regions are identified as SNP island target regions; by adjusting various variables, the method may be applied multiple times to the same or similar data sets to yield different results that may be useful for different applications. For example, the method may be applied one time to find SNP island target regions having SNPs in the high-variance region that are highly-variant for the population at large, and it may then be applied a second time to find SNP island target regions having SNPs in the high-variance region that are highly variant for a specific genetic subset of the population (e.g., a specific ancestral subset). By adjusting parameters and/or input data for the method, different SNP island target regions that are particularly useful in differentiating identity among the target population (e.g., among the entire population versus among a particular ethnic subset) may be yielded. Manipulation of the filter parameters permits the modification of SNP island high-variance regions and low-variance regions, allowing for the quick design of SNP islands that are tailored to the application. Algorithms can be expanded beyond identity-linked SNPs to include ancestry or phenotype. For example, SNP island discovery using the algorithms can be designed using population-specific characteristics such as ancestry or ethnicity for the development of a targeted SNP panel, selective for a given population type. It has been noted that one of the most important criteria of an informative SNP is its compatibility with sequencing chemistries. To address this, the algorithmic parameters in the genome filtering algorithms can be modified to accommodate other sequencing chemistries At step 202, in some embodiments, the method begins by scanning along bases in a nucleic acid sequence, noting the relative locations of known SNPs. The scanning step may be executed by a component of a computer system having access to data regarding the known locations of SNPs, or it may be carried out in conjunction with a method for dynamically determining the locations of SNPs. In some embodiments, the location and identity of known SNPs may be retrieved by the system from local or remote computer storage, such as a database storing information about the human genome and about known SNPs. In some embodiments, a user of the system may have access to various different stored data regarding different genomes and/or different pluralities of known SNPs, and a user may specify which data the method is to scan. When referring to the reference nucleic acid sequence and the scanning process, the phrases "SNPs" and "SNP locations" may be used interchangeably; that is, a reference genome and SNP information may indicate that a known SNP occurs in some individuals at a certain location, and it may be said that the reference genome therefore contains a SNP at that location.

In some embodiments, the scanning may be on a base-by-base basis, where every base in the nucleic acid sequence is checked for a SNP; while in some other embodiments, the scanning may be on a SNP-by-SNP basis. In the latter case, for example, if a computer system has access to a database of known SNPs, where the data in the database notes both the existence of known SNPs and their locations, the computer system may cause the scanning process to proceed directly from the first known SNP (e.g., the known SNP closest to an end of the nucleic acid sequence) to the next known SNP, and so on, skipping bases entirely where the database does not indicate that a SNP exists. In some embodiments, as the method may apply analysis with regard to whether certain numbers of SNPs are located within contiguous regions of predefined lengths in bases, the scanning may be executed in accordance with a sliding window, such that an entire window of the predefined length is analyzed at once.

In some embodiments, scanning along bases in the nucleic acid sequence includes building and maintaining a state-based model, with each scanned SNP potentially affecting the state of the model. During scanning, there may be three active states in which the model may exist: (1) establishing low-variance segment I; (2) establishing high-variance segment; and (3) establishing low-variance segment II, as will be explained further below with respect to steps 204-214 of the method.

In some embodiments, scanning along bases in the nucleic acid sequence includes determining whether known SNPs are to be considered for the purpose of the system and method. The parameters that define what SNPs are to be considered may be adjusted by a user of the system. One way that a user may define which SNPs the system is to consider is to only define relevant SNPs and impactful SNPs. Relevant SNPs may be those SNPs that are known to have rates of occurrence that are not very high (e.g., not very close to 100%) and not very low (e.g., not very close to 0%). Impactful SNPs may be those SNPs that are most useful in differentiating and determining identity of individuals, by virtue of having rates of occurrence (e.g., rates of global occurrence, or rates of occurrence in any predefined subset of individuals) near 50%; impactful SNPs may be referred to as identity-relevant SNPs. A SNP having a rate of occurrence near 50% may be considered an identity-relevant SNP because SNPs that are present in too few or too many individuals may not be as useful in differentiating between different individuals.

In some embodiments, the system may define a window in which the rate of occurrence for a SNP must fall in order for the SNP to be considered a relevant SNP and/or an impactful SNP—for example, the system may only consider SNPs to be relevant and/or impactful if their rate of occurrence (e.g., global frequency) is known to fall above one of 0%, 0.1%, 0.5%, 1% 2%, 3%, 10%, 20%, 30%, 40%, 50%, 60%, 70%, 80%, or 90%; and/or known to fall below one of 99.9%, 99.5%, 99%, 98%, 97%, 90%, 80%, 70%, 60%, 50%, 40%, 30%, 20%, or 10%. In some embodiments, known rates of occurrence for SNPs may be determined in accordance with their global frequency (e.g., their rate of occurrence within the entire known population), while in some embodiments rates of occurrence for SNPs may be determined in accordance with their presentation rate within a subset of a population, such as an ancestral subset. A user of the system may select from among any suitable percentage values (including any of the aforementioned values) to define a window in which known rate of occurrence must fall for a SNP to be considered a relevant or impactful SNP. For example, if a user defines impactful SNPs as being required to have a known rate of occurrence between 40% and 60% in the relevant population, then a SNP having a known rate of occurrence of 45% would be counted as an impactful SNP by the system, while SNPs known to have respective rates of occurrence of 30% and 90% would both be considered non-impactful SNPs.

In some embodiments, impactful SNPs may be defined as SNPs having significance distinct from or in addition to identity-relevant significance. For example, impactful SNPs could be defined as those SNPs that are known to be relevant to phenotypes, diseases or other medical conditions, or any other known characteristic of SNPs. For example, the algorithm could be applied to locate SNP islands having clusters of medically relevant SNPs in order to create primers for efficient screening applications or other genomic analysis of medical patients. Additionally, SNPs that are known to have population or ancestry relevance could be defined to be significant SNPs. In some embodiments, the system may permit a user to designate one or more specific SNPs as significant SNPs, and to use the algorithm to determine whether the designated SNPs, alone or together with SNPs satisfying any other criteria to qualify as impactful, fall into a viable SNP island.

In some embodiments, the system may implement distinct definitions for relevant SNPs and impactful SNPs, and may consider relevant SNPs with respect to defining low-variance regions, while considering only impactful SNPs with respect to defining high-variance regions. For example, a user may define different windows for percentages of rates of occurrence for relevant SNPs and for impactful SNPs. In one example, impactful SNPs may be defined as those having a rate of occurrence between 40% and 60%, while the system may consider relevant SNPs as those with a rate of occurrence between 0.5% and 99.5%. This may be because SNPs falling in the high-variance region are desired to be identity-relevant, such that they may effectively distinguish between individuals. Meanwhile, the low-variance region may be desired to be substantially free of most or all SNP variation, in order to facilitate effective primer creation, such that SNPs having a very low or very high rate of occurrence may be more acceptable that SNPs having a rate of occurrence near 50%, as the very low or very high rate of occurrence may mean that a primer is likely to be ineffective with respect to a smaller percentage of the population.

At step 204, in some embodiments, the system determines whether a first low-variance region has been detected. In some embodiments, the system may determine after each scanned base or each scanned SNP whether a low-variance region has been detected. This step may take place while the model is in the first of the three states: (1) establishing low-variance segment I.

At step 206, in some embodiments, the determination as to whether a first low-variance region is detected includes determining whether, among the previous bases in a sliding window of a first predetermined length, less than a first maximum number of relevant SNPs have been detected. For example, a user may define a first predetermined length (e.g., number of bases) to be applied in determining whether a first low-variance region is detected, and the user may define a first maximum number of relevant SNPs that may be detected in determining whether a first low-variance region is detected. At each scanned base and/or at each scanned SNP, the system may then determine whether less than the first maximum number of relevant SNPs are located within a contiguous window of bases ending at the current base or current SNP and spanning backwards along the nucleic acid sequence for the first predetermined length. In accordance with a determination that the maximum number of relevant SNPs have been detected (or, alternately, that one more than the maximum number have been detected), the system may determine that a first low-variance region is not detected. Alternately, in accordance with a determination that less than the maximum number of relevant SNPs have been detected (or, alternately, that equal to but not greater than the maximum number have been detected), the system may determine that a first low-variance region is detected and that the low-variance region is defined by the contiguous window of bases ending at the current base or current SNP and spanning backwards along the nucleic acid sequence for the first predetermined length.

In some embodiments, the first predetermined length (in number of bases) may be defined by user input, or automatically be set to a default value. In some embodiments, the parameter may be dynamically determined. In some embodiments, the first predetermined length may be set or chosen in accordance with a length (number of bases) that ensures that effective primers can be designed based on segments of the nucleic acid sequence that are equal to or less than that length. For example, the first predetermined length may be set to a length of 50 bases, 100 bases, 150 bases, or 200 bases. In some embodiments, the first predetermined length may be a minimal length, such that a low-variance region may be defined to be equal to or longer than, but not shorter than, the first predetermined length. While this application discusses using the techniques disclosed herein to determine locations in nucleic acid sequences for which to design primers, the techniques may be similarly applicable to determine locations in nucleic acid sequences for which to select and apply already-designed primers.

In some embodiments, a user may specify a minimum, maximum, or target base length for an entire SNP island target region, including two low-variance regions and a high-variance region together. For example, a user may require the entire SNP island target region to be less than 600 bases in length, due to restrictions on abilities to sequence longer sequences.

In some embodiments, the first maximum number of relevant SNPs may be defined by user input, or automatically be set to a default value. In some embodiments, the parameter may be dynamically determined. In some embodiments, the first maximum number of relevant SNPs may be set or chosen in order to ensure that primers designed for the region will be effective for a sufficient percentage of the population. For example, the first maximum number of SNPs may be set to zero or to one, such that no relevant SNPs are permitted to be located in a low-variance region, or such that only a single relevant SNP is permitted to be located in a low-variance region. In embodiments in which one or more relevant SNP is permitted to be present in a low-variance region, degenerate primers may be designed and used in order to account for the presence of the one or more SNPs and the potential presence of subjects in a test pool having differing nucleotides at the location(s) of the one or more SNPs. Greater numbers of SNPs in low-variance regions, requiring exponentially more degenerate primers, may be permissible in situations in which only one or few SNP islands are to be analyzed at once, as such a procedure may allow for greater numbers of degenerate primers in a mix; however, it may be undesirable, inefficient, labor-intensive, and/or ineffective to have large numbers of degenerate primers for large numbers (e.g., dozens, scores, hundreds) of SNP islands.

The lower the maximum number of relevant SNPs that are permitted to be located in a low-variance region, the more effective, efficient, and simple primer design may be; however, the higher the maximum number of relevant SNPs that are permitted to be located in a low-variance region, the more potential SNP island target regions may be defined. In some embodiments, users of a system may adjust a maximum number of relevant SNPs permitted in a low-variance region depending on the underlying nucleic acid sequence being analyzed. For example, if a nucleic acid sequence (e.g., reference genome) has a very high number of known SNPs and/or a very dense distribution of SNPs, then it may be necessary to increase the maximum permissible number of relevant SNPs allowed in a low-variance region in order to ensure that a sufficient number of SNP island target regions are returned by the system.

As discussed above, in some embodiments, the system may only consider (e.g., only count) certain SNPs as relevant SNPs. For example, in some embodiments, a system may count all known SNPs without regard for known rates of occurrence for any known SNP; alternately, only SNPs whose rate of occurrence falls above a minimum rate (e.g., 0.1%, 0.5%, 1%, 2%, 3%, etc.) and below a maximum rate (e.g., 99.9%, 99.5%, 99%, 98%, 97%, etc.) may be counted by the system, such that SNPs that are known to be very uncommon or very common will not disqualify an otherwise permissible region from being determined to be a low-variance region.

In accordance with a determination that a first low-variance region is not detected, the method may proceed from step 204 to step 208.

At step 208, in some embodiments, the system may advance along the nucleic acid sequence, continue to scan along the bases in the nucleic acid sequence, and continue to note the relative locations of known SNPs. In some embodiments, scanning may continue at the next base or next SNP. Advancing to step 208 from step 204 (or from step 210 or step 214, as referenced below) which leads to another application of step 204, may make the method 200 iterative, such that the method repeatedly searches for the regions that may comprise a SNP island as it continues to scan along the length of a nucleic acid sequence such as a reference genome. Failing to successfully detect a SNP island target region may accordingly cause the system to continue searching at different parts of the nucleic acid sequence.

Returning to steps 204 and 206, in accordance with a determination that a first low-variance region is detected, the method may proceed from step 204 to step 210. Further in accordance with the determination that a first low-variance region is detected, the system may change the model from the first state [(1) establishing low-variance segment I] to the second state: (2) establishing high-variance segment.

At step 210, in some embodiments, the system determines whether a high-variance region is detected immediately following the detected the first low-variance region. This step may take place while the model is in the second of the three states: (2) establishing high-variance segment.

At step 212, in some embodiments, the determination as to whether a high-variance region is detected includes determining whether, among the bases following the first low-variance region in a window of a second predetermined length, at least a minimum number of impactful SNPs are detected. For example, a user may define a second predetermined length (e.g., number of bases) to be applied in determining whether a first high-variance region is detected, and the user may define a minimum number of impactful SNPs that must be detected in order to determine that a high-variance region is detected. In the window of bases defined starting at the base immediately following the detected first low-variance region and spanning forward along the nucleic acid sequence for the second length, the system may then determine how many SNPs are located in the window, and may determine whether the number of impactful SNPs in the window is equal to or greater than the defined minimum number of impactful SNPs required for confirmation of a high-variance region. In accordance with a determination that at least the minimum number of impactful SNPs are not detected, the system may determine that a high-variance region is not detected. Alternately, in accordance with a determination that at least the minimum number of impactful SNPs are detected, the system may determine that a high-variance region is detected and that the high-variance region is defined by the contiguous window of bases starting one base after the first low-variance region and spanning forward along the nucleic acid sequence by the defined second predetermined length.

In some embodiments, the second predetermined length (in number of bases) may be defined by user input, or automatically be set to a default value. In some embodiments, the parameter may be dynamically determined. In some embodiments, the second predetermined length may be set or chosen in accordance with a length (number of bases) that ensures that a sufficient number of SNPs may be reasonably likely to be detected in a span of that length. In some embodiments, the second length may be set in accordance with the capabilities of a sequencer, such that the length should be short enough to be sequenced for analysis. For example, the second predetermined length may be set to a length of 50 bases, 100 bases, 200 bases, 300 bases, 400 bases, or 500 bases. In some embodiments, the predetermined length may be longer than 500 bases, such as when a user intends to use a sequencer capable of handling much longer sequences (e.g., Pacific Biosciences sequencing technology).

In some embodiments, the second predetermined length may be a maximal length, such that a high-variance region may be defined to be equal to or shorter than, but not longer than, the second predetermined length. In some embodiments, during base-by-base or SNP-by-SNP scanning, the system may determine that the required number of impactful SNPs have been confirmed in a span following the first low-variance region, and may determine that the span constitutes a high-variance region without further analyzing the remainder of the nucleic acid sequence to determine the total number of SNPs present within the maximal permissible length following the first low-variance region. In some other embodiments, the system may determine the total number of impactful SNPs present within the maximal permissible length following the first low-variance region regardless of whether or not the required number of impactful SNPs to constitute a high-variance region is detected within a shorter span within the larger area.

In some embodiments, if at least the minimum required number of impactful SNPs are located in a span of less than the maximal permissible length following the first low-variance region, then the system may flexibly determine where the high-variance region should be deemed to end, and the system may make this determination with respect to whether an acceptable second low-variance region may be found following the high-variance region. Determining whether a second low-variance region is located following a high-variance region will be discussed in greater detail below with respect to steps 214-216. However, stated briefly, if the system determines that enough impactful SNPs are located within a span for the span to constitute a high-variance region, where the span is shorter than the maximal permissible length for a high-variance region, then a high-variance region may be defined as ending immediately following the already-detected impactful SNPs, or it may be defined as ending further down the nucleic acid sequence. The determination as to where the high-variance region should be defined as ending may depend on where an acceptable second low-variance region can be located. Thus, if there are no additional relevant SNPs in the span following the already-located impactful SNPs in the high-variance region, then the high-variance region may be defined as ending immediately following the already-located impactful SNPs, such that the region having no relevant SNPs can serve as a second low-variance region. However, if there is an additional relevant SNP or an additional cluster of relevant SNPs following the already-located impactful SNPs in the high-variance region, and the additional one or more relevant SNPs are close enough to the already-located impactful SNPs to fall within the maximal length for the high-variance region, then the high-variance region may be defined to be long enough to include the additional one or more relevant SNPs, such that the additional one or more relevant SNPs do not disqualify the region following the high-variance region from being defined as an acceptable low-variance region.

In some embodiments, the minimum number of impactful SNPs may be defined by user input, or automatically be set to a default value. In some embodiments, the parameter may be dynamically determined. In some embodiments, the minimum number of impactful SNPs may be set or chosen in order to ensure that SNP island target areas contain enough impactful SNPs to be probabilistically expected to be able to distinguish large numbers of individuals from one another. For example, the minimum number of impactful SNPs may be set to five or more impactful SNPs, four impactful SNPs, three impactful SNPs, or two impactful SNPs. The lower the minimum number of impactful SNPs that are required to be located in a high-variance region, the more SNP islands may be defined; however, the lower the minimum number of impactful SNPs that are required to be located in a high-variance region, the less effective the impactful SNPs in the SNP island target region may be at distinguishing individuals from one another. In some embodiments, users of a system may adjust a minimum number of impactful SNPs required in a low-variance region depending on the underlying nucleic acid sequence being analyzed. For example, if a nucleic acid sequence (e.g., reference genome) has a very low number of known SNPs and/or a very low-density distribution of SNPs, then it may be necessary to decrease the minimum number of impactful SNPs required in a high-variance region in order to ensure that a sufficient number of SNP island target regions are returned by the system.

As discussed above, in some embodiments, the system may only consider (e.g., only count) certain SNPs to be impactful SNPs. For example, in some embodiments, a system may count all known SNPs without regard for known rates of occurrence as impactful SNPs; alternately, only SNPs having rates of occurrence falling sufficiently close to 50% (e.g., between 40% and 60%, or between 30% and 70%) may be considered impactful SNPs, such that SNPs that would not be expected to meaningfully distinguish significant portions of the population from the rest of the population would not be allowed to define the presence of a high-variance region.

In accordance with a determination that a high-variance region is not detected, the method may proceed from step 210 to step 208.

In accordance with a determination that a high-variance region is detected, the method may proceed from step 210 to step 214. Further in accordance with the determination that a high-variance region is detected, the system may change the model from the second state [(2) establishing high-variance segment] to the third state: (3) establishing low-variance segment II.

At step 214, in some embodiments, the system determines whether a second low-variance region has been detected immediately following the high-variance region. This step may take place while the model is in the third of the three states: (3) establishing low-variance segment II.

At step 216, in some embodiments, the determination as to whether a second low-variance region is detected includes determining whether, among the bases following the high-variance region in a window of a third predetermined length, less than a second maximum number of relevant SNPs are detected. The determination as to whether a second low-variance region is detected may be carried out in the same or similar manner as discussed above with respect to determining whether a first low-variance region is detected in steps 204 and 206, except that the location of the second low-variance region may be defined as beginning immediately following the end of the high-variance region in the nucleic acid sequence. The limitations (e.g., parameters) may be input by a user, may be predetermined by the system, or may be dynamically determined by the system.

In some embodiments, the length restraints and relevant-SNP quantity limitations applied to the second low-variance region may be the same as those applied to the first low-variance region, though in some embodiments they may be different. For example, in some embodiments, neither low-variance region may be permitted to contain any relevant SNPs; in some embodiments, both low-variance regions may be required to contain no more than one relevant SNP. In some embodiments, both low-variance regions may be required to be at least the same minimum length (number of bases), while in some embodiments different minimum base length requirements may be applied to each low-variance region.

In some embodiments, a total limitation on the number of relevant SNPs detected in both low-variance regions may be applied, such that if the first and second low-variance regions together may be permitted to contain no more than a total predefined number of relevant SNPs. For example, if the total predefined number of permissible relevant SNPs in both regions combined is one, and the first low-variance region contains one relevant SNP, then the second region may not be permitted to contain any relevant SNPs. However, if the total predefined number of permissible relevant SNPs in both regions combined is one, and the first low-variance does not contain any relevant SNPs, then the second region may be permitted to contain up to one relevant SNP.

In some embodiments, the same or similar definition as to what SNPs are considered relevant SNPs may be applied as discussed above with respect to the first low-variance region. In some embodiments, the definition as to what SNPs are considered relevant SNPs may be different for the first low-variance region and the second-low variance region; for example, a user could configure the system such that the first low-variance region considers relevant SNPs as those occurring in more than 0.1% and less than 99.9% of relevant individuals, while the second low-variance region only considers relevant SNPs as those occurring in more than 1% and less than 99% of individuals.

As discussed above with respect to the high-variance region, in some embodiments the length of the high-variance region recognized by the system may be flexible, such that the system may designate the high-variance region to be shorter or longer in order to accommodate the location of a low-variance region immediately adjacent to the high-variance region. For example, if the system determines that a high-variance region may exist at a first location, but then locates a cluster of several relevant SNPs shortly after the end of the first location, then the system may determine that the high-variance region should span beyond the first location to also encompass the cluster of relevant SNPs further along the nucleic acid sequence (so long as they are close enough to the first region to be within the maximum permissible length for a high-variance region). Thus, in some embodiments, a system may encounter one or more relevant SNPs while in the third state—e.g., while searching for a second low-variance region—and may accordingly determine that a low-variance region may not encompass those relevant SNPs. If possible, in some embodiments, the system may thus redefine the high-variance region such that the presumed length of the high-variance region is increased to encompass the newly-encountered relevant SNPs. The system may then resume scanning (e.g., in accordance with steps 214 and 216) for a permissible low-variance region immediately following the newly-defined high-variance region.

In accordance with a determination that a second low-variance region is not detected, the method may proceed from step 204 to step 208. In some embodiments, the process described above regarding adjusting the length of the high-variance region may alternately be carried out in response to determining that a second low-variance region is not detected (e.g., in accordance with a determination that more than the maximum permissible number of relevant SNPs is located in the region being scanned). In some embodiments, if the high-variance region cannot be expanded or lengthened to accommodate additional relevant SNPs encountered, because expanding the high-variance region would cause it to exceed the maximum length for a high-variance region, then the system may determine that a second low-variance region is not detected.

In accordance with a determination that a first low-variance region is detected, the method may proceed from step 214 to step 218. At step 218, in some embodiments, the system may determine that a contiguous region in the nucleic acid sequence comprising the first low-variance region, the high-variance region, and the second low-variance region constitutes a SNP island target region. In some embodiments, the system may store, transmit, and/or output data indicating the location of the SNP island target region (e.g., the location of the bases comprising the region), including the locations of the bases inside the SNP island target region that demarcate the three sub-regions from one another. For example, data may be output in variant call file (vcf) format. In some embodiments, the data stored or output may additionally include the location of known SNPs in the SNP island target region, and information about the identity and nature of each known SNP.

SNP Island Target Region Filtering

Figure 3:
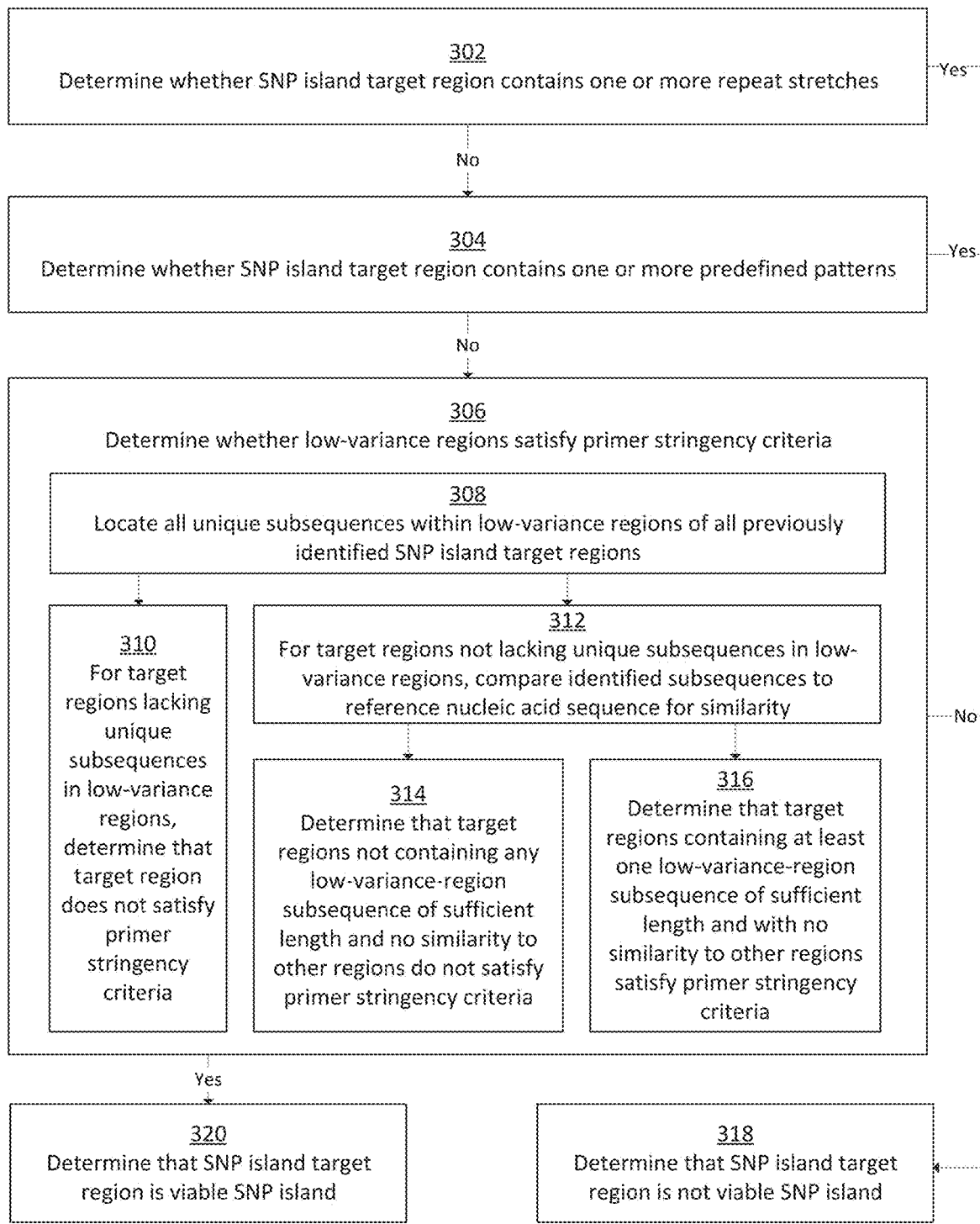
FIG. 3 is a flowchart depicting a method for filtering SNP island target regions to isolate viable SNP islands, in accordance with some embodiments.

FIG. 3 depicts a method for filtering SNP island target regions in a nucleic acid sequence such as a known genome, in accordance with some embodiments. The method 300 may be performed by a system such as system 100 described above with reference to FIG. 1. The SNP island target regions being filtered may be SNP island target regions generated in accordance with some or all of the steps discussed above with respect to method 200. In some embodiments, the method may be executed in whole or in part by a computer processor executing instructions stored in a transitory or non-transitory computer readable medium. In some embodiments, the method may be executed in whole or in part by one or more physical or virtual computer servers located remotely from an end-user, such that a user may access or implement the method through the use of a local client device and may cause one or more remote servers to execute the method. In some embodiments, the method may be executed in whole or in part by one or more consumer-grade electronic devices, such as a desktop or laptop computer executing instructions stored in a transitory or non-transitory computer readable medium. In some embodiments, the method may be carried out by accessing locally stored information (e.g., databases of genomic information, reference genomes, SNP information, and/or sample information) and/or information stored in remote databases and accessible via a network connection. In some embodiments, system 100 may process output generated by method 200, such as by applying a Python script or other instructions stored on a computer readable storage medium to data, generated by method 200, that represents the SNP island target region.

The methods described herein, including method 300, may facilitate the efficient and accurate isolation of SNP island target regions that are useful in various applications, including determining markers of disease states, phenotypic traits, ancestry, and individual identity. Method 300 may efficiently and effectively narrow a large field of SNP island target regions down to a smaller pool of validated SNP islands that are known or expected to be amenable to primer design, such that primers that uniquely amplify the SNP island may be designed for the low-variance regions. Method 300 may ensure that SNP island target regions are excluded if they have long strings of repeating bases, have predefined patterns, or have stretches that exactly or nearly match any other part of the reference nucleic acid sequence, thus ensuring that primers designed for the SNP island target regions will uniquely and effectively amplify the SNP island target region.

At step 302, in some embodiments, the system may determine whether a SNP island target region contains one or more repeat stretches. Such repeat stretches may potentially interrupt DNA sequencing chemistries (e.g., Illumina DNA sequencing chemistries). In some embodiments, the system may scan a SNP island target region by scanning along the sequence length in a sliding window of a fixed length (e.g., 10 bases in length, 20 bases in length, etc.), advancing down the sequence in single-base increments. The system may determine that a repeat stretch exists if a stretch of a predefined number of bases are the same nucleotide; in some embodiments, the same nucleotide repeated three times may be considered a repeat stretch, while in some embodiments the number of repeats required to define a repeat stretch may be four, five, or more. In some embodiments, one or more located repeat stretches may disqualify a target region from being considered a viable SNP island, while in some other embodiments two or more, three or more, or four or more repeat stretches may be required in order to disqualify a target region from being considered a viable SNP island. If it is determined that the SNP island target region contains one or more repeat stretches, the method may proceed to step 318.

At step 318, in some embodiments, the system may determine that the SNP island target region is not a viable SNP island. In accordance with such a determination, the system may store, transmit, and/or output an indication associated with data representing the SNP island target region, wherein the indication denotes that the SNP island target region is not a viable SNP island. In some embodiments, the indication may contain information explaining the manner in which the SNP island target region was determined not to be a viable SNP island. Storing information regarding the manner in which the SNP island target region was determined not to be a viable SNP island may facilitate reevaluating the SNP island target region at a future time if the system or a user adjusts the requirements for a SNP island target region to qualify as a SNP island. In some embodiments, in accordance with the determination that the SNP island target region is not a viable SNP island, the system may simply delete stored data representing the SNP island target region.

Returning to step 302, if it is determined that the SNP island target region does not contain one or more repeat stretches, the method may proceed to step 304.

At step 304, in some embodiments, the system may determine whether a SNP island target region contains one or more predefined patterns of the same nucleotide composition repeated. Such predefined patterns may potentially interrupt DNA sequencing chemistries (e.g., Illumina DNA sequencing chemistries). In some embodiments, the system may scan a SNP island target region by scanning along the sequence length in a sliding window of a fixed length (e.g., 10 bases in length, 20 bases in length, etc.), advancing down the sequence in single-base increments. The system may determine that a predefined pattern exists in the SNP island target region if the target region includes two or more stretches of the same pattern of bases repeated. In some embodiments, the system may examine stretches between two bases in length and seven bases in length in order to determine, by comparing the target sequence to itself under that range of base offsets, whether repeating stretches of the defined base length exist. In some embodiments, the system may examine stretches of length longer than seven bases. The system may determine that a predefined pattern is detected if a specific stretch of bases of the defined base length is found to repeat equal to or more than a predefined number of times. In some embodiments, two consecutive repetitions of a specific stretch of bases may define a predefined pattern, while in some embodiments three, four, five, six, or more consecutive repetitions of a specific stretch of bases may be required to define a predefined pattern.

If it is determined that the SNP island target region does contain one or more predefined patterns, the method may proceed to step 318.

If it is determined that the SNP island target region does not contain one or more predefined patterns, the method may proceed to step 306.

At step 306, in some embodiments, the system may determine whether low-variance regions of the SNP island target region satisfy primer stringency criteria. In some embodiments, the system may require both a first and second low-variance region of a SNP island target region to satisfy primer stringency criteria, while in some embodiments a system may require only one low-variance region to satisfy primer stringency criteria. In some embodiments, the determination as to whether the low-variance regions satisfy primer stringency criteria may be made in accordance with steps 308-316.

At step 308, in some embodiments, the system locates all unique subsequences within low-variance regions of all previously identified SNP island target regions. This step may require analysis not only of a single SNP island target region, but also of other SNP island target regions, such as those generated in accordance with (perhaps multiple iterations of) method 200. Identifying unique subsequences may require comparing the low-variance region with the entire nucleic acid sequence (e.g., the entire known genome) in order to find unique subsequences. In some embodiments, the system may search for unique subsequences having a predefined minimum length, such as 10 bases, 15 bases, 20 bases, or 21 bases. The predefined minimum length for a unique subsequence may be chosen to reasonably ensure that primers can be effectively designed by use of the subsequence.

At step 310, in some embodiments, for SNP island target regions lacking unique subsequences in low-variance regions, the system may determine that the region does not satisfy primer stringency criteria. In some embodiments, target regions having one low-variance region lacking unique subsequences may be disqualified, while in some embodiments both low-variance regions in a target region must be lacking in unique subsequences for the target region to be disqualified. In some embodiments, a predefined minimum number of unique subsequences—applicable to one low-variance region, to each low-variance regions, or to the two low-variance regions taken together—may be required.

Alternately to step 310, at step 312, in some embodiments, for target regions not lacking unique subsequences in low-variance regions, the system may compare identified subsequences to the reference nucleic acid sequence to determine similarity. In some embodiments, step 312 may be performed on all identified unique subsequences for any SNP island target region having at least the minimum number of required unique subsequences, such as one unique subsequence, two unique subsequences, or three or more unique subsequences. In some embodiments, tools such as the BLASTn tool from the National Center for Biotechnology Information may be used to determine whether the subsequences have similarity to the reference nucleic acid sequence, such as by comparing subsequences to the human genome reference sequence (e.g., version GRCh37.p13; GenBank assembly accession GCA_000001405.14). In some embodiments, other tools such as the NCBI blast tool or the Ensembl blast tool may be used.

At step 314, in some embodiments, the system may determine that target regions not containing any low-variance-region subsequence of sufficient length (e.g., at least 5 bases, 10 bases, or 15 bases) and no similarity to other regions in the reference genome do not satisfy primer stringency criteria. Thus, in some embodiments, in order for a target region to satisfy primer stringency criteria, the target region must contain a low-variance-region subsequence, wherein the subsequence (a) is of sufficient length and (b) has no similarity to other regions in the reference genome. In some embodiments, a subsequence having no similarity to other regions in the genome may be defined as a subsequence that does not exactly match any other region in the genome, or it may be defined as a subsequence that does not exactly or nearly match (e.g., above a predefined percentage of bases in the subsequence) any other region in the genome.

Alternately to step 314 at step 316, in some embodiments, the system may determine that target regions containing at least one low-variance-region subsequence of sufficient length and no similarity to other regions satisfy primer stringency criteria. In some embodiments, rather than the distinction between steps 314 and 316 being no satisfactory subsequences versus at least one satisfactory subsequence, the distinction may be set at another number of satisfactory subsequences, such as one, two, or three or more satisfactory subsequences.

Continuing from steps 306-316, if it is determined that the low-variance regions do not satisfy primer stringency criteria, the method may proceed to step 318.

Alternately, continuing from steps 306-316, if it is determined that the low-variance regions do satisfy primer stringency criteria, the method may proceed to step 320.

At step 320, in some embodiments, the system may determine that the SNP island target region is a viable SNP island. In accordance with such a determination, the system may store, transmit, and/or output an indication associated with data representing the SNP island target region, wherein the indication denotes that the SNP island target region is a viable SNP island. In some embodiments, the indication may contain information explaining the manner in which the SNP island target region was determined to be a viable SNP island. Storing information regarding the manner in which the SNP island target region was determined to be a viable SNP island may facilitate reevaluating the SNP island target region at a future time if the system or a user adjusts the requirements for a SNP island target region to qualify as a SNP island.

In some embodiments, additional filters may be applied to SNP island target regions to determine whether they may be viable SNP islands. For example, a system may exclude SNP island target regions based on feasibility considerations regarding known primer design capabilities and laboratory capabilities. For example, following computational validation and filtering, laboratory tests may be used to manually confirm that primers can be designed to uniquely and effectively amplify for the SNP island target region, and if primers cannot be so designed then the region may be determined to not be viable as a SNP island.

In some embodiments, in accordance with the determination that a SNP island target region is a viable SNP island, primers for targeted amplification of the SNP island may be designed for one or both of the low-variance regions of the SNP island.

Distinguishing Individual Nucleic Acid Samples from One Another

Figure 4:
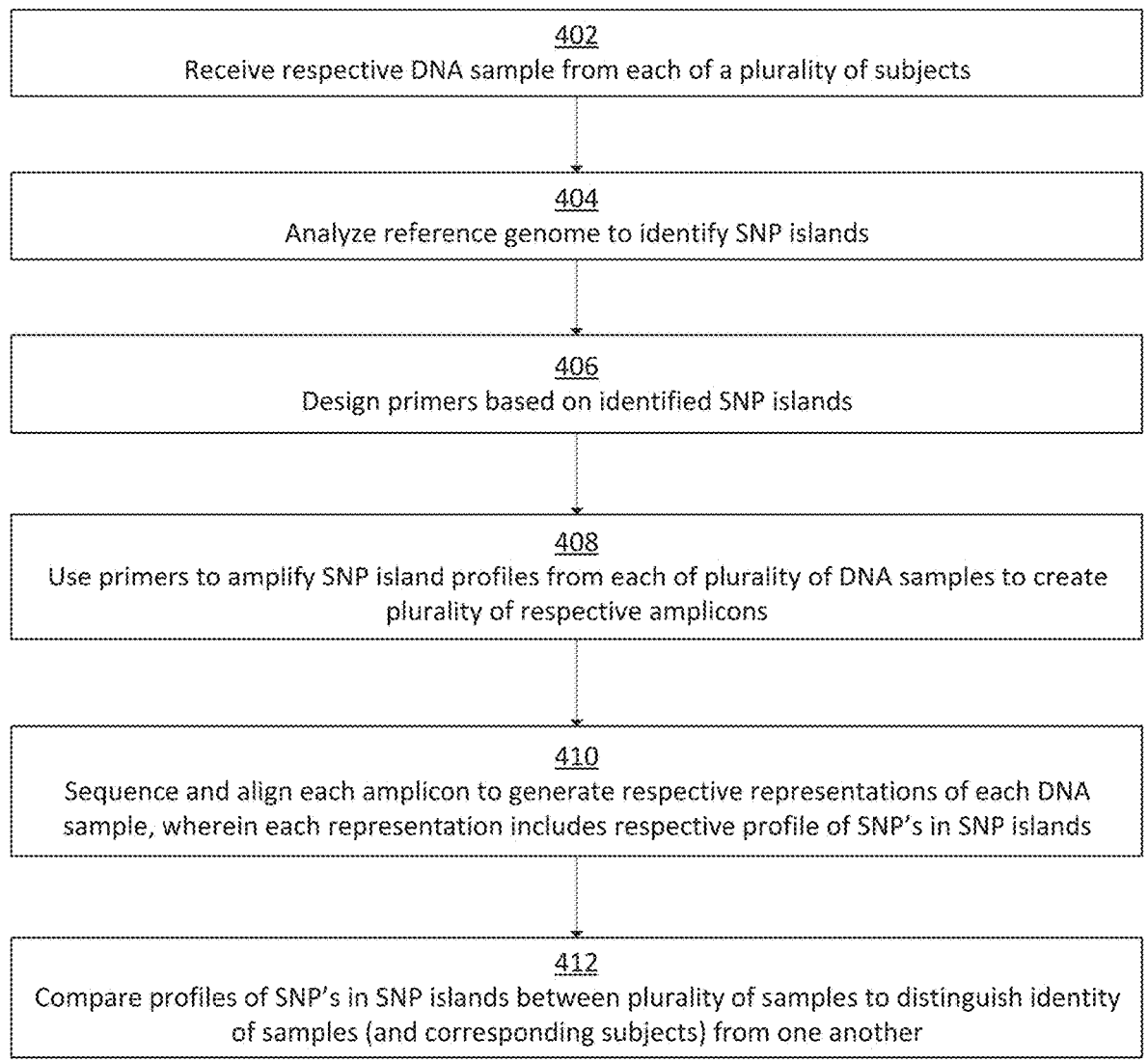
FIG. 4 is a flowchart depicting a method for using SNP islands to distinguish DNA samples from one another, in accordance with some embodiments.

FIG. 4 depicts a method for distinguishing the identity of genomic samples and corresponding individuals from one another based on analysis of SNPs in SNP islands, in accordance with some embodiments. The method 400 may be performed by a system such as system 100 described above with reference to FIG. 1. In some embodiments, the method may be executed in whole or in part by a computer processor executing instructions stored in a transitory or non-transitory computer readable medium. In some embodiments, the method may be executed in whole or in part by one or more physical or virtual computer servers located remotely from an end-user, such that a user may access and/or implement the method through the use of a local client device and may cause one or more remote servers to execute the method. In some embodiments, the method may be executed in whole or in part by one or more consumer-grade electronic devices, such as a desktop or laptop computer executing instructions (such as a Python script) stored in a transitory or non-transitory computer readable medium. In some embodiments, the method may be carried out by accessing locally stored information (e.g., databases of genomic information, reference genomes, SNP information, and/or sample information) and/or information stored in remote databases and accessible via a network connection.

In some embodiments, respective samples of DNA or other genomic material corresponding to a plurality of individuals may be compared on the basis of SNP islands identified in accordance with one or both of methods 200 and/or 300 discussed above. By utilizing methods 200 and 300 discussed above, primers may be designed to efficiently and effectively amplify the DNA samples in areas that facilitate the creation of reads having high numbers of identity-relevant SNPs. By analyzing the samples at the SNP islands as identified by methods 200 and/or 300, labor and time investment may be minimized, depth of coverage achieved may be increased, and creation of high numbers of identity-relevant SNP profiles corresponding to analyzed samples may be achieved.

At step 402, in some embodiments, the system may receive respective DNA samples from each of a plurality of subjects. For example, DNA samples (e.g., gDNA) or other genomic material may be obtained in a plurality of separate samples, wherein each sample pertains to a respective individual.

At step 404, in some embodiments, the system may analyze a reference genome to identify SNP islands. This analysis may be performed in accordance with any or all of the techniques described above with respect to methods 200 and 300. In some embodiments in which the DNA samples received in step 402 are human DNA samples, the reference genome may be a reference human genome.

At step 406, in some embodiments, the system may design primers based on the identified SNP islands. In some embodiments, designing primers may include computationally designing primer sets for unique sequences in low-variance regions of the identified SNP islands, wherein the primers are designed to amplify at least the portion of the SNP island including the impactful SNPs in the high-variance region. Primer length range may be set to be greater than a predetermined minimum length such as 20 bases, 25 bases, or 30 bases, and less than a predetermined maximum length such as 40 bases, 45 bases, or 50 bases. Target melting temperature may be set to an appropriate melting temperature according to one or more goals of the study, such as 60° C., 70° C., 80° C., or any other suitable melting temperature.

At step 408, in some embodiments, the system may use the primers to amplify SNP island profiles from each of the plurality of DNA samples to create a plurality of respective amplicons. In some embodiments, contributor gDNA for each sample may be amplified in one or more multiplexed or singleplexed reactions. After amplification, amplicons for each sample may be cleaned.

At step 410, in some embodiments, the system may sequence and align each amplicon to generate respective representations of each DNA sample, wherein each representation includes a respective profile of SNPs in the SNP islands. Sequencing may be carried out using paired-end sequencing libraries, and paired sequence read files may be generated from sequencing. Reads from each sample may be aligned in a paired-end sequence alignment to the reference genome, creating respective resulting sequence alignment maps (SAM files), sorted binary-sequence/alignment map (BAM) files, or other files representing each respective sample. SNP calls may be performed using the files to output allele files, which may be in variant call file format. In some embodiments, nucleotide read and depth of coverage (DOC) at each SNP position may be calculated.

At step 412, in some embodiments, the system may compare the profiles of SNPs in the SNP islands between the plurality of samples to distinguish the identity of samples (and corresponding subjects) from one another. In some embodiments, each individual impactful SNP location from each subject/sample may be compared to the corresponding impactful SNP location from each other subject/sample to determine whether the nucleotide at the impactful SNP location is the same or different. In some embodiments, a similarity (e.g., percentage) of each subject/sample may be calculated with respect to each other subject/sample based on all impactful SNP locations in the SNP islands. In some embodiments, a heatmap of SNP profile relatedness of each subject/sample to the other subject/samples may be generated. By isolating differences in the SNP profiles of each sample, each of the subjects may be differentiated from one another, and a sample corresponding to an unknown one of the subjects may be matched to its most-similar SNP profile to identify the subject to which it corresponds.

Distinguishing Single-Contributor Samples from Multi-Contributor Samples

Figure 5:
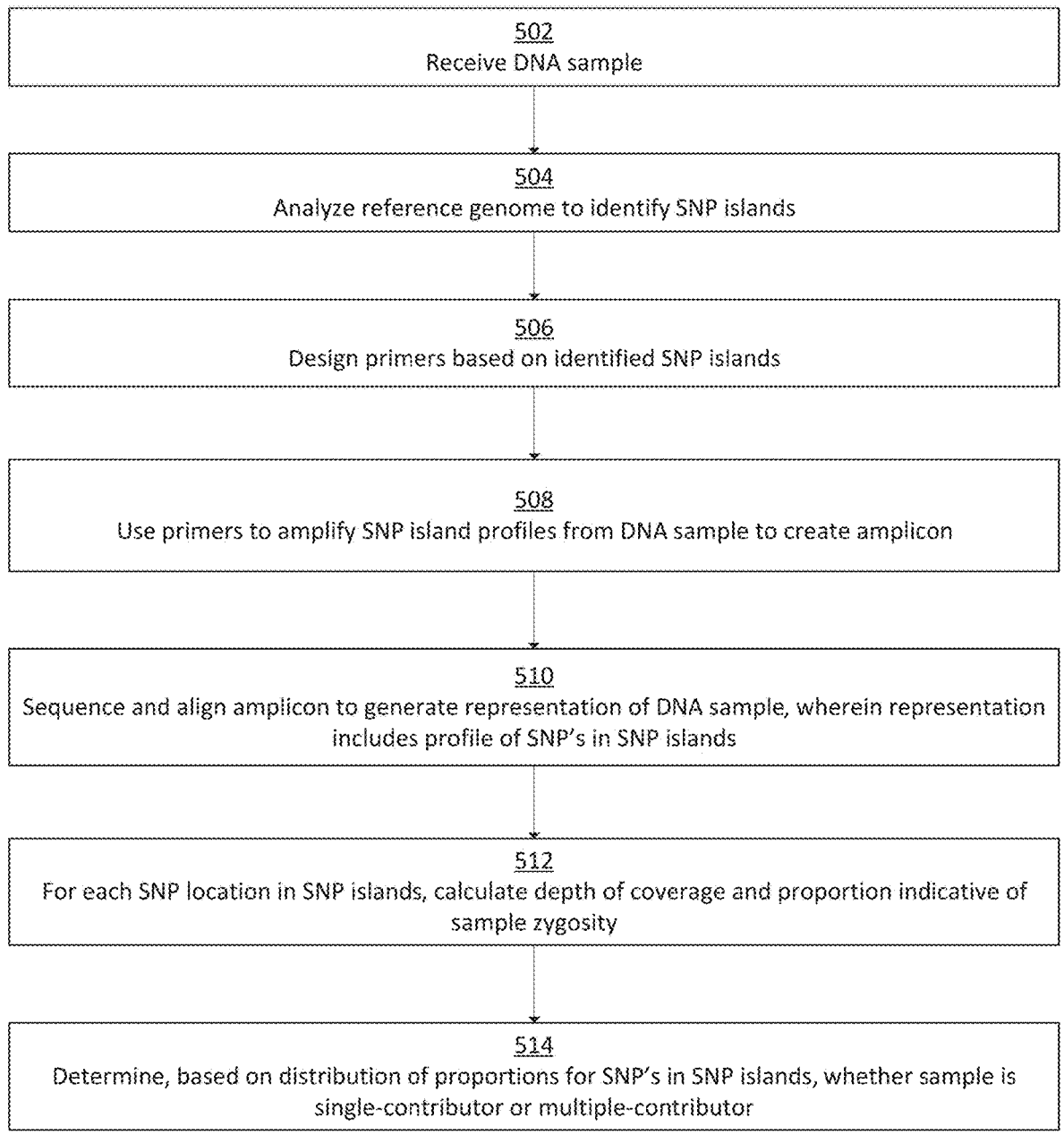
FIG. 5 is a flowchart depicting a method for using SNP island target regions to determine whether a DNA sample is from a single contributor or from multiple contributors, in accordance with some embodiments.

FIG. 5 depicts a method for determining whether a genomic sample is a single-contributor sample or a multiple-contributor sample, based on analysis of zygosity of SNPs in SNP islands, in accordance with some embodiments. The method 500 may be performed by a system such as system 100 described above with reference to FIG. 1. In some embodiments, the method may be executed in whole or in part by a computer processor executing instructions stored in a transitory or non-transitory computer readable medium. In some embodiments, the method may be executed in whole or in part by one or more physical or virtual computer servers located remotely from an end-user, such that a user may access and/or implement the method through the use of a local client device and may cause one or more remote servers to execute the method. In some embodiments, the method may be executed in whole or in part by one or more consumer-grade electronic devices, such as a desktop or laptop computer executing instructions (such as a Python script) stored in a transitory or non-transitory computer readable medium. In some embodiments, the method may be carried out by accessing locally stored information (e.g., databases of genomic information, reference genomes, SNP information, and/or sample information) and/or information stored in remote databases and accessible via a network connection.

In some embodiments, one or more samples of DNA or other genomic material may be sequenced and aligned, and depth of coverage (DOC) and a proportion indicative of zygosity may be calculated for each impactful SNP location in various SNP islands, wherein the SNP islands may be identified in accordance with one or both of methods 200 and/or 300 discussed above. The distribution of proportions calculate for the plurality of SNPs in the SNP islands may then be analyzed to determine whether the sample is a single-contributor sample or a multiple-contributor sample. By utilizing methods 200 and 300 discussed above, primers may be designed to efficiently and effectively amplify the DNA samples in areas that facilitate the creation of reads having high numbers of identity-relevant SNPs and yielding high DOC. By analyzing the samples at the SNP islands as identified by methods 200 and/or 300, labor and time investment may be minimized, depth of coverage may be increased, and high numbers of identity-relevant SNP profiles sufficient to create a distribution of zygosity demonstrating whether a sample is single-contributor or multiple-contributor may be created.

At step 502, in some embodiments, the system may receive a DNA sample. For example, a DNA sample (e.g., gDNA) or other genomic material may be obtained as a single sample, wherein the system and/or user may be unaware of whether the sample contains DNA from a single contributor (e.g., single organism) or multiple contributors (e.g., multiple organisms).

At step 504, in some embodiments, the system may analyze a reference genome to identify SNP islands. This analysis may be performed in accordance with any or all of the techniques described above with respect to methods 200 and 300. In some embodiments in which the DNA sample received in step 402 is known to be human DNA, the reference genome may be a reference human genome.

At step 506, in some embodiments, the system may design primers based on the identified SNP islands. In some embodiments, designing primers may include computationally designing primer sets for unique sequences in low-variance regions of the identified SNP islands. Primer length range may be set to be greater than a predetermined minimum length such as 20 bases, 25 bases, or 30 bases, and less than a predetermined maximum length such as 40 bases, 45 bases, or 50 bases. Target melting temperature may be set to an appropriate melting temperature, such as 70° C.

At step 508, in some embodiments, the system may use the primers to amplify SNP island profiles from the DNA sample to create an amplicon. In some embodiments, gDNA from the sample may be amplified in one or more multiplexed or singleplexed reactions. After amplification, amplicons may be cleaned.

At step 510, in some embodiments, the system may sequence and align the amplicon to generate a representation of the DNA sample, wherein the representation includes a profile of SNPs in the SNP islands. Sequencing may be carried out using paired-end sequencing libraries, and paired sequence read files may be generated from sequencing. Reads from the sample may be aligned in a paired-end sequence alignment to the reference genome, creating one or more resulting SAM files, sorted BAM files, or other files representing the sample. SNP calls may be performed using the files to output allele files, which may be in variant call file format.

At step 512, in some embodiments, the system may, for each impactful SNP location in the SNP islands, calculate depth of coverage (DOC) and proportion indicative of sample zygosity. In some embodiments, nucleotide read and DOC at each SNP position may be calculated, for example by using the mpileup tool in the SAMtools suite or other tools suitable for processing next-generation sequencing data.

In some embodiments, DOC may be used at each sequenced base position to determine statistical confidence intervals for each haplotype call, and the independence of the haplotype call and the DOC may allow a binomial distribution with a mean of $\pi$, where $\pi$ is the proportion of reference calls, and a variance of $n\pi(1-\pi)$ for the population distribution. The proportion may be calculated as the sample proportion (p) of calls that were returned as reference may be calculated as $p=x/n$, where x is the number of times a call is classified as reference and n is the number of times that a given SNP is sequenced or DOC.

At step 514, in some embodiments, the system may determine, based on a distribution of sample zygosities for SNPs in the SNP islands, whether the sample is a single-contributor sample or a multiple-contributor sample. In some embodiments, the distribution of sample zygosities may be determined by the same proportion of the calls. For example, the system may generate a scatterplot for the sample, showing the value p for each SNP position profile of the sample. Genomic SNP position profiles with confidence intervals $p \le 0.1$ may be classified as homozygous variant, $p \ge 0.9$ may be classified as homozygous reference, and $0.4 \le p \le 0.6$ may be classified as heterozygous. By observing whether a significant portion of p values for the sample fall outside the defined ranges, the system may determine whether the sample is a single-contributor or multiple-contributor sample. For example, it may be expected that for a single-contributor sample, all or substantially all or a large majority of p values for the sample will fall within one of the predefined ranges to be defined as homozygous variant, homozygous reference, or heterozygous. However, it may be expected that for a multiple-contributor sample, a substantial portion of p values for the sample will fall outside the predefined ranges and not be classifiable as homozygous variant, homozygous reference, or heterozygous. That is, single-contributor samples may demonstrate three defined zygosity regions for all or substantially all SNP position profiles in all SNP islands, while multiple-contributor samples may demonstrate SNP position profiles having proportions indicative of zygosity falling across the entire observable scope of proportions.

Example

Materials and Methods
State-Based Algorithmic SNP Island Detection

A SNP island target identification algorithm (TIA) was developed as a script using Python version 2.6.6 and utilized allele frequency variant call files from the 1000 Genomes Project Database. Parameters, defined within the algorithm, optimized the number of target regions from the exhaustive options available throughout the human genome. Under SNP island search parameters, suitable target regions were located, consisting of a high-variance segment of sequence with a defined maximal length flanked by low-variance (conserved) segments of sequence of defined minimal length. The parameters dictated the requirements associated with categorizing a segment as being low-variance or high-variance. The maximum length of a high-variance segment, the minimum number of SNPs that a high-variance segment was required to contain, and the minimum length of a low-variance segment are all tunable thresholds within the algorithm. The algorithm maintained a state-based model as it scanned through the genome, with each scanned SNP potentially affecting the state of the model. During genome scanning, there were three active states in which the model existed as 1) establishing low-variance segment I, 2) establishing high-variance segment, and 3) establishing low-variance segment II.

TIA began by scanning the SNP contents of the 1000 Genomes Project database in a SNP-by-SNP manner along the human reference genome to find relevant targets. The algorithm first located a span of at least the specified sequence length where no relevant SNPs existed, establishing the Low-Variance Segment I state. Relevant SNPs were defined as those with a reported global frequency within the threshold of 0.5% to 99.5%. Once this segment was established, TIA began to incrementally count the number of impactful SNPs as it moved along the genome sequence until either the maximal user-defined target window length was reached or a user-defined number of impactful SNPs was reached, establishing the High-Variance Segment state. Impactful SNP targets were defined as those with a reported global frequency within the threshold of 30% to 70% variance. If the maximal target window length was reached first, TIA regressed to the establishing Low-Variance Segment I state. If the impactful SNP target number was reached, TIA advanced to the establishing Low-Variance Segment II state. In this last state, TIA again looked for a span of sufficient base length where no relevant SNPs existed; however, this second span was required to be located before the target window exceeded the maximum allowed region length. If a low-variance segment was not found within the specified region length threshold, TIA regressed to the establishing Low-Variance Segment I state. If a segment of sufficient base length was found, the location of the target window was recorded, and TIA reset to the beginning state, establishing Low-Variance Segment I.

TIA accepts user-defined variables for tailored genome searches, including the minimum length for a low-variance segment, the maximum length of a high-variance segment (identity-linked target window), the frequency range of relevant SNPs based on global SNP frequency, and the minimum number of impactful SNPs to establish a high-variance segment. The TIA process was performed for SNP islands containing a minimum of five, four, and three identity-linked SNPs, occurring within a sequence window of less than 400 bp. Flanking regions were limited to a minimum length of 150 bp.

SNP Island Quality Filtering

SNP island targets containing repeat stretches or patterns of the same nucleotide composition, which potentially interrupt Illumina DNA sequencing chemistries, were separated from the pool of viable targets. This filtering was applied as a post-processing step in the TIA Python script, where each discovered target was subjected to predicate logic that determined its suitability. In the algorithm, all targets were scanned along their sequence length in a 20-base pair sliding window, advancing down the sequence in single-base increments. Within each window, if there existed a cluster of a single nucleotide containing a total of ten bases represented within the window, the target was rejected. A single-nucleotide cluster was defined within the algorithm as a string of four or more of the same nucleotide. Repetitions of short nucleotide patterns, defined as being a unique segment of bases whose length was between 2 and 7 bases, were identified within the SNP islands by comparing the target sequence to itself under that range of base offsets. Any block of sequence with repeating bases of the defined length discovered by this comparison were identified as containing a potential repeating pattern. Each of these segments were examined for repetitious patterns, and if a base pattern was found to occur more than five times consecutively along the sequence, the entire target was rejected.

Primer Design Feasibility Filtering

Primers for targeted amplification of surviving SNP islands were designed to the flanking regions of the targets. A separate Python module was developed and used to evaluate the flanking regions of the SNP islands, determining unique segments within the flanking regions and retaining only those SNP islands meeting the primer stringency criteria for both flanking regions. Though this algorithmic filter is conceptually a single operation, it was performed in a four-step process. The algorithm located all unique subsequences within the flanking regions of all previously identified target regions, as compared to the entire genome. These subsequences had a minimum size range of 15 bp. All SNP islands, lacking unique subsequences in one of the flanking regions, are discarded. The identified unique subsequences from the remaining SNP islands were compared to the human genome reference sequence (version GRCh37.p13; GenBank assembly accession GCA_000001405.14) for similarity of sequence using the BLASTn tool of the National Center for Biotechnology Information. SNP islands were discarded from the viable collection if they that did not contain any flanking region subsequence larger than 25 unique base pairs with no similarity to other regions within the reference genome. Any SNP island with at least one unique sequence for each flanking region was retained.

Validation of SNP Islands for Targeted Amplification within the Human Genome

Human Genomic DNA Preparation

Human genomic DNA (gDNA) was collected from 20 contributors using SecurSwab DUO-V collectors (Bode Technologies). DNA was extracted from the buccal swabs, using the QIAamp DNA Mini Kit (Qiagen) according to the manufacture specifications. The absolute concentration of recovered human gDNA was quantitated by droplet digital polymerase chain reaction (ddPCR). Reactions were constructed using 10 µL of ddPCR Supermix for Probes (No dUTP) (Bio-Rad), 2 U of HindIII (New England Biolabs), and 6 µL of UltraPure DNase/RNase-free water (Thermo Fisher Scientific). 1 µL of each target-specific probe was used within the dual reaction. VIC fluorophore-labeled TaqMan copy number reference probe telomerase reverse transcriptase (TERT) (Thermo Fisher Scientific) was used as a single-target autosomal marker, and FAM fluorophore-labeled TaqMan copy number probe sex-determining region Y (SRY) (Thermo Fisher Scientific) was used as a single-target Y-chromosome sex-linked marker. Buccal swab DNA (4 µL) was evaluated within their respective reactions for a dilution range of $10^{-2}$, $10^{-3}$, and $10^4$.

Droplets were generated using Automated Droplet Generation Oil for Probes (Bio-Rad) in an Automated Droplet Generator (Bio-Rad). Droplets were amplified using a C1000 Touch Thermal Cycler (Bio-Rad). Droplets were evaluated for target-amplified fluorescence using a QX200 Droplet Reader with excitation wavelengths at 494 nm (FAM) and 538 nm (VIC). Data acquisition and analysis were performed on two fluorescence channels (518 nm and 554 nm) using the QuantaSoft software (Bio-Rad), where concentrations (copies/µL) of the TERT and SRY targets were calculated. Reactions were performed in triplicate, and measured DNA concentrations were converted from copies/µL to pg/µL using the conversion estimate of 3.3 pg/haploid copy of the human genome.

Targeted Validation and Multiplex Amplification of SNP Island Primers

Primer sets were computationally designed for the unique sequences of the low-variance SNP island flanking regions using the SeqBuilder module of the DNASTAR software suite (version 11.2.1.25). During the searches, primer length range was set to between 25 and 45 bp with a target melting temperature (Tm) of 70° C. Identified primers were compared to the NCBI GenBank database human reference genome (version GRCh37.p13) using BLASTn.

Targeted singleplex polymerase chain reaction (PCR) with primer sets designed to select for SNP islands was used to selectively amplify SNP islands to the exclusion of the remainder of the genome. 25-µL amplification reactions were composed of 25 ng of human gDNA, 0.5 U of Phusion High-Fidelity DNA polymerase (New England Biolabs), deoxynucleotide triphosphate (dNTP) mix (Thermo Fisher Scientific) at 200 µM each, forward and reverse primers at 0.5 µM. The thermal cycle conditions were 98° C. for 3 min, followed by 40 cycles of 98° C. for 10 sec, 70° C. for 3 min, and 72° C. for 1 min, with a final extension at 72° C. for 5 min. After amplification, amplicons were cleaned using the ChargeSwitch PCR Purification Kit (Thermo Fisher Scientific) according to manufacturer specifications. The primer specificities and amplicon sizes were evaluated using a DNA 1000 assay chip (Agilent Technologies) on a BioAnalyzer 2100 (Agilent Technologies).

Multiplexed targeted amplification was used to amplify SNP island profiles from the gDNA of 20 contributing individuals. Contributor gDNA for each individual was amplified in two multiplexed reactions, containing 26 primer sets per reaction. Each reaction (50 µL total volume) was composed of 25 ng of contributor DNA, 1 U of Phusion High-Fidelity DNA polymerase, 400 µM of each dNTP, and 0.5 µM of both forward and reverse primers for 26 SNP island targets. Thermal cycle conditions were the same as those used for singleplex reactions. After amplification, multiplex reactions for each individual were combined. The pooled multiplex reactions were cleaned using AMPure XP reagent (Beckman Coulter), using a 1.8× bead to total volume ratio and eluting in a volume of 50 µL of UltraPure DNase/RNase-free water.

Illumina MISEQ Amplicon Sequencing

Illumina paired-end sequencing libraries were prepared using the Accel-NGS 2S DNA Library kit for Illumina Platforms (Swift Biosciences), following manufacturer specifications. Each individual DNA pool was given a unique multiplex identifying adapter (MID). Quality and concentration evaluations for amplicon pools, pre- and post-adapter addition, were visualized using a DNA 1000 Assay chip on a BioAnalyzer 2100. Library quality was assessed using the ddPCR Library Quantification Kit for Illumina TruSeq, according to manufacturer specifications, on the Bio-Rad ddPCR platform. Prepared libraries were sequenced on an Illumina MiSeq platform at the Institute for Genome Sciences (IGS) Genomics Resource Center at the University of Maryland School of Medicine. The libraries were sequenced in a paired-end manner using the MiSeq Reagent Kit v3 (I lumina, Inc.), generating 300 bp read lengths.

Computational Post-Processing of DNA Sequence Reads

Paired sequence read files generated from Illumina sequencing were organized and binned into paired sample-specific files according to MID sequences. The paired files were evaluated and trimmed based on sequence quality using Trimmomatic in paired-end mode. Low quality sequences, sequencing artifacts, sequencing adapters, and MIDs were removed from the reads. The Trimmomatic filter settings included seed mismatches set to 0, palindrome clip threshold set to 40, simple clip threshold set to 15 bp, minimal adapter length set at 8 bp, Phred values set to 20 for leading and trailing bases, sliding window length set to 4 bp with Phred score set to 25, and the minimum length of a read set to 70 bp.

Quality-trimmed reads for each sample were aligned in a paired-end sequence alignment to the human reference genome (version GRCh37.p13) using the Burrows-Wheeler Aligner Maximal Exact Matches (BWA-MEM) program. The resulting sequence/alignment map (SAM) files were revised directly with a Python script to remove any sequences extraneous to the SNP island targets, producing a new SAM file with the remaining sequences. The SAM file was converted to a sorted binary sequence/alignment map (BAM) file using the import command of the SAMtools suite version 0.1.19. The BAM files were sorted and indexed with the sort and index commands of the SAMtools suite, respectively.

SNP calls were performed using the sorted and indexed BAM files in the Genome Analysis Tool Kit Haplotype Caller (GATK HC) and output as allele files in variant call file format. Nucleotide read and depth of coverage (DOC) at each SNP position were calculated using the mpileup tool in the SAMtools suite, creating target pileup histograms.

SNP Profile Analysis

The depth of sequence coverage (DOC) at each sequenced base position was used to determine statistical confidence intervals for each haplotype call for each sample. The independence of the haplotype call and the DOC allowed a binomial distribution with a mean of it, where it is the proportion of reference calls, and a variance of $n\pi(1-\pi)$ for the population distribution. The sample proportion (p) of calls that were returned as reference was calculated as $$p = x/n$$

where x is the number of times a call is classified as reference and n is the number of times that a given SNP is sequenced or DOC. To determine if the sample size was large enough to use the normal distribution to calculate a statistical confidence interval for the sample proportion, the criteria $$(1-p) \geq 10$$

was used. If this condition was met, then the use of the normal distribution was determined to be appropriate; otherwise, a confidence interval was not calculated. The confidence interval for the population proportion (n) for all sample proportions that met the sample size criterion was calculated using $$p \pm Z^{\alpha}/2 \sigma p,$$

where the standard deviation of p is $$\sigma_p = \sqrt{\frac{p(1-p)}{n}}$$

and for a 95% confidence level a=0.5 and Z=1.96. Z is a standardized normal random variable with a mean of 0 and a standard deviation of 1. Z measures number of standard deviations that an observation is from the mean. For a 95% confidence level (CL), α=1−CL=0.5. The corresponding Z value is 1.96, which is found using a standard normal probability distribution table.

The distribution of haplotype calls for SNP classifications within a given profile was visualized by scatterplot of the sample p and the confidence limits (margin of error) for each SNP location using the ggplot2 package and by marginal histogram using the ggExtra package of the R statistical software. Genomic SNP position profiles with confidence intervals that included or were less than p≤0.1 were classified as homozygous variant, that included or were greater than p≥0.9 were classified as homozygous reference, and that included 0.4≤p≤0.6 were classified as heterozygous.

The relation of the SNP profiles between the individuals was visualized based on the zygosity determination for each SNP location. SNP profile calls were assigned values of 1 for the homozygous reference zygosity, 2 for the heterozygous zygosity, or 3 for the homozygous variant zygosity. A total of 116 SNP locations within 28 SNP islands for each profile were evaluated. The relationships between the zygosity profiles of identity-relevant SNP locations for fifteen individual genomic samples were evaluated by the percent similar calculated as the number of matched SNP calls divided by the total number of calls between the individual pair.

A haplotype heatmap and relatedness dendrogram were generated using the heatmap.2 function of the gplots package of the R statistical software. The zygosity of each evaluated SNP location for each profile is represented as a green band (homozygous reference), a yellow band (heterozygous), or a red band (homozygous variant) as shown in FIGS. 9A and 9B. The Euclidean distance of the relatedness of the SNP zygosity profiles and the complete agglomeration method for clustering were used to construct an agglomerative hierarchical clustering dendrogram.

Results

Algorithmic Identification of Identity-Linked SNP Islands

Using the parameters for identity-linked SNP island discovery, the computational algorithms developed within this study located 52 qualifying SNP islands for use with the Illumina MPS platform chemistry. In a stepwise manner, the target identification filter (79,154 targets remain), sequence repetition rejection filter (29,465 targets remain), and the primer design feasibility filter (54 targets remain) narrowed the scope of regions for targeted SNP island amplification within the genome (as shown in FIG. 6).

FIG. 6 shows identity-linked SNP island identification within the human genome using computational algorithms. The human reference genome (version GRCh37.p13) was computationally filtered for unique, identity-linked SNP islands, containing a minimum of 5, 4, or 3 identity-relevant SNPs. SNP islands amenable to analysis by Illumina sequencing chemistries and to targeted amplification from the genome were located using a target identification filter, a sequence repetition rejection filter, and a primer design feasibility filter.

Twelve 5-SNP islands, eight 4-SNP islands, and thirty-four 3-SNP islands were identified. A total of 314 identity-relevant SNPs, including those identified within the 1000 Genomes Project Database, were located within the SNP islands (as shown in the table in FIGS. 7A-7N).

FIGS. 7A-7N show a table showing identity-linked SNP and SNP island genomic locations. Reported global allele frequencies are those represented within the 1000 Genomes Project Database. For SNP loci labeled NSV, no SNP variant was previously reported for that genomic location. Deletion events are represented as a dash (-).

Genomic DNA Sample Preparations and SNP Island Validations

Computational prediction produced 90 unique primer sets, designed for the 52 SNP islands identified in the filtering algorithms. Primer pairs amplifying more than one region or unexpected amplicon sizes from genomic DNA, using described conditions in singleplex PCRs, were eliminated as non-targeted for the desired SNP island region. As a result, 53 targeted primer sets were functionally accepted (as shown in FIGS. 7A-7N).

MiSeq Run Summary Statistics

Figure 8:
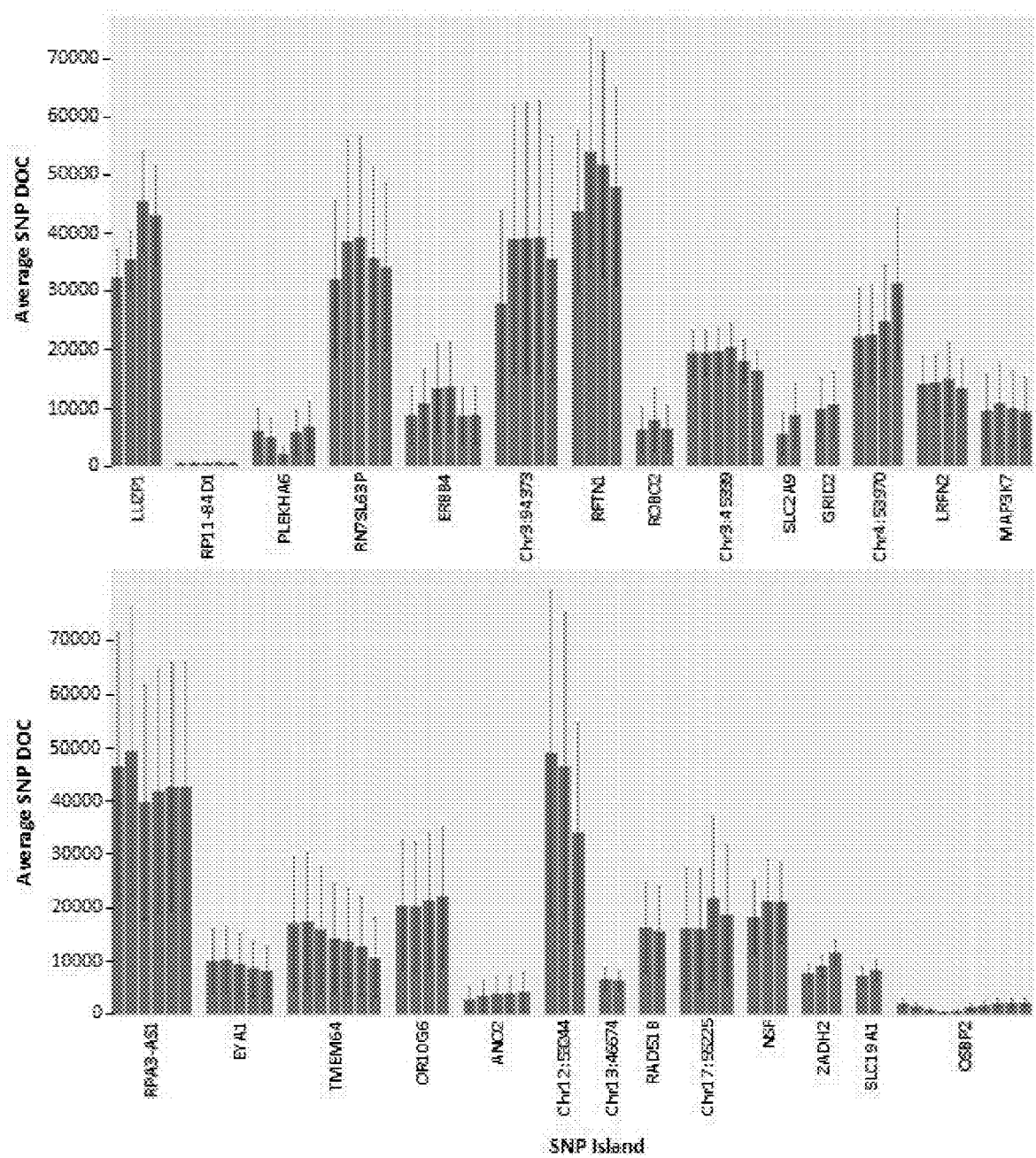
FIG. 8 is a depiction of the average depth of coverage (DOC) for identity-linked SNP locations for SNP island targets, in accordance with some embodiments.

The sequence evaluation of SNP island amplicons using the Illumina MiSeq DNA sequencing platform identified 12,379,802 sequence reads (3,714 megabases) at an average trimmed read length of 240 bp. FIG. 8 illustrates the average depth of coverage (DOC) for each identity-linked SNP location for each SNP island target. The depth of coverage (DOC) for each identity-linked SNP location within each SNP island was averaged across all contributing individuals. Error bars represent variance within a 95% confidence interval.

Zygosity Profile Determination

Using the depth of coverage for each SNP location, a proportion indicative of sample zygotity for each SNP location was determined and plotted in a scatterplot for each sample.

Figure 9:
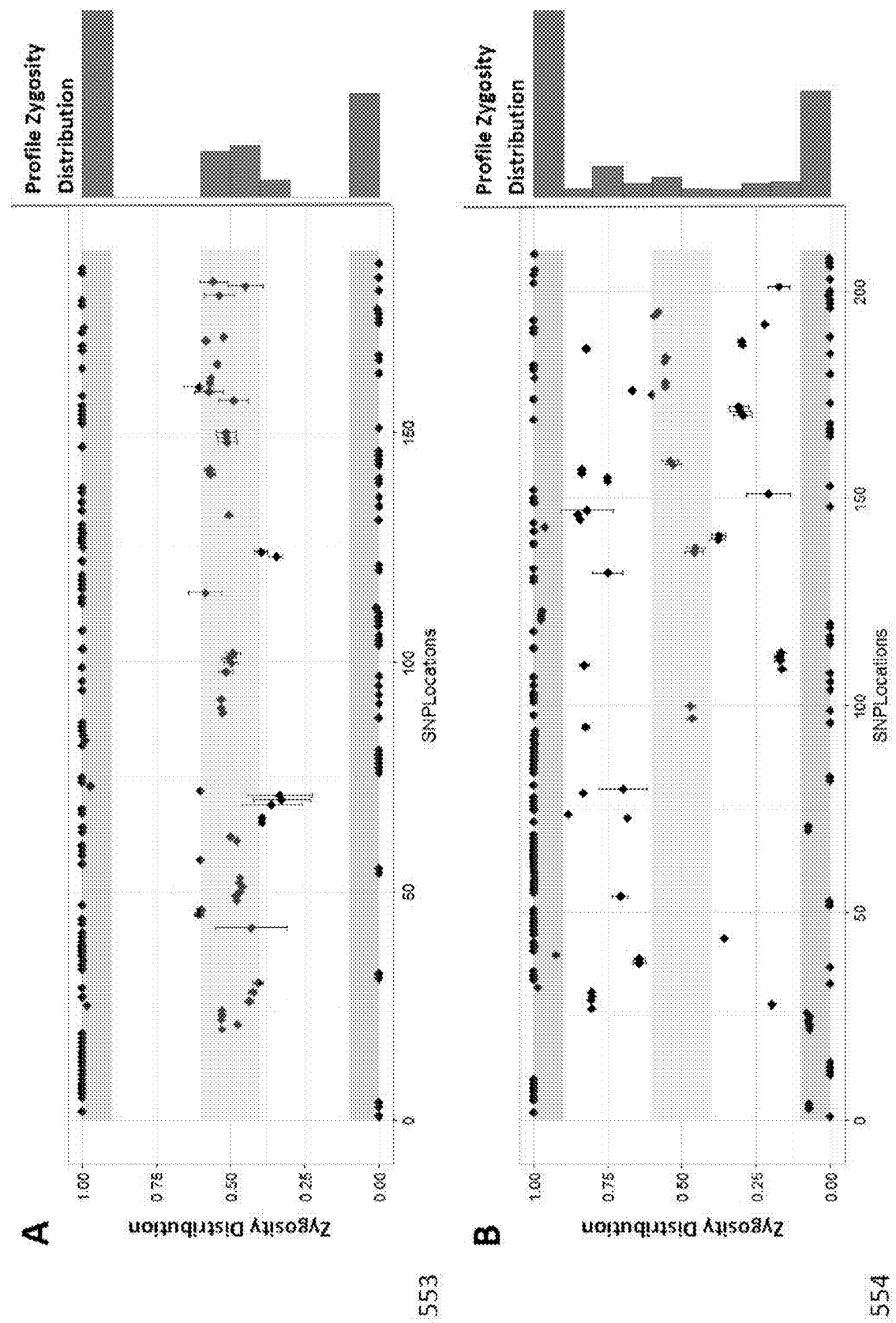
FIG. 9 is a plot showing a zygosity comparison between a single-contributor sample (part A) and a multiple-contributor sample (part B)

FIG. 9 shows zygosity comparison between a single-contributor and a multiple-contributor sample. Depth of coverage for SNP calls was used to determine the proportion (p) of the zygosity of the given SNPs within the profiles. Visualization of the zygosity proportions across the entire SNP profile as they map to defined zygosity regions allows the differentiation of single- and multiple-contributor samples. The plotted proportions of the single-contributor sample (A) constrain to the defined regions of homozygous reference (0.9-1.0 p, green band), heterozygous (0.4-0.6 p, yellow band), or homozygous variant (0-0.1 p, red band) for the evaluated SNP locations. The plotted proportions of the multiple-contributor sample (B) are distributed widely between the homozygous extremes and are not constrained to the defined zygosity regions.

FIG. 9 illustrates the variation that is observable between a single-contributor and mixed-contributor (1:1 ratio) sample. The zygosity proportion for each SNP location in the single-contributor sample of part A of FIG. 9 falls within the defined regions considered appropriate for zygosity calls of homozygous reference (0.9-1.0 p, green band), heterozygous (0.4-0.6 p, yellow band), and homozygous variant (0-0.1 p, red band). Part B of FIG. 9 illustrates the variability in depth of coverage and, as a result, the proportion of zygosity call for each SNP location with many of the SNP calls falling outside the defined regions of expected zygosity. In comparison of the profile zygosity proportion distributions between the two samples, the single-contributor sample contains proportions that create three defined zygosity regions within the distribution, while the multiple-contributor sample contains representation across the scope of observable zygosity proportion.

As a result of the algorithmic genome filtering and individual sequence analyses, a total of 314 identity-linked SNPs were identified (as shown in the table in FIGS. 7A-7N). Of those, 167 SNPs were previously characterized within the 1000 Genomes Project Database and fell within the global population frequency range of 30%-70%. 55 of the SNPs were defined but fell outside of the filtered range, and 18 of the SNPs were characterized but contained no global population frequency information within the database. 74 of the SNP locations were identified within this study and were not represented within the 1000 Genomes Project Database.

Profile Comparative Analysis

Figure 10:
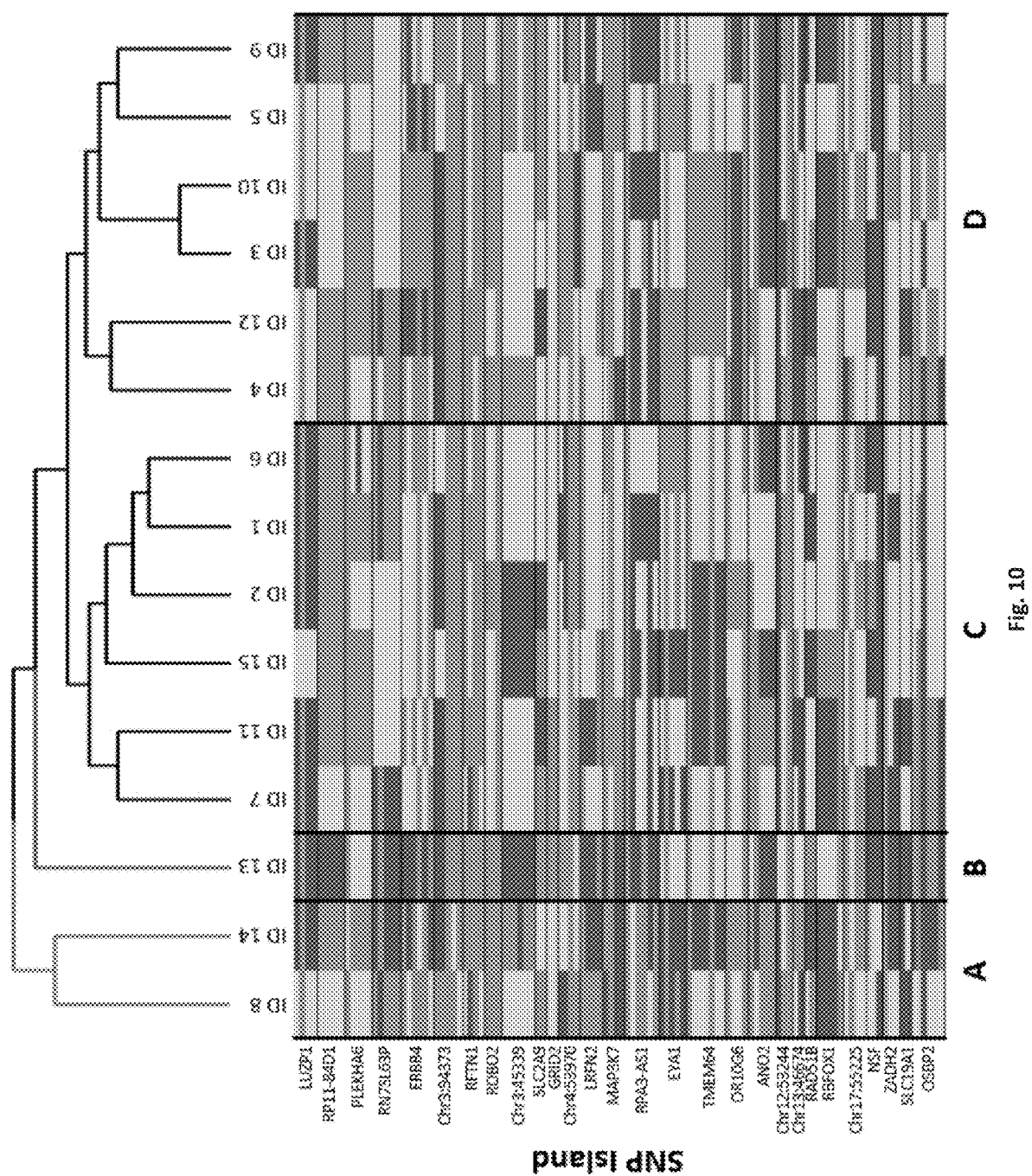
FIG. 10 is a depiction of zygosity profile comparison at identity-linked loci, in accordance with some embodiments.

Fifteen single-contributor SNP profiles (116 identity-relevant SNP locations) generated from the identity-linked SNP islands were evaluated for similarity (as shown in the table in FIG. 11, discussed further below) and SNP profile relatedness (as shown in FIG. 10).

FIG. 10 shows zygosity profile comparison at identity-linked loci. Zygosity comparisons, using the identity-linked SNP island panel compiled with algorithms of this study, differentiated the genomes of fifteen individuals. A total of 116 SNP locations within 28 SNP islands were evaluated in the heatmap profile comparison with homozygous reference zygosity represented as a green band, heterozygous zygosity represented as a yellow band, and homozygous variant zygosity represented as a red band. The accompanying agglomerative hierarchical clustering dendrogram represents the Euclidean distance of profile relatedness between the individual SNP zygosity profiles, resulting in three branches denoted in the dendrogram as green, red, and black lines. Three clusters (A, C, and D) and one outlying singleton (B) were identified.

Each individual was uniquely identified from all other individuals to varying degrees in the comparisons. The table in FIG. 11 shows a similarity matrix of SNP data for evaluated individuals. Haplotype similarities of samples ID1-ID15 for each SNP location are represented beneath the diagonal, while the numbers of SNP haplotypes shared between pairs of samples are above the diagonal.

The similarity, represented in the table in FIG. 11, revealed the highest similarity between two profiles within the total fifteen profiles to be 82% similar and the lowest profile to be 35% similar. For the pool of SNP profiles, the typical profile similarities were between 40% and 59% similar. The heatmap of the SNP profile relatedness of fifteen individuals (as shown in FIG. 10) illustrates the similarities and differences for each profile at each SNP location evaluated. The results indicate that each individual has a unique SNP profile as compared to others in the pool. The agglomerative hierarchical clustering dendrogram of SNP profile relatedness is represented by three branches containing three clusters and one outlying singleton.

Discussion

Fifty-two SNP islands with utility for differentiating human identity were identified using a state-based computational algorithm to filter through the genome. SNPs within the islands were selected to provide representation within the human population with a frequency that allows general variability but not niche specificity that would select for a highly-specific population. The islands were computationally targeted in compact regions of the genome (≤400 base pairs in length) containing a minimum of three to five SNPs with a SNP frequency between 30-70% for the global population as defined by data from the 1000 Genomes Project. For the overall genomic target region, each island was further required to be flanked by low-variance regions of at least 150 bp, only containing SNPs with frequencies of ≤0.5% or ≥99.5%. The identified regions were down-selected for unique genome locations with conserved primer targeting sites within the flanking regions as compared to the whole genome. These conserved primer sites allow target-specific amplification of the SNP islands while minimizing noise, resulting in increased target sequence resolution. Within the SNP islands, 167 markers for identity passed computational filters, experimental amplification, and massively parallel DNA sequencing. An additional 147 SNPs were identified within the SNP islands as providing identity-relevant information. Application of the resulting SNP array to contributor genomic DNA produced profiles of the contributing individuals that were targeted and reproducible. Using this SNP array, 15 individual identity profiles were obtained from trace DNA samples (~5 pg) and confirmed using buccal swab DNA samples (~10 ng).

Each SNP island contained a minimum of 3, 4, or 5 identity-relevant SNPs as determined by global frequency calculations represented within the 1000 Genomes Project Database. As the SNP profiles of individual contributors were defined for the SNP island regions, 147 identity-relevant SNPs were recognized beyond those selected by the algorithms. In some instances, these additional SNPs did not meet the thresholds defined by the algorithmic filters of 30%-70% global frequency, and, in other instances, the SNPs were not defined within the 1000 Genomes Project Database, indicating previously undefined SNPs (as shown in the table in FIGS. 7A-7N). These results highlight the known limitations of databases like the 1000 Genomes Project Database for under-representing the SNP allele frequencies of the global human population. Expansion of the 1000 Genomes Project Database and other similar databases has been noted as providing a greater resolution to the global human genome variance. As these type databases continue to expand, the numbers of identified SNPs and their global population frequencies associated with them will gain in fidelity.

Figure 12:
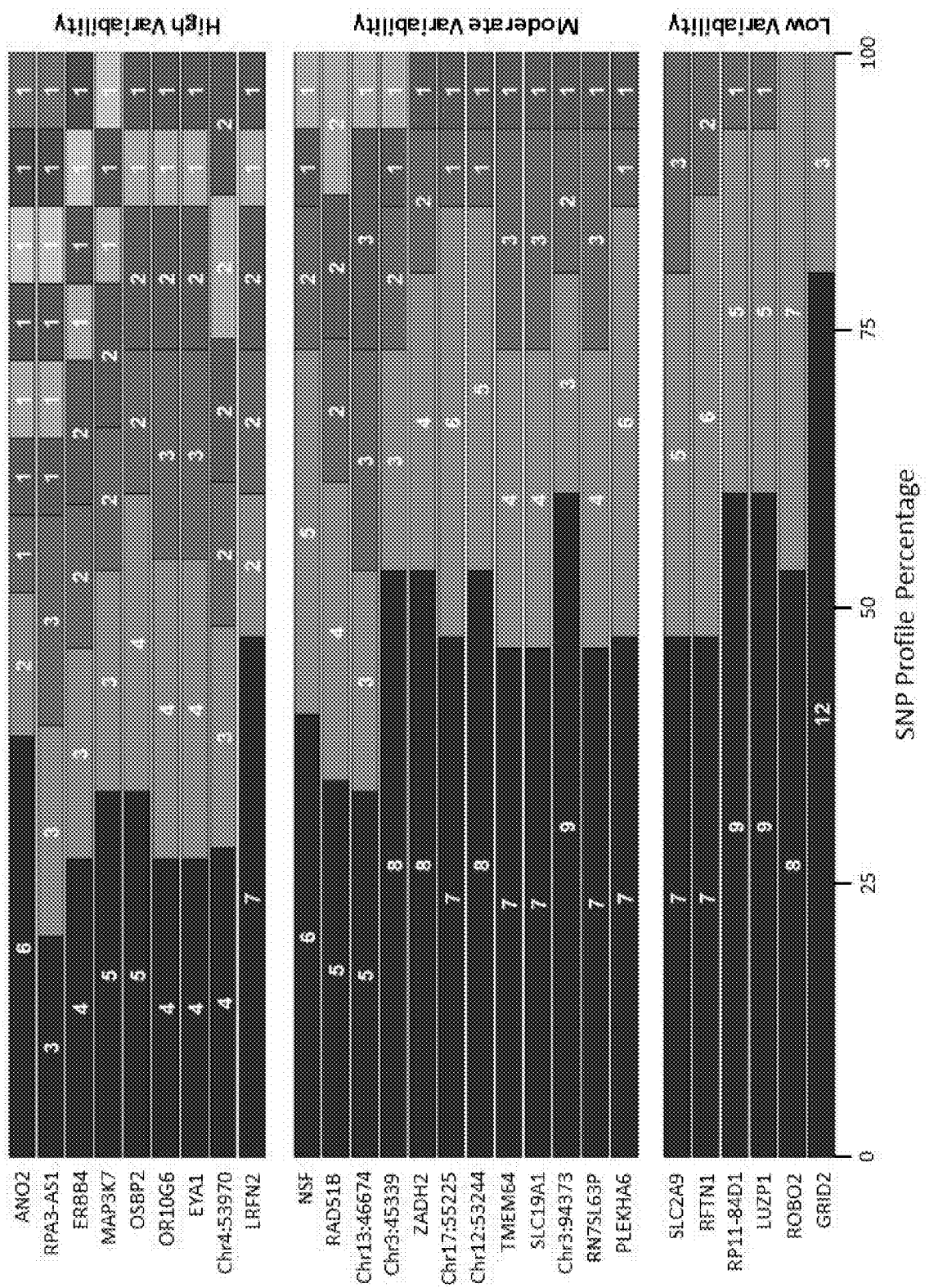
FIG. 12 is a depiction of profile variance within SNP islands across individuals, in accordance with some embodiments.

Evaluation of the SNP islands used to differentiate fifteen individuals provided insight into the degree of individual discerning power within each SNP island (as shown in FIG. 12). FIG. 12 shows profile variance within SNP islands across individuals. The SNP profile for each individual at the SNP island level was evaluated to determine the variability of SNP profiles within SNP islands. SNP islands are grouped as containing high variability (≥6 species), moderate variability (4-5 species), and low variability (≤3 species) according to the numbers of haplotype island species observed across all individuals. The numbers within the bars represent the absolute number of observed SNP island species.

As anticipated, there was varying efficiencies between regions chose for SNP islands, observing variance at low, moderate, and high occurrences. Of the islands evaluated, ERBB4, MAP3K7, RPA3-AS1, and ANO2 contain a higher profile variance than other SNP islands, indicating a higher recombination frequency within the sequences of those islands.

Increasing the number of identity-relevant SNPs contained within each sequenced target provided more identity-discerning information for each SNP island. In the evaluation of the identity-linked SNP islands across the genomes of fifteen individuals, the SNP variation, contained within a subset of the total number of SNP islands, effectively differentiated the identities of all individuals (as shown in the table in FIG. 11; and as shown in FIG. 10). Evaluating the SNP location DOC statistics from the MPS run also provided a means to differentiate between single-contributor and multiple-contributor samples (FIG. 9). The zygosity proportion distribution for the single-contributor sample conformed tightly to the three expected zygosity determinant regions of homozygous reference (0.9-1.0 p), heterozygous (0.4-0.6 p), and homozygous variant (0-0.1 p). The variance from the three expected zygosity determinant regions observed for the multiple-contributor sample indicated a mixed sample with alternate DOCs and the resulting distribution proportions overlaying each other. In comparison of 15 contributor samples, the similarity of the resulting evaluated SNP profiles produces a typical similarity score between 40% and 59% (as shown in the table in FIG. 11). This observed range falls well within the global SNP frequency range of 30% to 70% targeted by the TIA, indicating that the algorithms effectively selected identity-relevant SNP targets. The heatmap representation and accompanying dendrogram of the individual SNP profiles (as shown in FIG. 10) provides a means to visualize the individual SNP location differentiation between the SNP profiles while grouping the profiles by overall relatedness. While distinct groups were observed, each individual profile was easily differentiated from all other profiles. In an additional application of the SNP islands for the differentiation of related individuals (data not shown), the identity-linked SNPs uniquely identified individuals of sibling and parent-child pairs.

The algorithmic narrowing of the scope of genomic regions provided SNP island options conducive to analysis by targeted amplification. In addition, the algorithms allowed the efficient evaluation of the greater human genome for regions that were amenable to uniquely identifying individual contributors within the Illumina MPS workflow. These algorithms were developed in a manner that makes them tunable for determining the desired genomic features. The operator can change the maximum length of the SNP island; the minimum length of the low-variance primer regions; the number, frequency, and type of repeat sequences allowed within the SNP island; and the minimum number of known SNPs having a defined global or population-specific frequency range. By tuning the algorithms to desired target goals, the resulting SNP panel can be applied to discovery of identity-, ancestry-, or phenotype-linked information. In addition, the islands can be modified to accommodate the requirements and advantages of other sequencing platform chemistries.

Systems and methods like ForenSeq for the Illumina MPS platform and Ion AmpliSeq HID SNP panel for human identification for the Ion Personal Genome Machine MPS platform are under evaluation for application in genetic profiling within forensic casework. While these methods provide a standardized, pre-defined methodology for determining a given individual profile, the systems are limited in the ability to tailor the assays for differentiations at higher resolution and with regard to multiple contributor samples. The advantages of the SNP target identification algorithm and quality filtering algorithms are that they allow the user to develop tailored SNP islands, according to SNP allele frequency and population information. As a result, the algorithms provide flexibility to rapidly identify and validate new informative SNP panels as global population SNP databases mature and gain in fidelity.

CONCLUSION

The techniques discussed herein have occasionally been discussed with respect to human genetic information or human DNA, but the techniques may be equally applicable to genetic information or DNA from other organisms including animals, plants, bacteria, and viruses, provided sufficient information is available regarding a reference genome and/or the locations of SNPs in the reference genome. In organisms that are more rapidly evolving than humans and other mammals, such as bacteria and viruses, it may be advantageous to repeatedly execute and re-execute the methods disclosed herein in response to rapid changes in the reference genome or in the population from which samples are drawn.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

What is claimed is:

1. A method for determining a location in a nucleic acid sequence for which to design one or more primers, comprising:
   receiving a nucleic acid sequence from one or more DNA samples;
   scanning the nucleic acid sequence from the one or more DNA samples and determining locations of a plurality of single-nucleotide polymorphisms (SNPs) in the sequence;
   scanning the nucleic acid sequence from the one or more DNA samples to locate a first region, a second region, and a third region, wherein the second region includes a plurality of SNP locations that satisfy a first predefined criteria, and wherein the first and third regions flank the second region;
   determining a location within one of the first and third regions for which to design a primer for amplification of a region of the nucleic acid sequence that includes the plurality of SNP locations that satisfy the first predefined criteria, wherein the determination comprises selecting a location that minimizes a likelihood of a primer designed for amplification of the second region of the nucleic acid sequence that includes the plurality of SNP locations that satisfy the first predetermined criteria amplifying the nucleic acid sequence outside of the second region;
   generating a primer for the determined location;
   amplifying the determined location using the generated primer to generate a plurality of amplicons for the one or more DNA samples; and
   sequencing and aligning each amplicon of the plurality of amplicons to generate one or more representations of each DNA sample of the one or more DNA samples, wherein generating one or more representations of each DNA sample includes generating and storing in a memory of a computing device one or more sequence alignment maps for each DNA sample.

2. The method of claim 1, wherein scanning the nucleic acid sequence to locate the first region, the second region, and the third region comprises:
   determining whether a first segment of the nucleic acid sequence contains fewer than or equal to a first number of SNP locations that satisfy a second predefined criteria;
   in accordance with a determination that the first segment contains fewer than or equal to the first number of SNP locations that satisfy the second predefined criteria, determining whether a second segment of the nucleic acid sequence, adjacent to and immediately following the first segment, contains at least a second number of SNP locations that satisfy the first predefined criteria;
   in accordance with a determination that the second segment contains at least the second number of SNP locations that satisfy the first predefined criteria, determining whether a third segment of the nucleic acid sequence, adjacent to and immediately following the second segment, contains fewer than or equal to a third number of SNP locations that satisfy the second predefined criteria; and
   in accordance with a determination that the third segment contains fewer than or equal to the third number of SNP locations that satisfy the second predefined criteria, determining that the first segment is the first region, that the second segment is the second region, that the third segment is the third region.

3. The method of claim 2, wherein:
   the first segment is at least a first minimum length;
   the second segment is at most a maximum length; and
   the third segment is at least a second minimum length.

4. The method of claim 2, wherein:
   the first segment is at least a first minimum length;
   the second segment is at most a maximum length; and
   the third segment is at least the first minimum length.

5. The method of claim 2, wherein the second predefined criteria comprises whether a SNP location is a base in the nucleic acid sequence having a SNP occurring in more than a first minimum percentage of a population and less than a first maximum percentage of the population.

6. The method of claim 1, wherein the first predefined criteria comprises whether a SNP location is a base in the nucleic acid sequence having a SNP occurring in more than a second minimum percentage of a population and less than a second maximum percentage of the population.

7. The method of claim 1, wherein the first predefined criteria comprises whether a SNP location is a base in the nucleic acid sequence having a SNP associated with a phenotype.

8. The method of claim 1, wherein the first predefined criteria comprises whether a SNP location is a base in the nucleic acid sequence having a SNP associated with a medical condition.

9. The method of claim 1, wherein determining the location within one of the first and third regions for which to design the primer comprises:
   comparing the first and third regions to the remainder of the nucleic acid sequence to locate a unique sub-segment in one of the first and third regions, wherein the unique sub-segment has at least a third minimum length and is not replicated elsewhere in the nucleic acid sequence; and
   determining that the unique sub-segment is the location at which to design a primer.

10. The method of claim 9, wherein determining the location within one of the first and third regions for which to design the primer comprises:
    determining that the unique sub-segment does not have a similarity above a similarity threshold to any other portion of the remainder of the nucleic acid sequence.

11. The method of claim 1, wherein determining the location within one of the first and third regions for which to design the primer comprises:
    determining that the first and third regions do not contain more than a fourth number of consecutive identical nucleotides.

12. The method of claim 1, wherein determining the location within one of the first and third regions for which to design the primer comprises:
    determining that the first and third regions do not contain one or more predefined patterns.

13. The method of claim 1, wherein scanning the nucleic acid sequence to locate the first region, the second region, and the third region comprises:
    determining whether a first segment of the nucleic acid sequence contains fewer than or equal to a first number of SNP locations that satisfy a second predefined criteria;
    in accordance with a determination that the first segment contains fewer than or equal to the number of SNP locations that satisfy the second predefined criteria, determining whether a second segment of the nucleic acid sequence, adjacent to and immediately following the first segment, contains at least a second number of SNP locations that satisfy the first predefined criteria; and in accordance with a determination that the second segment contains at least the second number of SNP locations that satisfy the first predefined criteria, determining whether a third segment of the nucleic acid sequence, adjacent to and immediately following the second segment, contains fewer than or equal to a third number of SNP locations that satisfy the second predefined criteria;

in accordance with a determination that the third segment does not contain fewer than or equal to the third number of SNP locations that satisfy the second predefined criteria, determining whether a fourth segment of the nucleic acid sequence, following but not immediately adjacent to the second segment, contains fewer than or equal to the third number of SNP locations that satisfy the second predefined criteria; and in accordance with a determination that the fourth segment contains fewer than or equal to the third number of SNP locations that satisfy the second predefined criteria, determining that the first segment is the first region, that the fourth segment is the third region, and that a fifth segment spanning from the beginning of the second segment to immediately before the beginning of the fourth segment is the second region.

14. A system for determining a location in a nucleic acid sequence for which to design one or more primers, comprising:

a processor; and memory storing instructions that, when executed by the processor, cause the system to:

receive a nucleic acid sequence from one or more DNA samples;

scan the nucleic acid sequence from the one or more DNA samples and determine locations of a plurality of single-nucleotide polymorphisms (SNPs) in the sequence;

scan the nucleic acid sequence from the one or more DNA samples to locate a first region, a second region, and a third region, wherein the second region includes a plurality of SNP locations that satisfy a first predefined criteria, and wherein the first and third regions flank the second region;

determine a location within one of the first and third regions for which to design a primer for amplification of a region of the nucleic acid sequence that includes the plurality of SNP locations that satisfy the first predefined criteria, wherein the determination comprises selecting a location that minimizes a likelihood of a primer designed for amplification of the second region of the nucleic acid sequence that includes the plurality of SNP locations that satisfy the first predetermined criteria amplifying the nucleic acid sequence outside of the second region;

generate a primer for the determined location;

amplify the determined location using the generated primer to generate a plurality of amplicons for the one or more DNA samples; and sequence and aligning each amplicon of the plurality of amplicons to generate one or more representations of each DNA sample of the one or more DNA samples, wherein generating one or more representations of each DNA sample includes generating and storing in a memory of a computing device one or more sequence alignment maps for each DNA sample.

15. A non-transitory computer readable storage medium storing instructions that, when executed by a system comprising a processor, cause the system to:

receive a nucleic acid sequence from one or more DNA samples;

scan the nucleic acid sequence from the one or more DNA samples and determine locations of a plurality of single-nucleotide polymorphisms (SNPs) in the sequence;

scan the nucleic acid sequence from the one or more DNA samples to locate a first region, a second region, and a third region, wherein the second region includes a plurality of SNP locations that satisfy a first predefined criteria, and wherein the first and third regions flank the second region;

determine a location within one of the first and third regions for which to design a primer for amplification of a region of the nucleic acid sequence that includes the plurality of SNP locations that satisfy the first predefined criteria, wherein the determination comprises selecting a location that minimizes a likelihood of a primer designed for amplification of the second region of the nucleic acid sequence that includes the plurality of SNP locations that satisfy the first predetermined criteria amplifying the nucleic acid sequence outside of the second region;

generate a primer for the determined location;

amplify the determined location using the generated primer to generate a plurality of amplicons for the one or more DNA samples; and sequence and aligning each amplicon of the plurality of amplicons to generate one or more representations of each DNA sample of the one or more DNA samples, wherein generating one or more representations of each DNA sample includes generating and storing in a memory of a computing device one or more sequence alignment maps for each DNA sample.

* * * * *

SEQUENCE LISTING

```
<160> NUMBER OF SEQ ID NOS: 120

<210> SEQ ID NO 1
<211> LENGTH: 38
<212> TYPE: DNA
<213> ORGANISM: Artificial Sequence
<220> FEATURE:
<223> OTHER INFORMATION: Synthetic Construct

<400> SEQUENCE: 1
tacttgactt ccgttgccaa gcacgtgtcc cctcttgc                           38

<210> SEQ ID NO 2
<211> LENGTH: 40
<212> TYPE: DNA
<213> ORGANISM: Artificial Sequence
<220> FEATURE:
<223> OTHER INFORMATION: Synthetic Construct

<400> SEQUENCE: 2
```
tcctcagcat aagcgggaac gactccggaa cagggagttt                              40

<210> SEQ ID NO 3
<211> LENGTH: 40
<212> TYPE: DNA
<213> ORGANISM: Artificial Sequence
<220> FEATURE:
<223> OTHER INFORMATION: Synthetic Construct

<400> SEQUENCE: 3
atccatgggt ggtgtcacta aacgttcgtg ttgtcttctc                              40

<210> SEQ ID NO 4
<211> LENGTH: 40
<212> TYPE: DNA
<213> ORGANISM: Artificial Sequence
<220> FEATURE:
<223> OTHER INFORMATION: Synthetic Construct

<400> SEQUENCE: 4
tcctcagcat aagcgggaac gactccggaa cagggagttt                              40

<210> SEQ ID NO 5
<211> LENGTH: 38
<212> TYPE: DNA
<213> ORGANISM: Artificial Sequence
<220> FEATURE:
<223> OTHER INFORMATION: Synthetic Construct

<400> SEQUENCE: 5
tgctttggag acctagagaa ccagggttta gctgtatc                                38

<210> SEQ ID NO 6
<211> LENGTH: 42
<212> TYPE: DNA
<213> ORGANISM: Artificial Sequence
<220> FEATURE:
<223> OTHER INFORMATION: Synthetic Construct

<400> SEQUENCE: 6
tttaaggcag cggggctgtt ggatgaccgt cctttctct ta                            42

<210> SEQ ID NO 7
<211> LENGTH: 42
<212> TYPE: DNA
<213> ORGANISM: Artificial Sequence
<220> FEATURE:
<223> OTHER INFORMATION: Synthetic Construct

<400> SEQUENCE: 7
acttacaaca actggagttt ggcttgtcaa gagtcgtgca ga                           42

<210> SEQ ID NO 8
<211> LENGTH: 41
<212> TYPE: DNA
<213> ORGANISM: Artificial Sequence
<220> FEATURE:
<223> OTHER INFORMATION: Synthetic Construct

<400> SEQUENCE: 8
actgtctgtg ctcaattacc tgctcctaca ccatcctaca c                            41

<210> SEQ ID NO 9
<211> LENGTH: 41
<212> TYPE: DNA
<213> ORGANISM: Artificial Sequence

```
<220> FEATURE:
<223> OTHER INFORMATION: Synthetic Construct

<400> SEQUENCE: 9
acctgcccac actcgcttgg catcttggac tgagctttac t                              41

<210> SEQ ID NO 10
<211> LENGTH: 40
<212> TYPE: DNA
<213> ORGANISM: Artificial Sequence
<220> FEATURE:
<223> OTHER INFORMATION: Synthetic Construct

<400> SEQUENCE: 10 gggggtgag ttggatgtcc cccgggacac tattactcag                                 40

<210> SEQ ID NO 11
<211> LENGTH: 42
<212> TYPE: DNA
<213> ORGANISM: Artificial Sequence
<220> FEATURE:
<223> OTHER INFORMATION: Synthetic Construct

<400> SEQUENCE: 11
gggagtggaa ctgcgtcagg cttgttagag ctcatgtggt ag                             42

<210> SEQ ID NO 12
<211> LENGTH: 40
<212> TYPE: DNA
<213> ORGANISM: Artificial Sequence
<220> FEATURE:
<223> OTHER INFORMATION: Synthetic Construct

<400> SEQUENCE: 12 gtcattttc tcgccccagt ttgtggctct tgtggattag                                 40

<210> SEQ ID NO 13
<211> LENGTH: 42
<212> TYPE: DNA
<213> ORGANISM: Artificial Sequence
<220> FEATURE:
<223> OTHER INFORMATION: Synthetic Construct

<400> SEQUENCE: 13
gaacaccctg ttgttatagg gatgatagga ttacagagta ac                             42

<210> SEQ ID NO 14
<211> LENGTH: 40
<212> TYPE: DNA
<213> ORGANISM: Artificial Sequence
<220> FEATURE:
<223> OTHER INFORMATION: Synthetic Construct

<400> SEQUENCE: 14
ttgcagtagc attgcaggga acttccgcaa atgcccctgt                                40

<210> SEQ ID NO 15
<211> LENGTH: 38
<212> TYPE: DNA
<213> ORGANISM: Artificial Sequence
<220> FEATURE:
<223> OTHER INFORMATION: Synthetic Construct

<400> SEQUENCE: 15
actgtggctc cacgctcagc ccattgttgg acctggca                                  38
```

<210> SEQ ID NO 16
<211> LENGTH: 40
<212> TYPE: DNA
<213> ORGANISM: Artificial Sequence
<220> FEATURE:
<223> OTHER INFORMATION: Synthetic Construct

<400> SEQUENCE: 16
aatgctgtac cacgctcttg cttgctaaac tgtgagagtc        40

<210> SEQ ID NO 17
<211> LENGTH: 40
<212> TYPE: DNA
<213> ORGANISM: Artificial Sequence
<220> FEATURE:
<223> OTHER INFORMATION: Synthetic Construct

<400> SEQUENCE: 17
ctgtgagcgg cttcagcatc gggcgctgac gtccagatga        40

<210> SEQ ID NO 18
<211> LENGTH: 41
<212> TYPE: DNA
<213> ORGANISM: Artificial Sequence
<220> FEATURE:
<223> OTHER INFORMATION: Synthetic Construct

<400> SEQUENCE: 18
aaatgctgta ccacgctctt gcttgctaaa ctgtgagagt c        41

<210> SEQ ID NO 19
<211> LENGTH: 41
<212> TYPE: DNA
<213> ORGANISM: Artificial Sequence
<220> FEATURE:
<223> OTHER INFORMATION: Synthetic Construct

<400> SEQUENCE: 19
gagagggcct ctcaagaggc ccctgctcgc tgggttttgc a        41

<210> SEQ ID NO 20
<211> LENGTH: 38
<212> TYPE: DNA
<213> ORGANISM: Artificial Sequence
<220> FEATURE:
<223> OTHER INFORMATION: Synthetic Construct

<400> SEQUENCE: 20
ttgtaagaat tctcgaatgt ctcccccteg atattcag        38

<210> SEQ ID NO 21
<211> LENGTH: 39
<212> TYPE: DNA
<213> ORGANISM: Artificial Sequence
<220> FEATURE:
<223> OTHER INFORMATION: Synthetic Construct

<400> SEQUENCE: 21
ataagttctg cagagtacat agtccagtcg ttgtgtgat        39

<210> SEQ ID NO 22
<211> LENGTH: 41
<212> TYPE: DNA
<213> ORGANISM: Artificial Sequence
<220> FEATURE:
<223> OTHER INFORMATION: Synthetic Construct

<400> SEQUENCE: 22
tgatgagaag ccggtggtga gcagttgtac aagatccaca g					41

<210> SEQ ID NO 23
<211> LENGTH: 42
<212> TYPE: DNA
<213> ORGANISM: Artificial Sequence
<220> FEATURE:
<223> OTHER INFORMATION: Synthetic Construct

<400> SEQUENCE: 23
tacagtctac ataatcatgc cccacaacgg ctatctttag ca					42

<210> SEQ ID NO 24
<211> LENGTH: 39
<212> TYPE: DNA
<213> ORGANISM: Artificial Sequence
<220> FEATURE:
<223> OTHER INFORMATION: Synthetic Construct

<400> SEQUENCE: 24
tttgggttaa ccagtattaa gggccggttt ccattactg					39

<210> SEQ ID NO 25
<211> LENGTH: 40
<212> TYPE: DNA
<213> ORGANISM: Artificial Sequence
<220> FEATURE:
<223> OTHER INFORMATION: Synthetic Construct

<400> SEQUENCE: 25
ctggcagatg atcccctcag ccaggtctag ggcttaccct					40

<210> SEQ ID NO 26
<211> LENGTH: 40
<212> TYPE: DNA
<213> ORGANISM: Artificial Sequence
<220> FEATURE:
<223> OTHER INFORMATION: Synthetic Construct

<400> SEQUENCE: 26
tgctgccctt cagtaccgac tttggaagca gtaccgaagt					40

<210> SEQ ID NO 27
<211> LENGTH: 41
<212> TYPE: DNA
<213> ORGANISM: Artificial Sequence
<220> FEATURE:
<223> OTHER INFORMATION: Synthetic Construct

<400> SEQUENCE: 27
ttggtggaag ctgcgagtga ggggcctctc tcggtgtttc c					41

<210> SEQ ID NO 28
<211> LENGTH: 40
<212> TYPE: DNA
<213> ORGANISM: Artificial Sequence
<220> FEATURE:
<223> OTHER INFORMATION: Synthetic Construct

<400> SEQUENCE: 28
tcaacaattg ttaccttaac aaaaccgttc tagccacttt					40

<210> SEQ ID NO 29

<210> SEQ ID NO 29
<211> LENGTH: 42
<212> TYPE: DNA
<213> ORGANISM: Artificial Sequence
<220> FEATURE:
<223> OTHER INFORMATION: Synthetic Construct

<400> SEQUENCE: 29
tgctatcagt agatatcaaa tgccgtagca actcctattt ac                              42

<210> SEQ ID NO 30
<211> LENGTH: 40
<212> TYPE: DNA
<213> ORGANISM: Artificial Sequence
<220> FEATURE:
<223> OTHER INFORMATION: Synthetic Construct

<400> SEQUENCE: 30
gcatgcctgt ctaggttata tatggcgtac atttagttta                                40

<210> SEQ ID NO 31
<211> LENGTH: 42
<212> TYPE: DNA
<213> ORGANISM: Artificial Sequence
<220> FEATURE:
<223> OTHER INFORMATION: Synthetic Construct

<400> SEQUENCE: 31
ggcagaggtc aagactgaca gcaactgcgc atcaccaggc gg                             42

<210> SEQ ID NO 32
<211> LENGTH: 41
<212> TYPE: DNA
<213> ORGANISM: Artificial Sequence
<220> FEATURE:
<223> OTHER INFORMATION: Synthetic Construct

<400> SEQUENCE: 32
caactcagtc cagtattctt agggaggat tgagtttgaa t                               41

<210> SEQ ID NO 33
<211> LENGTH: 41
<212> TYPE: DNA
<213> ORGANISM: Artificial Sequence
<220> FEATURE:
<223> OTHER INFORMATION: Synthetic Construct

<400> SEQUENCE: 33
tattcccatg agttaaggag acgctggcgg gcttggccga g                              41

<210> SEQ ID NO 34
<211> LENGTH: 41
<212> TYPE: DNA
<213> ORGANISM: Artificial Sequence
<220> FEATURE:
<223> OTHER INFORMATION: Synthetic Construct

<400> SEQUENCE: 34
acagcccaag acggcttctt tcttcatccg ggctccttca g                              41

<210> SEQ ID NO 35
<211> LENGTH: 42
<212> TYPE: DNA
<213> ORGANISM: Artificial Sequence
<220> FEATURE:
<223> OTHER INFORMATION: Synthetic Construct

<400> SEQUENCE: 35
cttctcaaca ttacgacgat tgacggatca taagtagtgg ga                               42

<210> SEQ ID NO 36
<211> LENGTH: 42
<212> TYPE: DNA
<213> ORGANISM: Artificial Sequence
<220> FEATURE:
<223> OTHER INFORMATION: Synthetic Construct

<400> SEQUENCE: 36
ggtcagagta attcgacatt ctactaaggt ggacttggtt cc                               42

<210> SEQ ID NO 37
<211> LENGTH: 41
<212> TYPE: DNA
<213> ORGANISM: Artificial Sequence
<220> FEATURE:
<223> OTHER INFORMATION: Synthetic Construct

<400> SEQUENCE: 37
tatgaaagct ggacgagcag aattcccaaa ctttggtctg a                                41

<210> SEQ ID NO 38
<211> LENGTH: 42
<212> TYPE: DNA
<213> ORGANISM: Artificial Sequence
<220> FEATURE:
<223> OTHER INFORMATION: Synthetic Construct

<400> SEQUENCE: 38
ttgcccactc actagacagc cgctccatcg caaggctctc tg                               42

<210> SEQ ID NO 39
<211> LENGTH: 41
<212> TYPE: DNA
<213> ORGANISM: Artificial Sequence
<220> FEATURE:
<223> OTHER INFORMATION: Synthetic Construct

<400> SEQUENCE: 39
tatcacatta aaccgagctc agagtcttga agctacattg c                                41

<210> SEQ ID NO 40
<211> LENGTH: 40
<212> TYPE: DNA
<213> ORGANISM: Artificial Sequence
<220> FEATURE:
<223> OTHER INFORMATION: Synthetic Construct

<400> SEQUENCE: 40
agttctaatt aatggaatgc atgtgccgtt tcctggccaa                                  40

<210> SEQ ID NO 41
<211> LENGTH: 41
<212> TYPE: DNA
<213> ORGANISM: Artificial Sequence
<220> FEATURE:
<223> OTHER INFORMATION: Synthetic Construct

<400> SEQUENCE: 41
atatcagcta agcttgcagt taaaatgcgg aaaatgaaat t                                41

<210> SEQ ID NO 42
<211> LENGTH: 41
<212> TYPE: DNA

<210> SEQ ID NO 42
<211> LENGTH: 41
<212> TYPE: DNA
<213> ORGANISM: Artificial Sequence
<220> FEATURE:
<223> OTHER INFORMATION: Synthetic Construct

<400> SEQUENCE: 42
cctgcaatcc tcatgagaac gtcgtagaac tatctggccc t         41

<210> SEQ ID NO 43
<211> LENGTH: 40
<212> TYPE: DNA
<213> ORGANISM: Artificial Sequence
<220> FEATURE:
<223> OTHER INFORMATION: Synthetic Construct

<400> SEQUENCE: 43
cacccaaagt atgtggctca gcaccgtgct tataggacac            40

<210> SEQ ID NO 44
<211> LENGTH: 38
<212> TYPE: DNA
<213> ORGANISM: Artificial Sequence
<220> FEATURE:
<223> OTHER INFORMATION: Synthetic Construct

<400> SEQUENCE: 44
catttgaata gggcgtatgt ctttggttgg gcaatgaa              38

<210> SEQ ID NO 45
<211> LENGTH: 40
<212> TYPE: DNA
<213> ORGANISM: Artificial Sequence
<220> FEATURE:
<223> OTHER INFORMATION: Synthetic Construct

<400> SEQUENCE: 45
tggagtgtct actcgaggtg ttccaaatca gcggagagtc            40

<210> SEQ ID NO 46
<211> LENGTH: 42
<212> TYPE: DNA
<213> ORGANISM: Artificial Sequence
<220> FEATURE:
<223> OTHER INFORMATION: Synthetic Construct

<400> SEQUENCE: 46
gggaggttat ttatacagtg gcccaggaca cgatattaca ca         42

<210> SEQ ID NO 47
<211> LENGTH: 40
<212> TYPE: DNA
<213> ORGANISM: Artificial Sequence
<220> FEATURE:
<223> OTHER INFORMATION: Synthetic Construct

<400> SEQUENCE: 47
tggccattga tctaatgacc tcaacgatgt gtgaacaatg            40

<210> SEQ ID NO 48
<211> LENGTH: 40
<212> TYPE: DNA
<213> ORGANISM: Artificial Sequence
<220> FEATURE:
<223> OTHER INFORMATION: Synthetic Construct

<400> SEQUENCE: 48
tcacacagct ccgaagggac caactcggga tttgcagcca            40

<210> SEQ ID NO 49
<211> LENGTH: 40
<212> TYPE: DNA
<213> ORGANISM: Artificial Sequence
<220> FEATURE:
<223> OTHER INFORMATION: Synthetic Construct

<400> SEQUENCE: 49
tgaagttgct tgggacatcc tatcagtacc ataacctcaa                    40

<210> SEQ ID NO 50
<211> LENGTH: 40
<212> TYPE: DNA
<213> ORGANISM: Artificial Sequence
<220> FEATURE:
<223> OTHER INFORMATION: Synthetic Construct

<400> SEQUENCE: 50
gtgtgagagg aggcggcatc cacattcggg ggcagatgtg                    40

<210> SEQ ID NO 51
<211> LENGTH: 41
<212> TYPE: DNA
<213> ORGANISM: Artificial Sequence
<220> FEATURE:
<223> OTHER INFORMATION: Synthetic Construct

<400> SEQUENCE: 51
ctacctaaag ttgtggtgca gcttcccggc ttagtatgta a                  41

<210> SEQ ID NO 52
<211> LENGTH: 40
<212> TYPE: DNA
<213> ORGANISM: Artificial Sequence
<220> FEATURE:
<223> OTHER INFORMATION: Synthetic Construct

<400> SEQUENCE: 52
ttttgcagtc ggtctctgtg ctaattacta tcagagggag                    40

<210> SEQ ID NO 53
<211> LENGTH: 42
<212> TYPE: DNA
<213> ORGANISM: Artificial Sequence
<220> FEATURE:
<223> OTHER INFORMATION: Synthetic Construct

<400> SEQUENCE: 53
gtccttcagt ccgtgcaagg gactttacgg tactttctag ta                 42

<210> SEQ ID NO 54
<211> LENGTH: 39
<212> TYPE: DNA
<213> ORGANISM: Artificial Sequence
<220> FEATURE:
<223> OTHER INFORMATION: Synthetic Construct

<400> SEQUENCE: 54
gtctgcgtgc tgtcagtgca gtgtgactgt tgtctgtcc                     39

<210> SEQ ID NO 55
<211> LENGTH: 41
<212> TYPE: DNA
<213> ORGANISM: Artificial Sequence
<220> FEATURE:

<223> OTHER INFORMATION: Synthetic Construct

<400> SEQUENCE: 55
aacaatatga ggctcttgac agtcatagtt tagcccccctg g          41

<210> SEQ ID NO 56
<211> LENGTH: 40
<212> TYPE: DNA
<213> ORGANISM: Artificial Sequence
<220> FEATURE:
<223> OTHER INFORMATION: Synthetic Construct

<400> SEQUENCE: 56
gccaagtcta tatgctgcca aggctatatg ctgggcataa            40

<210> SEQ ID NO 57
<211> LENGTH: 40
<212> TYPE: DNA
<213> ORGANISM: Artificial Sequence
<220> FEATURE:
<223> OTHER INFORMATION: Synthetic Construct

<400> SEQUENCE: 57
ggtgaggacg gaaactgtaa actcccggga acattctggc            40

<210> SEQ ID NO 58
<211> LENGTH: 40
<212> TYPE: DNA
<213> ORGANISM: Artificial Sequence
<220> FEATURE:
<223> OTHER INFORMATION: Synthetic Construct

<400> SEQUENCE: 58
tgatcagtct aggcgttggg tcacccttta gcaccaggtc            40

<210> SEQ ID NO 59
<211> LENGTH: 40
<212> TYPE: DNA
<213> ORGANISM: Artificial Sequence
<220> FEATURE:
<223> OTHER INFORMATION: Synthetic Construct

<400> SEQUENCE: 59
ggcagaggcg ggccagtgct tggagttagc atgccctcct            40

<210> SEQ ID NO 60
<211> LENGTH: 40
<212> TYPE: DNA
<213> ORGANISM: Artificial Sequence
<220> FEATURE:
<223> OTHER INFORMATION: Synthetic Construct

<400> SEQUENCE: 60
caccagccct aggcggttaa tgactcgctc agctccttaa            40

<210> SEQ ID NO 61
<211> LENGTH: 41
<212> TYPE: DNA
<213> ORGANISM: Artificial Sequence
<220> FEATURE:
<223> OTHER INFORMATION: Synthetic Construct

<400> SEQUENCE: 61
gggtcaagaa actgtcccct tgattccgtt tagcttctca c          41

<210> SEQ ID NO 62
<211> LENGTH: 40
<212> TYPE: DNA
<213> ORGANISM: Artificial Sequence
<220> FEATURE:
<223> OTHER INFORMATION: Synthetic Construct

<400> SEQUENCE: 62
tgctgtgccg atgcggggtc tgagctcggt gaccaatagg                    40

<210> SEQ ID NO 63
<211> LENGTH: 39
<212> TYPE: DNA
<213> ORGANISM: Artificial Sequence
<220> FEATURE:
<223> OTHER INFORMATION: Synthetic Construct

<400> SEQUENCE: 63
gcagcagcac gaagcacact cgagggcgtg tctctttca                     39

<210> SEQ ID NO 64
<211> LENGTH: 40
<212> TYPE: DNA
<213> ORGANISM: Artificial Sequence
<220> FEATURE:
<223> OTHER INFORMATION: Synthetic Construct

<400> SEQUENCE: 64
gccggccctg tggcgaggca caattgtcca actgtcagcc                    40

<210> SEQ ID NO 65
<211> LENGTH: 62
<212> TYPE: DNA
<213> ORGANISM: Artificial Sequence
<220> FEATURE:
<223> OTHER INFORMATION: Synthetic Construct

<400> SEQUENCE: 65
ctcagtccta ctggataaga ccctctgccc agtaaataag ctccctgcgt gagggtagga    60
gc                                                             62

<210> SEQ ID NO 66
<211> LENGTH: 31
<212> TYPE: DNA
<213> ORGANISM: Artificial Sequence
<220> FEATURE:
<223> OTHER INFORMATION: Synthetic Construct

<400> SEQUENCE: 66
tgctggaggt aaacggctcc ccaagatgca t                             31

<210> SEQ ID NO 67
<211> LENGTH: 28
<212> TYPE: DNA
<213> ORGANISM: Artificial Sequence
<220> FEATURE:
<223> OTHER INFORMATION: Synthetic Construct

<400> SEQUENCE: 67
gcctccaacc actcgagttg gtcccaca                                 28

<210> SEQ ID NO 68
<211> LENGTH: 29
<212> TYPE: DNA
<213> ORGANISM: Artificial Sequence
<220> FEATURE:

<223> OTHER INFORMATION: Synthetic Construct

<400> SEQUENCE: 68
ttccatagta agtgcttgca gactgacaa                              29

<210> SEQ ID NO 69
<211> LENGTH: 28
<212> TYPE: DNA
<213> ORGANISM: Artificial Sequence
<220> FEATURE:
<223> OTHER INFORMATION: Synthetic Construct

<400> SEQUENCE: 69
ctgcttggta tgccgtcata cctttgct                               28

<210> SEQ ID NO 70
<211> LENGTH: 28
<212> TYPE: DNA
<213> ORGANISM: Artificial Sequence
<220> FEATURE:
<223> OTHER INFORMATION: Synthetic Construct

<400> SEQUENCE: 70
cccaaactct gtccggtaat aatttcca                               28

<210> SEQ ID NO 71
<211> LENGTH: 31
<212> TYPE: DNA
<213> ORGANISM: Artificial Sequence
<220> FEATURE:
<223> OTHER INFORMATION: Synthetic Construct

<400> SEQUENCE: 71
tagcccttaa tgcccagtcc tactttcatt c                           31

<210> SEQ ID NO 72
<211> LENGTH: 30
<212> TYPE: DNA
<213> ORGANISM: Artificial Sequence
<220> FEATURE:
<223> OTHER INFORMATION: Synthetic Construct

<400> SEQUENCE: 72
aatgatgagt caacccgaat ccccacttca                             30

<210> SEQ ID NO 73
<211> LENGTH: 32
<212> TYPE: DNA
<213> ORGANISM: Artificial Sequence
<220> FEATURE:
<223> OTHER INFORMATION: Synthetic Construct

<400> SEQUENCE: 73
agttaccatg acttggccga agactatgat tg                          32

<210> SEQ ID NO 74
<211> LENGTH: 31
<212> TYPE: DNA
<213> ORGANISM: Artificial Sequence
<220> FEATURE:
<223> OTHER INFORMATION: Synthetic Construct

<400> SEQUENCE: 74
ccaggcatca tacttggtac accatgcata g                           31

<210> SEQ ID NO 75
<211> LENGTH: 30
<212> TYPE: DNA
<213> ORGANISM: Artificial Sequence
<220> FEATURE:
<223> OTHER INFORMATION: Synthetic Construct

<400> SEQUENCE: 75
agtgagttaa tcttacccct ctcatgcatc                              30

<210> SEQ ID NO 76
<211> LENGTH: 29
<212> TYPE: DNA
<213> ORGANISM: Artificial Sequence
<220> FEATURE:
<223> OTHER INFORMATION: Synthetic Construct

<400> SEQUENCE: 76
taccatgcta gttccggtta tttcagtac                               29

<210> SEQ ID NO 77
<211> LENGTH: 29
<212> TYPE: DNA
<213> ORGANISM: Artificial Sequence
<220> FEATURE:
<223> OTHER INFORMATION: Synthetic Construct

<400> SEQUENCE: 77
ctgggcatgt cctaccctag ctgcctact                               29

<210> SEQ ID NO 78
<211> LENGTH: 28
<212> TYPE: DNA
<213> ORGANISM: Artificial Sequence
<220> FEATURE:
<223> OTHER INFORMATION: Synthetic Construct

<400> SEQUENCE: 78
cacccagggc taaccgagac aatgcaga                                28

<210> SEQ ID NO 79
<211> LENGTH: 32
<212> TYPE: DNA
<213> ORGANISM: Artificial Sequence
<220> FEATURE:
<223> OTHER INFORMATION: Synthetic Construct

<400> SEQUENCE: 79
tggctatctt gcccgcaact accaatgtat gt                           32

<210> SEQ ID NO 80
<211> LENGTH: 28
<212> TYPE: DNA
<213> ORGANISM: Artificial Sequence
<220> FEATURE:
<223> OTHER INFORMATION: Synthetic Construct

<400> SEQUENCE: 80
gttgcaacta ccagcctacc ataccaga                                28

<210> SEQ ID NO 81
<211> LENGTH: 29
<212> TYPE: DNA
<213> ORGANISM: Artificial Sequence
<220> FEATURE:
<223> OTHER INFORMATION: Synthetic Construct

<400> SEQUENCE: 81
atatgtttac agatcagact agccctagg                               29

<210> SEQ ID NO 82
<211> LENGTH: 28
<212> TYPE: DNA
<213> ORGANISM: Artificial Sequence
<220> FEATURE:
<223> OTHER INFORMATION: Synthetic Construct

<400> SEQUENCE: 82
ctggatggtc cagcgattag attacctg                                28

<210> SEQ ID NO 83
<211> LENGTH: 31
<212> TYPE: DNA
<213> ORGANISM: Artificial Sequence
<220> FEATURE:
<223> OTHER INFORMATION: Synthetic Construct

<400> SEQUENCE: 83
tacttggtag atgggtgagt ttgatagaca t                            31

<210> SEQ ID NO 84
<211> LENGTH: 30
<212> TYPE: DNA
<213> ORGANISM: Artificial Sequence
<220> FEATURE:
<223> OTHER INFORMATION: Synthetic Construct

<400> SEQUENCE: 84 cttgcccctta ggggctctat ataagcctgc                             30

<210> SEQ ID NO 85
<211> LENGTH: 38
<212> TYPE: DNA
<213> ORGANISM: Artificial Sequence
<220> FEATURE:
<223> OTHER INFORMATION: Synthetic Construct

<400> SEQUENCE: 85
gccagcctga cgggtcagag tgtcatcccg cattggtt                     38

<210> SEQ ID NO 86
<211> LENGTH: 40
<212> TYPE: DNA
<213> ORGANISM: Artificial Sequence
<220> FEATURE:
<223> OTHER INFORMATION: Synthetic Construct

<400> SEQUENCE: 86
taggaaactt acgaggcccc ttggctagga tgcggcccca                   40

<210> SEQ ID NO 87
<211> LENGTH: 42
<212> TYPE: DNA
<213> ORGANISM: Artificial Sequence
<220> FEATURE:
<223> OTHER INFORMATION: Synthetic Construct

<400> SEQUENCE: 87
agctgcaggc cgctcagaat agggacacgg gagaaatgct tt                42

<210> SEQ ID NO 88
<211> LENGTH: 40

```
<212> TYPE: DNA
<213> ORGANISM: Artificial Sequence
<220> FEATURE:
<223> OTHER INFORMATION: Synthetic Construct

<400> SEQUENCE: 88
gtttaaggag tggatacgag gaggccgctt tatctgtctg                           40

<210> SEQ ID NO 89
<211> LENGTH: 38
<212> TYPE: DNA
<213> ORGANISM: Artificial Sequence
<220> FEATURE:
<223> OTHER INFORMATION: Synthetic Construct

<400> SEQUENCE: 89
ggttcccctt gcacgttccc tgcagggacc tcggtgct                             38

<210> SEQ ID NO 90
<211> LENGTH: 38
<212> TYPE: DNA
<213> ORGANISM: Artificial Sequence
<220> FEATURE:
<223> OTHER INFORMATION: Synthetic Construct

<400> SEQUENCE: 90
cctaactttg ctggcctcag tttccgtcaa aggaggca                             38

<210> SEQ ID NO 91
<211> LENGTH: 14
<212> TYPE: DNA
<213> ORGANISM: Artificial Sequence
<220> FEATURE:
<223> OTHER INFORMATION: Synthetic Construct

<400> SEQUENCE: 91
ttgacatcag cagt                                                       14

<210> SEQ ID NO 92
<211> LENGTH: 14
<212> TYPE: DNA
<213> ORGANISM: Artificial Sequence
<220> FEATURE:
<223> OTHER INFORMATION: Synthetic Construct

<400> SEQUENCE: 92
ctgacatcag cagc                                                       14

<210> SEQ ID NO 93
<211> LENGTH: 41
<212> TYPE: DNA
<213> ORGANISM: Artificial Sequence
<220> FEATURE:
<223> OTHER INFORMATION: Synthetic Construct

<400> SEQUENCE: 93
caggaatcat cacgacttac gaaaaacgtt gagtgaaagt t                         41

<210> SEQ ID NO 94
<211> LENGTH: 39
<212> TYPE: DNA
<213> ORGANISM: Artificial Sequence
<220> FEATURE:
<223> OTHER INFORMATION: Synthetic Construct

<400> SEQUENCE: 94
```

```
gtggatgtaa atggtgtgac tctgacgtgg aagttgaga                              39

<210> SEQ ID NO 95
<211> LENGTH: 38
<212> TYPE: DNA
<213> ORGANISM: Artificial Sequence
<220> FEATURE:
<223> OTHER INFORMATION: Synthetic Construct

<400> SEQUENCE: 95
cttgaatcag caacgtcagc atcaccggtg gagttgtt                               38

<210> SEQ ID NO 96
<211> LENGTH: 40
<212> TYPE: DNA
<213> ORGANISM: Artificial Sequence
<220> FEATURE:
<223> OTHER INFORMATION: Synthetic Construct

<400> SEQUENCE: 96
accaacaggt tcaattgcca gatgacagac gctgtctgtt                             40

<210> SEQ ID NO 97
<211> LENGTH: 42
<212> TYPE: DNA
<213> ORGANISM: Artificial Sequence
<220> FEATURE:
<223> OTHER INFORMATION: Synthetic Construct

<400> SEQUENCE: 97
gtcacattga tgagtaaacc ctcctgtcgg aatctgaaag cc                          42

<210> SEQ ID NO 98
<211> LENGTH: 40
<212> TYPE: DNA
<213> ORGANISM: Artificial Sequence
<220> FEATURE:
<223> OTHER INFORMATION: Synthetic Construct

<400> SEQUENCE: 98
aggtatggcc tcgggttcga ggggctgcgg cgggaagctc                             40

<210> SEQ ID NO 99
<211> LENGTH: 8
<212> TYPE: DNA
<213> ORGANISM: Artificial Sequence
<220> FEATURE:
<223> OTHER INFORMATION: Synthetic Construct

<400> SEQUENCE: 99 tcttacac                                                                8

<210> SEQ ID NO 100
<211> LENGTH: 8
<212> TYPE: DNA
<213> ORGANISM: Artificial Sequence
<220> FEATURE:
<223> OTHER INFORMATION: Synthetic Construct

<400> SEQUENCE: 100 ccttacat                                                                8

<210> SEQ ID NO 101
<211> LENGTH: 38
<212> TYPE: DNA
<213> ORGANISM: Artificial Sequence
```

```
<220> FEATURE:
<223> OTHER INFORMATION: Synthetic Construct

<400> SEQUENCE: 101
tggaagctct tacacggtca tttgagatag cagtcatc                              38

<210> SEQ ID NO 102
<211> LENGTH: 40
<212> TYPE: DNA
<213> ORGANISM: Artificial Sequence
<220> FEATURE:
<223> OTHER INFORMATION: Synthetic Construct

<400> SEQUENCE: 102
attgcctctt atgggtgaga taatgtgtta cgtgtttcac                            40

<210> SEQ ID NO 103
<211> LENGTH: 40
<212> TYPE: DNA
<213> ORGANISM: Artificial Sequence
<220> FEATURE:
<223> OTHER INFORMATION: Synthetic Construct

<400> SEQUENCE: 103
atgaaatggc atccgatcca caaggtaatg tatggggtag                            40

<210> SEQ ID NO 104
<211> LENGTH: 39
<212> TYPE: DNA
<213> ORGANISM: Artificial Sequence
<220> FEATURE:
<223> OTHER INFORMATION: Synthetic Construct

<400> SEQUENCE: 104
acaaacgcaa cataaaggca aaatcgtata cattgtttt                             39

<210> SEQ ID NO 105
<211> LENGTH: 41
<212> TYPE: DNA
<213> ORGANISM: Artificial Sequence
<220> FEATURE:
<223> OTHER INFORMATION: Synthetic Construct

<400> SEQUENCE: 105
tataagaacc agcctctgca tgacagacct gttgtacagg g                          41

<210> SEQ ID NO 106
<211> LENGTH: 38
<212> TYPE: DNA
<213> ORGANISM: Artificial Sequence
<220> FEATURE:
<223> OTHER INFORMATION: Synthetic Construct

<400> SEQUENCE: 106
atcagatggc gggcaagctg ttttcggccc agactttc                              38

<210> SEQ ID NO 107
<211> LENGTH: 42
<212> TYPE: DNA
<213> ORGANISM: Artificial Sequence
<220> FEATURE:
<223> OTHER INFORMATION: Synthetic Construct

<400> SEQUENCE: 107
gggttggggt ttagagtgag ccctagacaa gaggaggctc tt                         42
```

<210> SEQ ID NO 108
<211> LENGTH: 41
<212> TYPE: DNA
<213> ORGANISM: Artificial Sequence
<220> FEATURE:
<223> OTHER INFORMATION: Synthetic Construct

<400> SEQUENCE: 108
tgctccaatt ctggcaaccg ccatgatgct aaagatggcc t             41

<210> SEQ ID NO 109
<211> LENGTH: 8
<212> TYPE: DNA
<213> ORGANISM: Artificial Sequence
<220> FEATURE:
<223> OTHER INFORMATION: Synthetic Construct

<400> SEQUENCE: 109 tcttacac                                                   8

<210> SEQ ID NO 110
<211> LENGTH: 8
<212> TYPE: DNA
<213> ORGANISM: Artificial Sequence
<220> FEATURE:
<223> OTHER INFORMATION: Synthetic Construct

<400> SEQUENCE: 110 ccttacat                                                   8

<210> SEQ ID NO 111
<211> LENGTH: 28
<212> TYPE: DNA
<213> ORGANISM: Artificial Sequence
<220> FEATURE:
<223> OTHER INFORMATION: Synthetic Construct

<400> SEQUENCE: 111
catgggaatg aacccaatca gtatcaac                            28

<210> SEQ ID NO 112
<211> LENGTH: 28
<212> TYPE: DNA
<213> ORGANISM: Artificial Sequence
<220> FEATURE:
<223> OTHER INFORMATION: Synthetic Construct

<400> SEQUENCE: 112
accagtgacc aaacgatgca tatgaccc                            28

<210> SEQ ID NO 113
<211> LENGTH: 31
<212> TYPE: DNA
<213> ORGANISM: Artificial Sequence
<220> FEATURE:
<223> OTHER INFORMATION: Synthetic Construct

<400> SEQUENCE: 113
ttcatccctg agacccactt aacgattggg g                        31

<210> SEQ ID NO 114
<211> LENGTH: 29
<212> TYPE: DNA
<213> ORGANISM: Artificial Sequence
<220> FEATURE:
<223> OTHER INFORMATION: Synthetic Construct

```
<400> SEQUENCE: 114
acctgagtct taggccctgg tgaaatgcc                                    29

<210> SEQ ID NO 115
<211> LENGTH: 30
<212> TYPE: DNA
<213> ORGANISM: Artificial Sequence
<220> FEATURE:
<223> OTHER INFORMATION: Synthetic Construct

<400> SEQUENCE: 115
ctgagagaca tcccagccga agaatccagc                                   30

<210> SEQ ID NO 116
<211> LENGTH: 28
<212> TYPE: DNA
<213> ORGANISM: Artificial Sequence
<220> FEATURE:
<223> OTHER INFORMATION: Synthetic Construct

<400> SEQUENCE: 116
ctgaaggagc tctgagcggg gaaaggtc                                     28

<210> SEQ ID NO 117
<211> LENGTH: 33
<212> TYPE: DNA
<213> ORGANISM: Artificial Sequence
<220> FEATURE:
<223> OTHER INFORMATION: Synthetic Construct

<400> SEQUENCE: 117
ctcgatgtgt cttacggaat actaggtcgc agc                               33

<210> SEQ ID NO 118
<211> LENGTH: 31
<212> TYPE: DNA
<213> ORGANISM: Artificial Sequence
<220> FEATURE:
<223> OTHER INFORMATION: Synthetic Construct

<400> SEQUENCE: 118
ggggtctcct tcaatgcgta atcccatcca g                                 31

<210> SEQ ID NO 119
<211> LENGTH: 30
<212> TYPE: DNA
<213> ORGANISM: Artificial Sequence
<220> FEATURE:
<223> OTHER INFORMATION: Synthetic Construct

<400> SEQUENCE: 119
ggaagacagg cactatggga agtcagcacc                                   30

<210> SEQ ID NO 120
<211> LENGTH: 30
<212> TYPE: DNA
<213> ORGANISM: Artificial Sequence
<220> FEATURE:
<223> OTHER INFORMATION: Synthetic Construct

<400> SEQUENCE: 120
agtcaaggca tttgaccatc tggctcctgg                                   30
```